US012558531B2

(12) United States Patent
Ramos de Miguel et al.

(10) Patent No.: US 12,558,531 B2
(45) Date of Patent: Feb. 24, 2026

(54) IMPLANT VIABILITY FORECASTING

(71) Applicant: Universidad de Las Palmas de Gran Canaria, Las Palmas de Gran Canaria (ES)

(72) Inventors: Angel Ramos de Miguel, Las Palmas de Gran Canaria (ES); Angel Manuel Ramos Macias, Las Palmas de Gran Canaria (ES)

(73) Assignee: Universidad de Las Palmas de Gran Canaria, Las Palmas (ES)

( * ) Notice: Subject to any disclaimer, the term of this patent is extended or adjusted under 35 U.S.C. 154(b) by 494 days.

(21) Appl. No.: 17/835,219

(22) Filed: Jun. 8, 2022

(65) Prior Publication Data

US 2022/0387781 A1 Dec. 8, 2022

(30) Foreign Application Priority Data

Jun. 8, 2021 (EP) .................................... 21382509

(51) Int. Cl.
A61N 1/04 (2006.01)
A61B 5/24 (2021.01)
(Continued)

(52) U.S. Cl.
CPC ....... A61N 1/0456 (2013.01); A61N 1/36014 (2013.01); A61B 5/24 (2021.01)

(58) Field of Classification Search
CPC .............. A61N 1/0456; A61N 1/36014; A61N 1/36039; A61N 1/0541; A61N 1/36036;
(Continued)

(56) References Cited

U.S. PATENT DOCUMENTS 5,762,612 A 6/1998 Campbell
6,077,237 A 6/2000 Campbell et al.
(Continued)

FOREIGN PATENT DOCUMENTS

AU 2014228116 B2 1/2019
DE 10249624 B4 3/2006
(Continued)

OTHER PUBLICATIONS

Anissa Boutabla et al., "Simultaneous activation of multiple vestibular pathways upon electrical stimulation of semicircular canal afferents," Journal of Neurology, Aug. 10, 2020, pp. 273-284, vol. 267, (Suppl 1).
(Continued)

*Primary Examiner* — Carl H Layno
*Assistant Examiner* — Anh-Khoa N Dinh
(74) *Attorney, Agent, or Firm* — Pilloff Passino & Cosenza LLP; Martin J. Cosenza

(57) ABSTRACT

A system including a galvanic stimulator, and an eye tracking device, wherein the system is a clinical vestibular implant suitability evaluation system. The system includes a computing apparatus configured analyze eye tracking data generated by the eye tracking device and provide output indicative of the analysis. The system is configured to evoke a vestibular reflex in a human with at least a partially functioning neural system of the human's vestibular system.

19 Claims, 25 Drawing Sheets

(51) Int. Cl.
　　*A61N 1/05* 　　(2006.01)
　　*A61N 1/36* 　　(2006.01)
　　*G06F 3/01* 　　(2006.01)

(58) Field of Classification Search
　　CPC ............ A61N 1/36038; A61N 1/36025; A61N
　　　　　　1/36082; A61N 1/36103; A61N 1/372;
　　　　　　A61N 1/37211; A61N 1/3787; A61N
　　　　　1/05; A61N 1/0548; A61N 1/3603; A61N
　　　　　1/36031; A61N 1/36034; A61N 1/36046;
　　　　　A61N 1/36067; A61N 1/37282; A61B
　　　　　5/24; G06F 3/012; G06F 3/015; G06F
　　　　　　3/013; G06F 3/011; G06F 3/016
　　　See application file for complete search history.

(56) References Cited

U.S. PATENT DOCUMENTS

| | | | |
|---|---|---|---|
| 9,861,519 | B2 | 1/2018 | Rogers et al. |
| 10,396,905 | B2 | 8/2019 | Tyler et al. |
| 10,596,371 | B1 | 3/2020 | Lisy et al. |
| 2005/0267549 | A1* | 12/2005 | Della Santina ........ A61N 1/372 |
| | | | 607/57 |
| 2007/0100214 | A1 | 5/2007 | Steinert |
| 2007/0167985 | A1* | 7/2007 | Kirby ................. A61N 1/36036 |
| | | | 607/55 |
| 2009/0082831 | A1* | 3/2009 | Paul ................... A61N 1/36031 |
| | | | 607/59 |
| 2010/0331721 | A1* | 12/2010 | Epley .................. A61B 5/4839 |
| | | | 600/558 |
| 2012/0226187 | A1 | 9/2012 | Bierer et al. |
| 2013/0066424 | A1* | 3/2013 | Hessler .............. A61N 1/36036 |
| | | | 623/10 |
| 2013/0225914 | A1* | 8/2013 | Soza ...................... A61B 5/398 |
| | | | 600/26 |
| 2015/0032186 | A1* | 1/2015 | Cushing ............. A61N 1/36038 |
| | | | 607/57 |
| 2016/0015289 | A1 | 1/2016 | Simon et al. |
| 2017/0293356 | A1 | 10/2017 | Khaderi et al. |
| 2019/0021642 | A1* | 1/2019 | Rabbitt .................. A61B 5/163 |

FOREIGN PATENT DOCUMENTS

| | | | |
|---|---|---|---|
| EP | 2811891 | A1 | 12/2014 |
| EP | 3440494 | A1 | 2/2019 |
| EP | 3167927 | B1 | 6/2019 |
| KR | 101633186 | B1 | 6/2016 |
| WO | 2016200432 | A1 | 12/2016 |
| WO | 2017123807 | A1 | 7/2017 |

OTHER PUBLICATIONS

Chih-Ming Chang et al., "Degeneration of the vestibular nerve in unilateral Meniere's disease evaluated by galvanic vestibular-evoked myogenic potentials," Clinical Neurophysiology, Jun. 19, 2017, pp. 1, 617-1, 624, vol. 128, No. 9.

J. Venhovens et al., "Vestibular evoked myogenic potentials (VEMPs) in central neurological disorders," Clinical Neurophysiology, Jan. 16, 2015, pp. 40-49, vol. 127, No. 1.

Extended European search report for European Patent Application No. 22 174 782.7.

Mohammad Mahmud et al., "The effect of galvanic vestibular stimulation on postural balance in Parkinson's disease: A systematic review and meta-analysis," Journal of the Neurological Sciences, Sep. 2022, 442, 120414.

Office Action for European Patent Application No. 22 174 782.7, mailed Apr. 2, 2024.

Xiaojie Yang et al., "Nondestructive and objective assessment of the vestibular function in rodent models: A review," Neuroscience Letters, Nov. 16, 2019, vol. 717.

Matthias Ertl et al., "Investigating the vestibular system using modern imaging techniques—A review on the available stimulation and imaging methods," Journal of Neuroscience Methods, Jul. 25, 2019, vol. 326.

Hans-Georg Schlosser et al., "Using video-oculography for galvanic evoked vestibulo-ocular monitoring in comatose patients," Journal of Neuroscience Methods, Jun. 30, 2005, pp. 127-131, vol. 145, No. 1-2.

Communication pursuant to Article 94(3) EPC in European Patent Application No. 22 174 782.7, mailed Feb. 14, 2025.

Conrad Wall III et al., "Eye Movements in Response to Electric Stimulation of the Human Posterior Ampullary Nerve," Annals of Otology, Rhinology & Laryngology, May 2007, pp. 369-374, vol. 116, No. 5.

Jean-Philippe Guyo et al., "Eye Movements in Response to Electrical Stimulation of the Lateral and Superior Ampullary Nerves," Annals of Otology, Rhinology & Laryngology, Feb. 2011, pp. 81-87, vol. 120, No. 2.

Kaibao Nie et al., "Characterization of the electrically-evoked compound action potential of the vestibular nerve," Otol Neurotol., Jan. 2011, pp. 88-97, vol. 32.

Nils Guinand et al., "Vestibular Implants: 8 Years of Experience with Electrical Stimulation of the Vestibular Nerve in 11 Patients with Bilateral Vestibular Loss," ORL J Otorhinolaryngol Relat Spec, Sep. 2015, pp. 227-240, vol 77, No. 4.

* cited by examiner

Obtaining data indicative of a response to electrical stimulation to tissue of a human.

1420

Evaluating the data.

1430

Determining, based on the evaluation, a viability of the human for a vestibular implant.

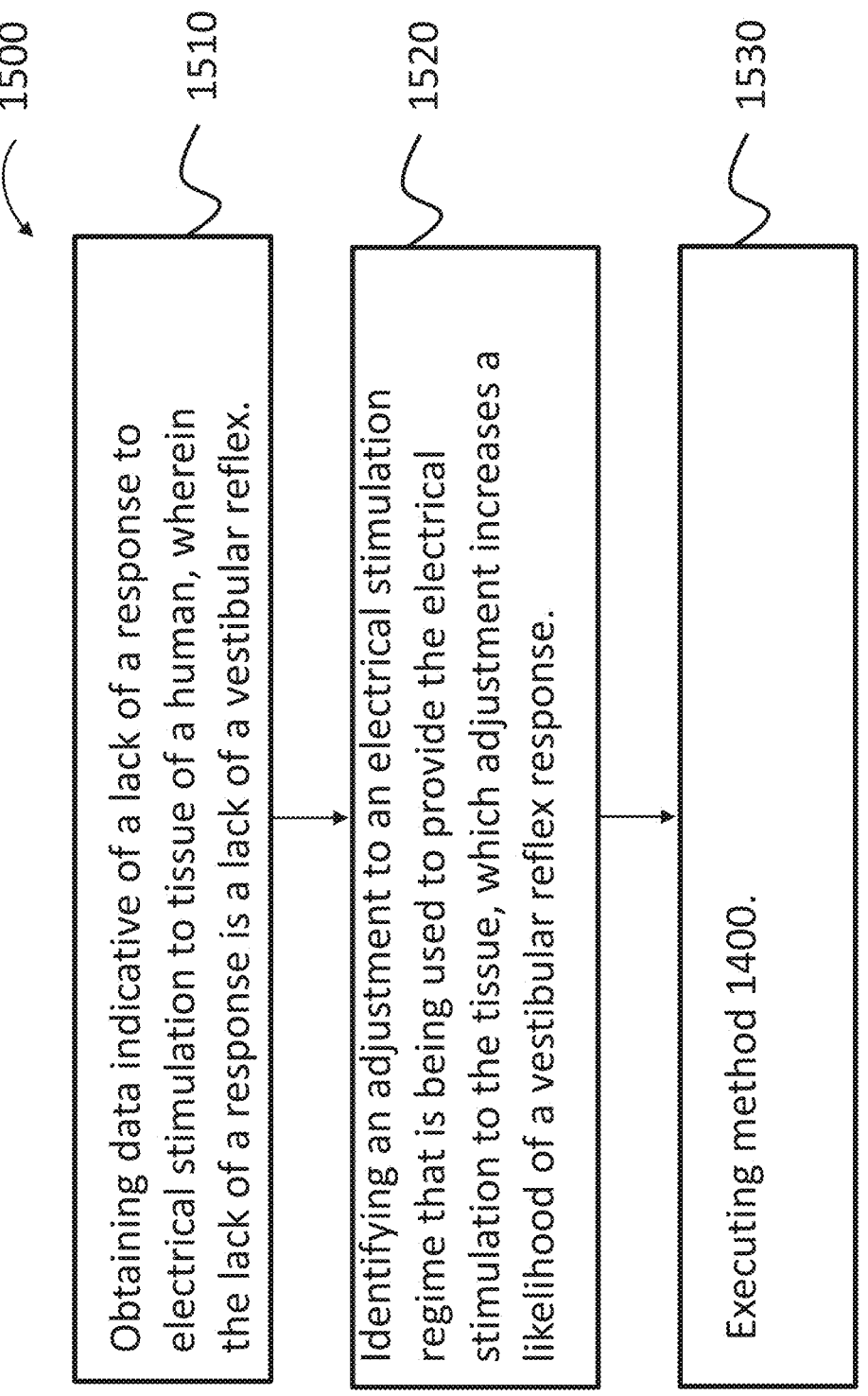

1500

1510

Obtaining data indicative of a lack of a response to electrical stimulation to tissue of a human, wherein the lack of a response is a lack of a vestibular reflex.

1520

Identifying an adjustment to an electrical stimulation regime that is being used to provide the electrical stimulation to the tissue, which adjustment increases a likelihood of a vestibular reflex response.

1530

Executing method 1400.

FIG. 15

IMPLANT VIABILITY FORECASTING

This application claims priority from European Patent Application No. EP21382509.4, filed Jun. 8, 2021, the entire contents of which are hereby incorporated by reference herein.

FUNDING STATEMENT

The project leading to this application has received funding from the European Union's Horizon 2020 research and innovation programme under grant agreement No 801127.

BACKGROUND

Medical devices have provided a wide range of therapeutic benefits to recipients over recent decades. Medical devices can include internal or implantable components/devices, external or wearable components/devices, or combinations thereof (e.g., a device having an external component communicating with an implantable component). Medical devices, such as traditional hearing aids, partially or fully-implantable hearing prostheses (e.g., bone conduction devices, mechanical stimulators, cochlear implants, etc.), pacemakers, defibrillators, functional electrical stimulation devices, and other medical devices, have been successful in performing lifesaving and/or lifestyle enhancement functions and/or recipient monitoring for a number of years.

The types of medical devices and the ranges of functions performed thereby have increased over the years. For example, many medical devices, sometimes referred to as "implantable medical devices," now often include one or more instruments, apparatus, sensors, processors, controllers or other functional mechanical or electrical components that are permanently or temporarily implanted in a recipient. These functional devices are typically used to diagnose, prevent, monitor, treat, or manage a disease/injury or symptom thereof, or to investigate, replace or modify the anatomy or a physiological process. Many of these functional devices utilize power and/or data received from external devices that are part of, or operate in conjunction with, implantable components.

SUMMARY

In an exemplary embodiment, there is a system, comprising a galvanic stimulator, and an eye tracking device, wherein the system is a clinical vestibular implant suitability evaluation system.

In an exemplary embodiment, there is a method, comprising obtaining data indicative of a response to electrical stimulation to tissue of a human, evaluating the data, and based on the evaluation, determining a viability of the human for a vestibular implant.

In an exemplary embodiment, there is an assembly, comprising electrodes, an electrode stimulator in signal communication with the electrodes, the electrode stimulator configured to generate an electrical current, which is provided to the electrodes sufficient to effectively stimulate a nervous system of a human from a location on a surface of skin of the human that evokes a response related to an ocular motor system of the human, and a reflex sensor subassembly, wherein the assembly is configured to develop reflex data using the subassembly that is correlated with data indicative of stimulation provided by the electrodes.

A vestibular function analysis assembly, comprising a first pad electrode assembly including an electrode and an adhesive configured to adhesively stick to skin of a human, a second pad electrode assembly including an electrode and an adhesive configured to adhesively stick to skin of a human, a direct current and/or alternating current generator in signal communication with the respective electrodes of the first pad electrode and the second pad electrodes, which is provided to the electrodes sufficient to effectively stimulate a nervous system of a human from a location on a surface of skin of the human that evokes a response related to an ocular motor system of the human, an ocular tracking goggles, wherein the assembly is configured to develop ocular motor reflex data using data obtained from the ocular tracking goggles that is correlated with data indicative of stimulation provided by the electrodes.

BRIEF DESCRIPTION OF THE DRAWINGS

Embodiments are described below with reference to the attached drawings, in which:

FIGS. 6 and 6A present exemplary system diagrams;

FIGS. 13A, 14 and 15 present some flowcharts of some exemplary embodiments.

DETAILED DESCRIPTION

Merely for ease of description, the techniques presented herein are described herein with reference by way of background to an illustrative medical device, namely a cochlear implant. However, it is to be appreciated that the techniques presented herein may also be used with a variety of other medical devices that, while providing a wide range of therapeutic benefits to recipients, patients, or other users, may benefit from setting changes based on the location of the medical device. For example, the techniques presented herein may be used to determine the viability of various types of prostheses, such as, for example, a vestibular implant and/or a retinal implant, with respect to a particular human being. And with regard to the latter, the techniques presented herein are also described with reference by way of background to another illustrative medical device, namely a retinal implant. The techniques presented herein are also applicable to the technology of vestibular devices (e.g., vestibular implants), visual devices (i.e., bionic eyes), sensors, pacemakers, drug delivery systems, defibrillators, functional electrical stimulation devices, catheters, seizure devices (e.g., devices for monitoring and/or treating epileptic events), sleep apnea devices, electroporation, etc.

And while the teachings detailed herein are directed towards evaluating the nerves of a vestibular system to gauge the utilitarian value of a vestibular implant for a human under testing, it is noted that any disclosure herein with respect to a vestibular system in general, and the nerves thereof in particular, as well as a vestibular implant, corresponds to a disclosure of an alternate embodiment with respect to an eye system in general, and the nerves thereof in particular, including the optic nerves, as well as a retinal implant/vision implant such disclosure being made in the interest of textual economy. To be clear, while the teachings detailed herein focus on determining the viability of a vestibular implant, based on the aforementioned statement, the teachings detailed herein are also applicable to determining the viability of a retinal implant vision implant.

Figure 1:
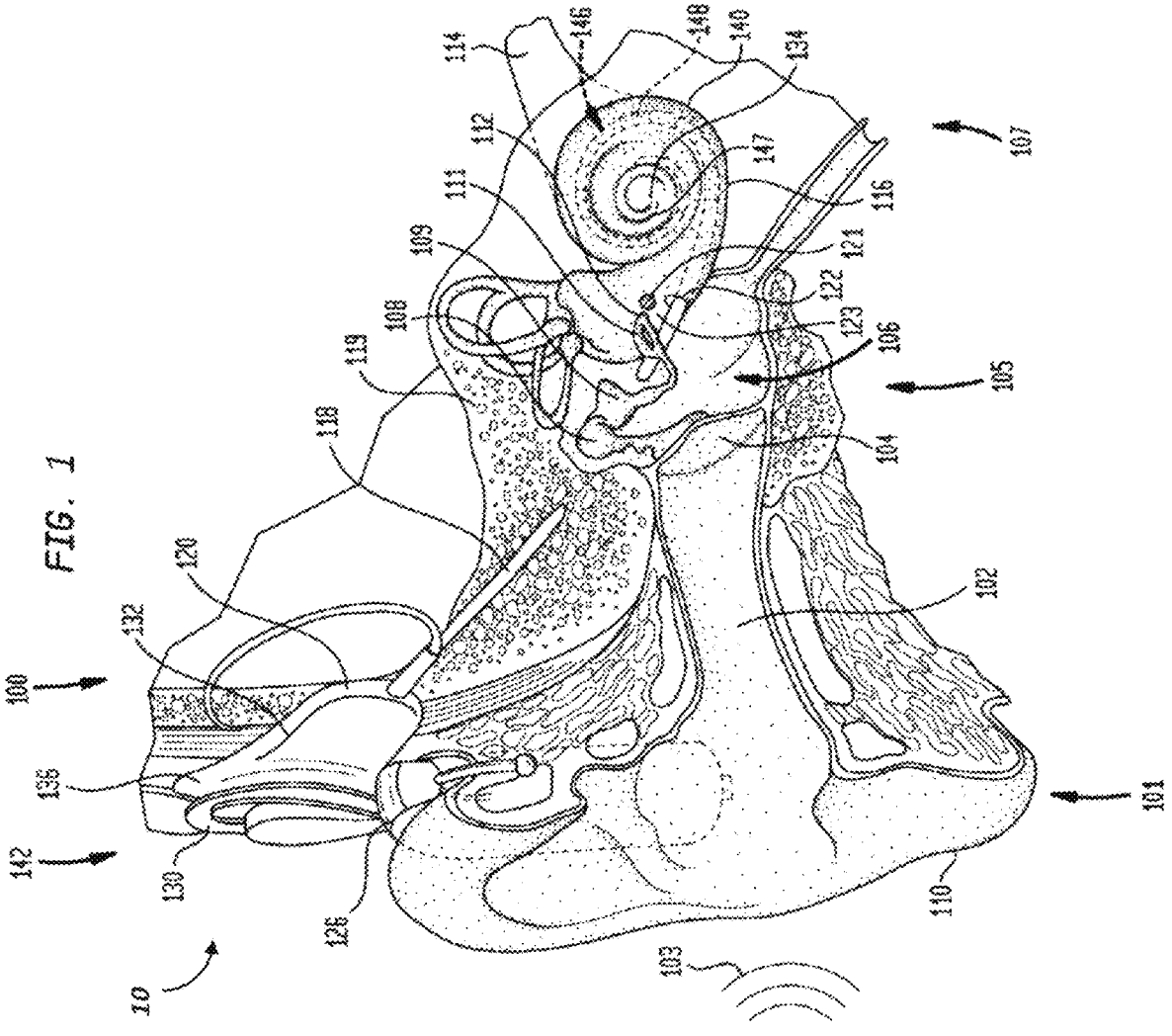
FIG. 1 is a perspective view of an exemplary hearing prosthesis.

FIG. 1 is a perspective view of a cochlear implant, referred to as cochlear implant 100, implanted in a recipient, to which some embodiments detailed herein and/or variations thereof are applicable. Particularly, as will be detailed below, there are aspects of a cochlear implant that are utilized with respect to a vestibular implant, and thus there is utility in describing features of the cochlear implant for purposes of understanding a vestibular implant. The cochlear implant 100 is part of a system 10 that can include external components in some embodiments, as will be detailed below. Additionally, it is noted that the teachings detailed herein are also applicable to other types of hearing prostheses, such as, by way of example only and not by way of limitation, bone conduction devices (percutaneous, active transcutaneous and/or passive transcutaneous), direct acoustic cochlear stimulators, middle ear implants, and conventional hearing aids, etc. Indeed, it is noted that the teachings detailed herein are also applicable to so-called multi-mode devices. In an exemplary embodiment, these multi-mode devices apply both electrical stimulation and acoustic stimulation to the recipient. In an exemplary embodiment, these multi-mode devices evoke a hearing percept via electrical hearing and bone conduction hearing.

In view of the above, it is to be understood that at least some embodiments detailed herein and/or variations thereof are directed towards a body-worn sensory supplement medical device (e.g., the hearing prosthesis of FIG. 1, which supplements the hearing sense, even in instances when there are no natural hearing capabilities, for example, due to degeneration of previous natural hearing capability or to the lack of any natural hearing capability, for example, from birth). It is noted that at least some exemplary embodiments of some sensory supplement medical devices are directed towards devices such as conventional hearing aids, which supplement the hearing sense in instances where some natural hearing capabilities have been retained, and visual prostheses (both those that are applicable to recipients having some natural vision capabilities and to recipients having no natural vision capabilities). Accordingly, the teachings detailed herein are applicable to any type of sensory supplement medical device to which the teachings detailed herein are enabled for use therein in a utilitarian manner. In this regard, the phrase sensory supplement medical device refers to any device that functions to provide sensation to a recipient irrespective of whether the applicable natural sense is only partially impaired or completely impaired, or indeed never existed.

The recipient has an outer ear 101, a middle ear 105, and an inner ear 107. Components of outer ear 101, middle ear 105, and inner ear 107 are described below, followed by a description of cochlear implant 100.

In a fully functional ear, outer ear 101 comprises an auricle 110 and an ear canal 102. An acoustic pressure or sound wave 103 is collected by auricle 110 and channeled into and through ear canal 102. Disposed across the distal end of ear channel 102 is a tympanic membrane 104 which vibrates in response to sound wave 103. This vibration is coupled to oval window or fenestra ovalis 112 through three bones of middle ear 105, collectively referred to as the ossicles 106 and comprising the malleus 108, the incus 109, and the stapes 111. Bones 108, 109, and 111 of middle ear 105 serve to filter and amplify sound wave 103, causing oval window 112 to articulate, or vibrate in response to vibration of tympanic membrane 104. This vibration sets up waves of fluid motion of the perilymph within cochlea 140. Such fluid motion, in turn, activates tiny hair cells (not shown) inside of cochlea 140. Activation of the hair cells causes appropriate nerve impulses to be generated and transferred through the spiral ganglion cells (not shown) and auditory nerve 114 to the brain (also not shown) where they are perceived as sound.

As shown, cochlear implant 100 comprises one or more components which are temporarily or permanently implanted in the recipient. Cochlear implant 100 is shown in FIG. 1 with an external device 142, that is part of system 10 (along with cochlear implant 100), which, as described below, is configured to provide power to the cochlear implant, where the implanted cochlear implant includes a battery that is recharged by the power provided from the external device 142.

In the illustrative arrangement of FIG. 1, external device 142 can comprise a power source (not shown) disposed in a Behind-The-Ear (BTE) unit 126. External device 142 also includes components of a transcutaneous energy transfer link, referred to as an external energy transfer assembly. The transcutaneous energy transfer link is used to transfer power and/or data to cochlear implant 100. Various types of energy transfer, such as infrared (IR), electromagnetic, capacitive and inductive transfer, may be used to transfer the power and/or data from external device 142 to cochlear implant 100. In the illustrative embodiments of FIG. 1, the external energy transfer assembly comprises an external coil 130 that forms part of an inductive radio frequency (RF) communication link. External coil 130 is typically a wire antenna coil comprised of multiple turns of electrically insulated single-strand or multi-strand platinum or gold wire. External device 142 also includes a magnet (not shown) positioned within the turns of wire of external coil 130. It should be appreciated that the external device shown in FIG. 1 is merely illustrative, and other external devices may be used with embodiments.

Cochlear implant 100 comprises an internal energy transfer assembly 132 which can be positioned in a recess of the temporal bone adjacent auricle 110 of the recipient. As detailed below, internal energy transfer assembly 132 is a component of the transcutaneous energy transfer link and receives power and/or data from external device 142. In the illustrative embodiment, the energy transfer link comprises an inductive RF link, and internal energy transfer assembly 132 comprises a primary internal coil 136. Internal coil 136 is typically a wire antenna coil comprised of multiple turns of electrically insulated single-strand or multi-strand platinum or gold wire.

Cochlear implant 100 further comprises a main implantable component 120 and an elongate electrode assembly 118. In some embodiments, internal energy transfer assembly 132 and main implantable component 120 are hermetically sealed within a biocompatible housing. In some embodiments, main implantable component 120 includes an implantable microphone assembly (not shown) and a sound processing unit (not shown) to convert the sound signals received by the implantable microphone in internal energy transfer assembly 132 to data signals. That said, in some alternative embodiments, the implantable microphone assembly can be located in a separate implantable component (e.g., that has its own housing assembly, etc.) that is in signal communication with the main implantable component 120 (e.g., via leads or the like between the separate implantable component and the main implantable component 120). In at least some embodiments, the teachings detailed herein and/or variations thereof can be utilized with any type of implantable microphone arrangement.

Main implantable component 120 further includes a stimulator unit (also not shown) which generates electrical stimulation signals based on the data signals. The electrical stimulation signals are delivered to the recipient via elongate electrode assembly 118.

Elongate electrode assembly 118 has a proximal end connected to main implantable component 120, and a distal end implanted in cochlea 140. Electrode assembly 118 extends from main implantable component 120 to cochlea 140 through mastoid bone 119. In some embodiments electrode assembly 118 may be implanted at least in basal region 116, and sometimes further. For example, electrode assembly 118 may extend towards apical end of cochlea 140, referred to as cochlea apex 134. In certain circumstances, electrode assembly 118 may be inserted into cochlea 140 via a cochleostomy 122. In other circumstances, a cochleostomy may be formed through round window 121, oval window 112, the promontory 123 or through an apical turn 147 of cochlea 140.

Electrode assembly 118 comprises a longitudinally aligned and distally extending array 146 of electrodes 148, disposed along a length thereof. As noted, a stimulator unit generates stimulation signals which are applied by electrodes 148 to cochlea 140, thereby stimulating auditory nerve 114.

Thus, as seen above, one variety of implanted devices depends on an external component to provide certain functionality and/or power. For example, the recipient of the implanted device can wear an external component that provides power and/or data (e.g., a signal representative of sound) to the implanted portion that allow the implanted device to function. In particular, the implanted device can lack a battery and can instead be totally dependent on an external power source providing continuous power for the implanted device to function. Although the external power source can continuously provide power, characteristics of the provided power need not be constant and may fluctuate. Additionally, where the implanted device is an auditory prosthesis such as a cochlear implant, the implanted device can lack its own sound input device (e.g., a microphone). It is sometimes utilitarian to remove the external component. For example, it is common for a recipient of an auditory prosthesis to remove an external portion of the prosthesis while sleeping. Doing so can result in loss of function of the implanted portion of the prosthesis, which can make it impossible for recipient to hear ambient sound. This can be less than utilitarian and can result in the recipient being unable to hear while sleeping. Loss of function would also prevent the implanted portion from responding to signals representative of streamed content (e.g., music streamed from a phone) or providing other functionality, such as providing tinnitus suppression noise.

The external component that provides power and/or data can be worn by the recipient, as detailed above. While a wearable external device is worn by a recipient, the external device is typically in very close proximity and tightly aligned with an implanted component. The wearable external device can be configured to operate in these conditions. Conversely, in some instances, an unworn device can generally be further away and less tightly aligned with the implanted component. This can create difficulties where the implanted device depends on an external device for power and data (e.g., where the implanted device lacks its own battery and microphone), and the external device can need to continuously and consistently provide power and data in order to allow for continuous and consistent functionality of the implanted device.

Figure 2:
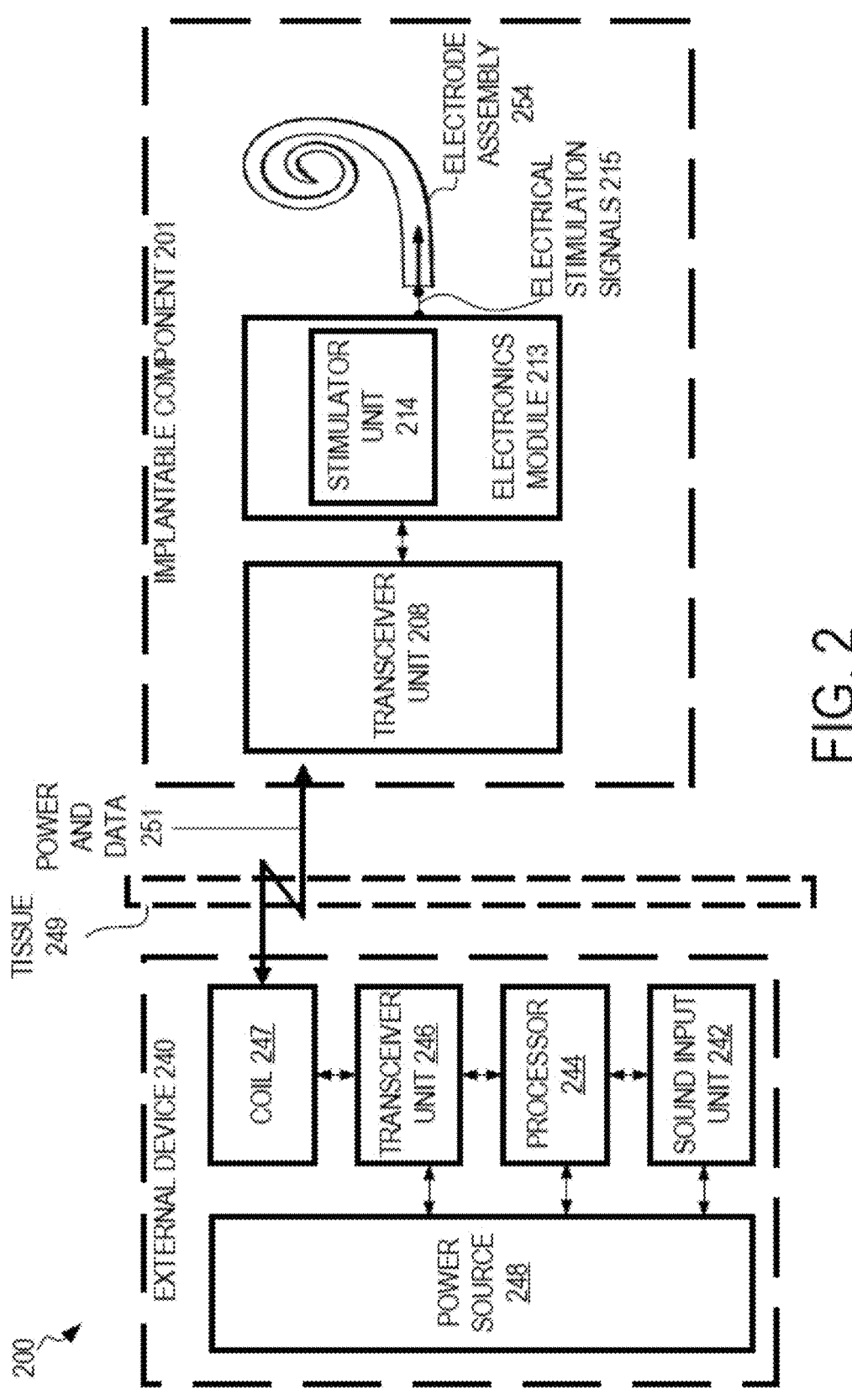
FIG. 2 presents a functional block diagram of an exemplary cochlear implant.

FIG. 2 is a functional block diagram of a cochlear implant system 200 that can benefit from the use of a pillow system in accordance with certain examples of the technology described herein. The cochlear implant system 200 includes an implantable component 201 (e.g., implantable component 100 of FIG. 1) configured to be implanted beneath a recipient's skin or other tissue 249, and an external device 240 (e.g., the external device 142 of FIG. 1).

The external device 240 can be configured as a wearable external device, such that the external device 240 is worn by a recipient in close proximity to the implantable component, which can enable the implantable component 201 to receive power and stimulation data from the external device 240. As described in FIG. 1, magnets can be used to facilitate an operational alignment of the external device 240 with the implantable component 201. With the external device 240 and implantable component 201 in close proximity, the transfer of power and data can be accomplished through the use of near-field electromagnetic radiation, and the components of the external device 240 can be configured for use with near-field electromagnetic radiation.

Implantable component 201 can include a transceiver unit 208, electronics module 213, which module can be a stimulator assembly of a cochlear implant, and an electrode assembly 254 (which can include an array of electrode contacts disposed on lead 118 of FIG. 1). The transceiver unit 208 is configured to transcutaneously receive power and/or data from external device 240. As used herein, transceiver unit 208 refers to any collection of one or more components which form part of a transcutaneous energy transfer system. Further, transceiver unit 208 can include or be coupled to one or more components that receive and/or transmit data or power. For example, the example includes a coil for a magnetic inductive arrangement coupled to the transceiver unit 208. Other arrangements are also possible, including an antenna for an alternative RF system, capacitive plates, or any other utilitarian arrangement. In an example, the data modulates the RF carrier or signal containing power. The transcutaneous communication link established by the transceiver unit 208 can use time interleaving of power and data on a single RF channel or band to transmit the power and data to the implantable component 201. In some examples, the processor 244 is configured to cause the transceiver unit 246 to interleave power and data signals, such as is described in U.S. Patent Publication Number 2009/0216296 to Meskens. In this manner, the data signal is modulated with the power signal, and a single coil can be used to transmit power and data to the implanted component 201. Various types of energy transfer, such as infrared (IR), electromagnetic, capacitive and inductive transfer, can be used to transfer the power and/or data from the external device 240 to the implantable component 201.

Aspects of the implantable component 201 can require a source of power to provide functionality, such as receive signals, process data, or deliver electrical stimulation. The source of power that directly powers the operation of the aspects of the implantable component 201 can be described as operational power. There are two exemplary ways that the implantable component 201 can receive operational power: a power source internal to the implantable component 201 (e.g., a battery) or a power source external to the implantable component. However, other approaches or combinations of approaches are possible. For example, the implantable component may have a battery but nonetheless receive operational power from the external component (e.g., to preserve internal battery life when the battery is sufficiently charged).

The internal power source can be a power storage element (not pictured). The power storage element can be configured for the long-term storage of power, and can include, for example, one or more rechargeable batteries. Power can be received from an external source, such as the external device 240, and stored in the power storage element for long-term use (e.g., charge a battery of the power storage element). The power storage element can then provide power to the other components of the implantable component 201 over time as needed for operation without needing an external power source. In this manner, the power from the external source may be considered charging power rather than operational power, because the power from the external power source is for charging the battery (which in turn provides operational power) rather than for directly powering aspects of the implantable component 201 that require power to operate. The power storage element can be a long-term power storage element configured to be a primary power source for the implantable component 201.

In some embodiments, the implantable component 201 receives operational power from the external device 240 and the implantable component 201 does not include an internal power source (e.g., a battery)/internal power storage device. In other words, the implantable component 201 is powered solely by the external device 240 or another external device, which provides enough power to the implantable component 201 to allow the implantable component to operate (e.g., receive data signals and take an action in response). The operational power can directly power functionality of the device rather than charging a power storage element of the external device implantable component 201. In these examples, the implantable component 201 can include incidental components that can store a charge (e.g., capacitors) or small amounts of power, such as a small battery for keeping volatile memory powered or powering a clock (e.g., motherboard CMOS batteries). But such incidental components would not have enough power on their own to allow the implantable component to provide primary functionality of the implantable component 201 (e.g., receiving data signals and taking an action in response thereto, such as providing stimulation) and therefore cannot be said to provide operational power even if they are integral to the operation of the implantable component 201.

As shown, electronics module 213 includes a stimulator unit 214 (e.g., which can correspond to the stimulator of FIG. 1). Electronics module 213 can also include one or more other components used to generate or control delivery of electrical stimulation signals 215 to the recipient. As described above with respect to FIG. 1, a lead (e.g., elongate lead 118 of FIG. 1) can be inserted into the recipient's cochlea. The lead can include an electrode assembly 254 configured to deliver electrical stimulation signals 215 generated by the stimulator unit 214 to the cochlea.

In the example system 200 depicted in FIG. 2, the external device 240 includes a sound input unit 242, a sound processor 244, a transceiver unit 246, a coil 247, and a power source 248. The sound input unit 242 is a unit configured to receive sound input. The sound input unit 242 can be configured as a microphone (e.g., arranged to output audio data that is representative of a surrounding sound environment), an electrical input (e.g., a receiver for a frequency modulation (FM) hearing system), and/or another component for receiving sound input. The sound input unit 242 can be or include a mixer for mixing multiple sound inputs together.

The processor 244 is a processor configured to control one or more aspects of the system 200, including converting sound signals received from sound input unit 242 into data signals and causing the transceiver unit 246 to transmit power and/or data signals. The transceiver unit 246 can be configured to send or receive power and/or data 251. For example, the transceiver unit 246 can include circuit components that send power and data (e.g., inductively) via the coil 247. The data signals from the sound processor 244 can be transmitted, using the transceiver unit 246, to the implantable component 201 for use in providing stimulation or other medical functionality.

The transceiver unit 246 can include one or more antennas or coils for transmitting the power or data signal, such as coil 247. The coil 247 can be a wire antenna coil having of multiple turns of electrically insulated single-strand or multi-strand wire. The electrical insulation of the coil 247 can be provided by a flexible silicone molding. Various types of energy transfer, such as infrared (IR), radiofrequency (RF), electromagnetic, capacitive and inductive transfer, can be used to transfer the power and/or data from external device 240 to implantable component 201.

Figure 3A:
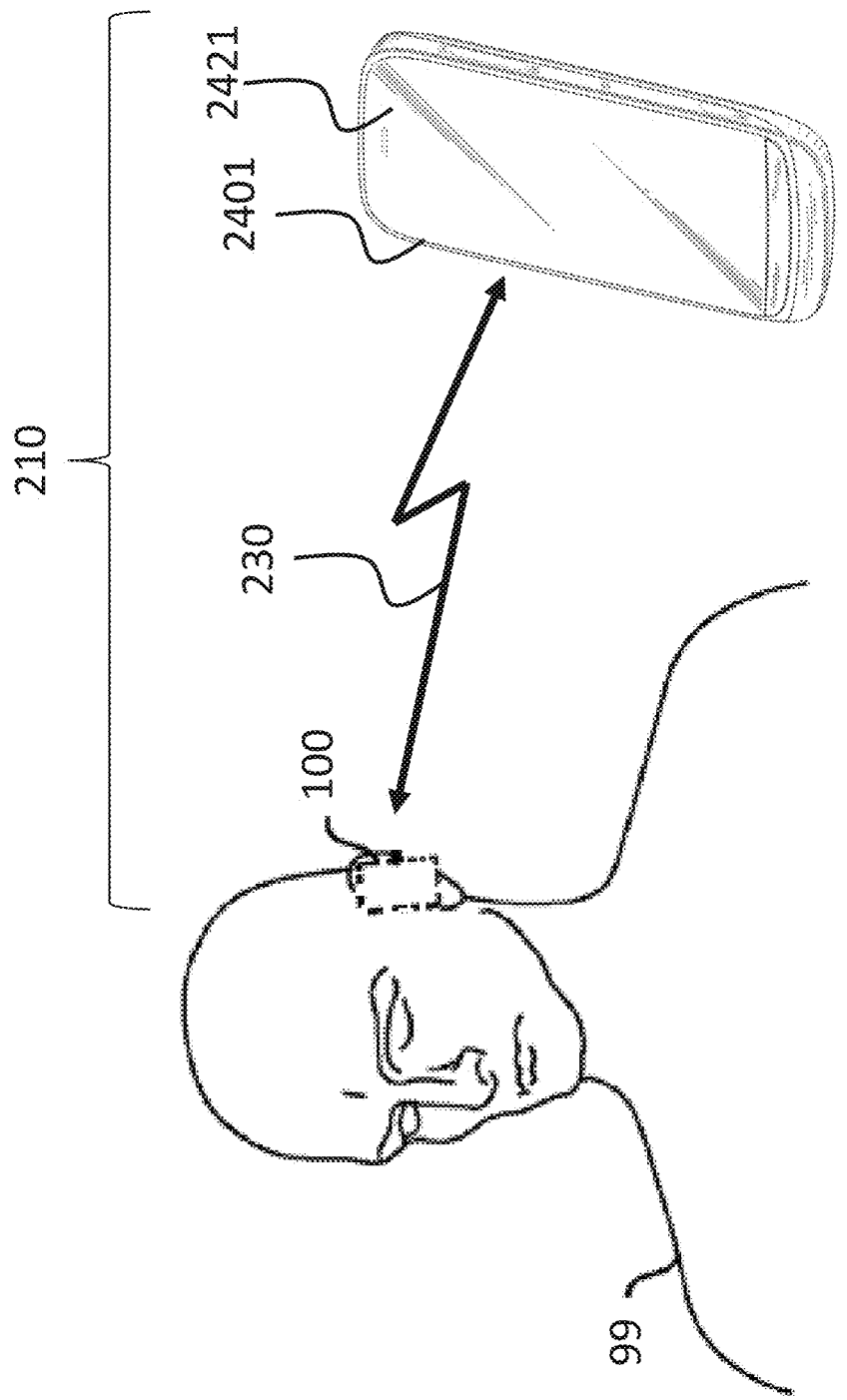
FIG. 3A and FIG. 3B and 3C present exemplary systems of communication between devices.

FIG. 3A depicts an exemplary system 210 according to an exemplary embodiment, including hearing prosthesis 100, which, in an exemplary embodiment, corresponds to cochlear implant 100 detailed above, and a portable body carried device (e.g. a portable handheld device as seen in FIG. 2A, a watch, a pocket device, etc.) 2401 in the form of a mobile computer having a display 2421. The system includes a wireless link 230 between the portable handheld device 2401 and the hearing prosthesis 100. In an embodiment, the prosthesis 100 is an implant implanted in recipient 99 (represented functionally by the dashed lines of box 100 in FIG. 3A).

In an exemplary embodiment, the system 210 is configured such that the hearing prosthesis 100 and the portable handheld device 2401 have a symbiotic relationship. In an exemplary embodiment, the symbiotic relationship is the ability to display data relating to, and, in at least some instances, the ability to control, one or more functionalities of the hearing prosthesis 100. In an exemplary embodiment, this can be achieved via the ability of the handheld device 2401 to receive data from the hearing prosthesis 100 via the wireless link 230 (although in other exemplary embodiments, other types of links, such as by way of example, a wired link, can be utilized). As will also be detailed below, this can be achieved via communication with a geographically remote device in communication with the hearing prosthesis 100 and/or the portable handheld device 2401 via link, such as by way of example only and not by way of limitation, an Internet connection or a cell phone connection. In some such exemplary embodiments, the system 210 can further include the geographically remote apparatus as well. Again, additional examples of this will be described in greater detail below.

As noted above, in an exemplary embodiment, the portable handheld device 2401 comprises a mobile computer and a display 2421. In an exemplary embodiment, the display 2421 is a touchscreen display. In an exemplary embodiment, the portable handheld device 2401 also has the functionality of a portable cellular telephone. In this regard, device 2401 can be, by way of example only and not by way of limitation, a smart phone, as that phrase is utilized generically. That is, in an exemplary embodiment, portable handheld device 2401 comprises a smart phone, again as that term is utilized generically.

It is noted that in some other embodiments, the device 2401 need not be a computer device, etc. It can be a lower tech recorder, or any device that can enable the teachings herein.

The phrase "mobile computer" entails a device configured to enable human-computer interaction, where the computer is expected to be transported away from a stationary location during normal use. Again, in an exemplary embodiment, the portable handheld device 2401 is a smart phone as that term is generically utilized. However, in other embodiments, less sophisticated (or more sophisticated) mobile computing devices can be utilized to implement the teachings detailed herein and/or variations thereof. Any device, system, and/or method that can enable the teachings detailed herein and/or variations thereof to be practiced can be utilized in at least some embodiments. (As will be detailed below, in some instances, device 2401 is not a mobile computer, but instead a remote device (remote from the hearing prosthesis 100. Some of these embodiments will be described below).)

In an exemplary embodiment, the portable handheld device 2401 is configured to receive data from a hearing prosthesis and present an interface display on the display from among a plurality of different interface displays based on the received data. Exemplary embodiments will sometimes be described in terms of data received from the hearing prosthesis 100. However, it is noted that any disclosure that is also applicable to data sent to the hearing prosthesis from the handheld device 2401 is also encompassed by such disclosure, unless otherwise specified or otherwise incompatible with the pertinent technology (and vice versa).

It is noted that in some embodiments, the system 210 is configured such that cochlear implant 100 and the portable device 2401 have a relationship. By way of example only and not by way of limitation, in an exemplary embodiment, the relationship is the ability of the device 2401 to serve as a remote microphone for the prosthesis 100 via the wireless link 230. Thus, device 2401 can be a remote mic. That said, in an alternate embodiment, the device 2401 is a stand-alone recording/sound capture device.

It is noted that in at least some exemplary embodiments, the device 2401 corresponds to an Apple Watch™ Series 1 or Series 2, as is available in the United States of America for commercial purchase as of Jan. 10, 2021. In an exemplary embodiment, the device 2401 corresponds to a Samsung Galaxy Gear™ Gear 2, as is available in the United States of America for commercial purchase as of Jan. 10, 2021. The device is programmed and configured to communicate with the prosthesis and/or to function to enable the teachings detailed herein.

Figure 3B:
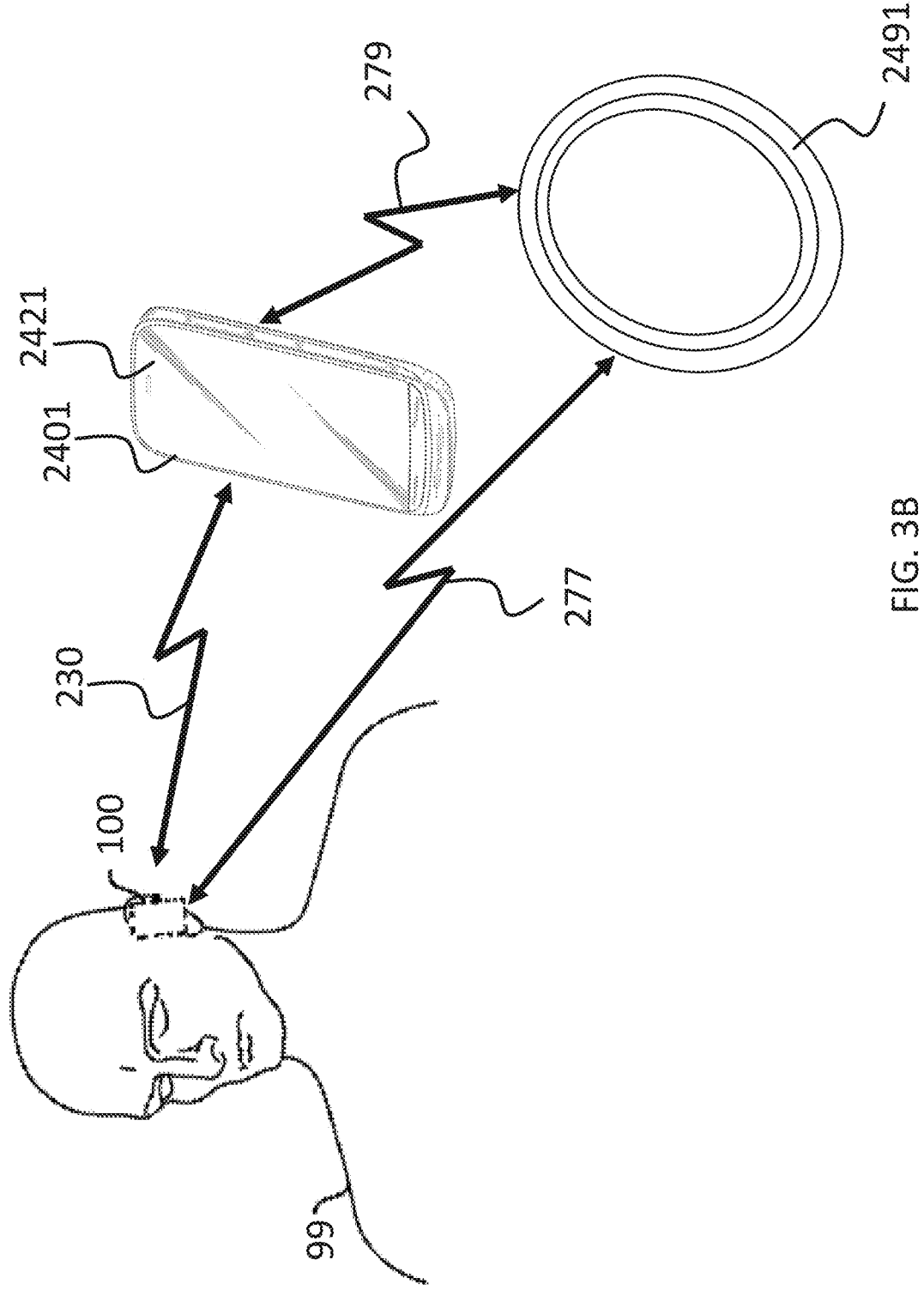

In an exemplary embodiment, a telecommunication infrastructure can be in communication with the hearing prosthesis 100 and/or the device 2401. By way of example only and not by way of limitation, a telecoil 2491 or some other communication system (Bluetooth, etc.) is used to communicate with the prosthesis and/or the remote device. FIG. 2B depicts an exemplary quasi-functional schematic depicting communication between an external communication system 2491 (e.g., a telecoil), and the hearing prosthesis 100 and/or the handheld device 2401 by way of links 277 and 279, respectively (note that FIG. 3B depicts two-way communication between the hearing prosthesis 100 and the external audio source 2491, and between the handheld device and the external audio source 2491—in alternate embodiments, the communication is only one way (e.g., from the external audio source 2491 to the respective device)). It is noted that unless otherwise noted, the embodiment of FIG. 3B is applicable to any body worn medical device/implanted device disclosed herein in some embodiments.

Figure 3C:
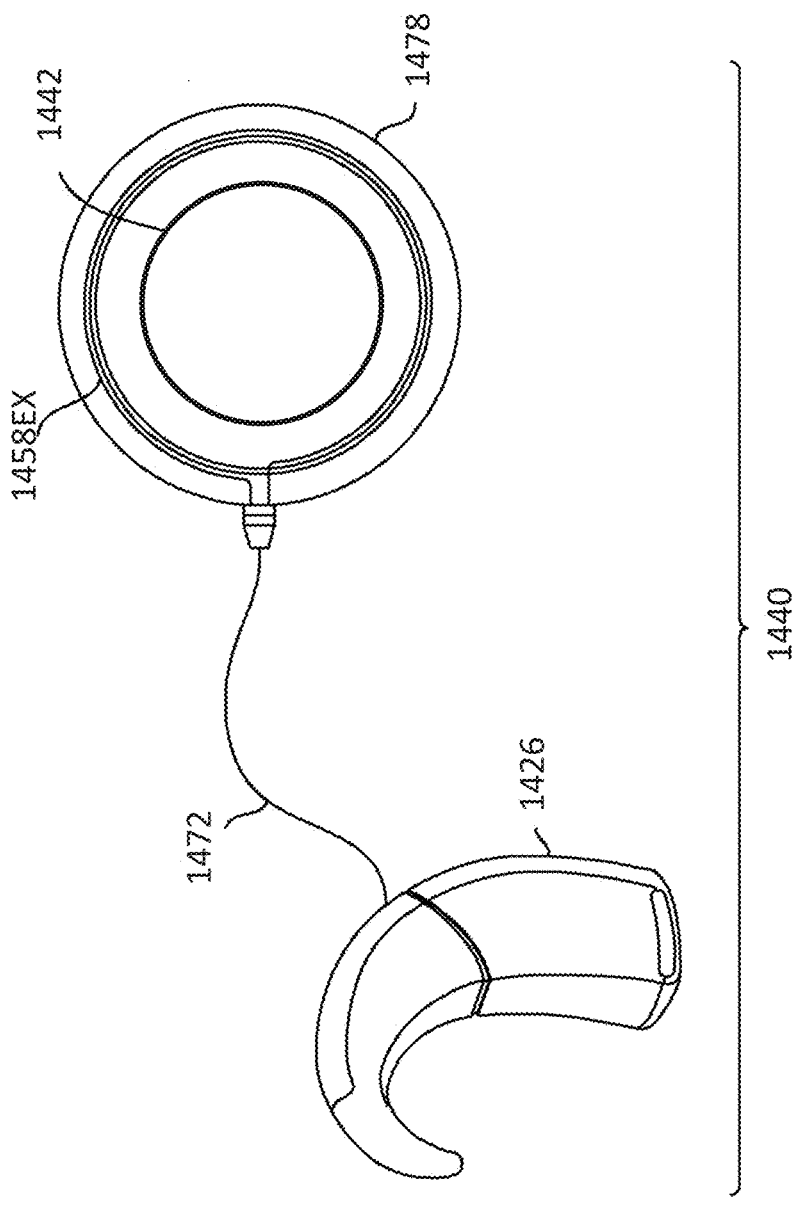

FIG. 3C depicts an exemplary external component 1440. External component 1440 can correspond to external component 142 of the system 10 (it can also represent other body worn devices herein/devices that are used with implanted portions). As can be seen, external component 1440 includes a behind-the-ear (BTE) device 1426 which is connected via cable 1472 to an exemplary headpiece 1478 including an external inductance coil 1458EX, corresponding to the external coil of FIG. 1. As illustrated, the external component 1440 comprises the headpiece 1478 that includes the coil 1458EX and a magnet 1442. This magnet 1442 interacts with the implanted magnet (or implanted magnetic material) of the implantable component to hold the headpiece 1478 against the skin of the recipient. In an exemplary embodiment, the external component 1440 is configured to transmit and/or receive magnetic data and/or transmit power transcutaneously via coil 1458EX to the implantable component, which includes an inductance coil. The coil 1458X is electrically coupled to BTE device 1426 via cable 1472. BTE device 1426 may include, for example, at least some of the components of the external devices/components described herein.

Figure 4:
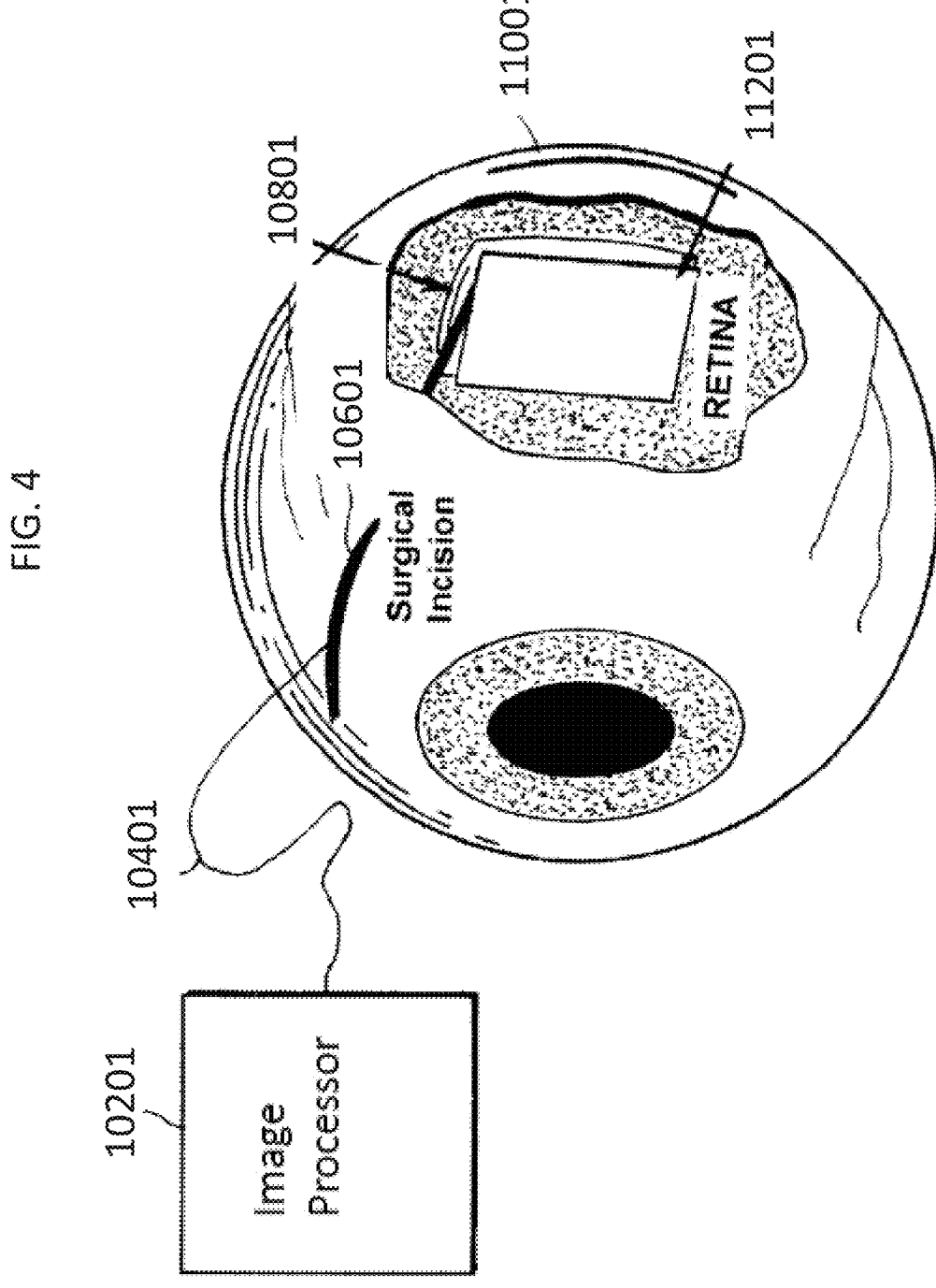
FIG. 4 presents an exemplary retinal prosthesis.

FIG. 4 presents an exemplary embodiment of a neural prosthesis in general, and a retinal prosthesis and an environment of use thereof, in particular, the components of which can be used in whole or in part, in some of the teachings herein. In some embodiments of a retinal prosthesis, a retinal prosthesis sensor-stimulator 10801 is positioned proximate the retina 11001. In an exemplary embodiment, photons entering the eye are absorbed by a microelectronic array of the sensor-stimulator 10801 that is hybridized to a glass piece 11201 containing, for example, an embedded array of microwires. The glass can have a curved surface that conforms to the inner radius of the retina. The sensor-stimulator 108 can include a microelectronic imaging device that can be made of thin silicon containing integrated circuitry that convert the incident photons to an electronic charge.

An image processor 10201 is in signal communication with the sensor-stimulator 10801 via cable 10401 which extends through surgical incision 00601 through the eye wall (although in other embodiments, the image processor 10201 is in wireless communication with the sensor-stimulator 10801). The image processor 10201 processes the input into the sensor-stimulator 10801 and provides control signals back to the sensor-stimulator 10801 so the device can provide processed output to the optic nerve. That said, in an alternate embodiment, the processing is executed by a component proximate with or integrated with the sensor-stimulator 10801. The electric charge resulting from the conversion of the incident photons is converted to a proportional amount of electronic current which is input to a nearby retinal cell layer. The cells fire and a signal is sent to the optic nerve, thus inducing a sight perception.

The retinal prosthesis can include an external device disposed in a Behind-The-Ear (BTE) unit or in a pair of eyeglasses, or any other type of component that can have utilitarian value. The retinal prosthesis can include an external light/image capture device (e.g., located in/on a BTE device or a pair of glasses, etc.), while, as noted above, in some embodiments, the sensor-stimulator 10801 captures light/images, which sensor-stimulator is implanted in the recipient.

In the interests of compact disclosure, any disclosure herein of a microphone or sound capture device corresponds to an analogous disclosure of a light/image capture device, such as a charge-coupled device. Corollary to this is that any disclosure herein of a stimulator unit which generates electrical stimulation signals or otherwise imparts energy to tissue to evoke a hearing percept corresponds to an analogous disclosure of a stimulator device for a retinal prosthesis. Any disclosure herein of a sound processor or processing of captured sounds or the like corresponds to an analogous disclosure of a light processor/image processor that has analogous functionality for a retinal prosthesis, and the processing of captured images in an analogous manner. Indeed, any disclosure herein of a device for a hearing prosthesis corresponds to a disclosure of a device for a retinal prosthesis having analogous functionality for a retinal prosthesis. Any disclosure herein of fitting a hearing prosthesis corresponds to a disclosure of fitting a retinal prosthesis using analogous actions. Any disclosure herein of a method of using or operating or otherwise working with a hearing prosthesis herein corresponds to a disclosure of using or operating or otherwise working with a retinal prosthesis in an analogous manner.

Figure 5:
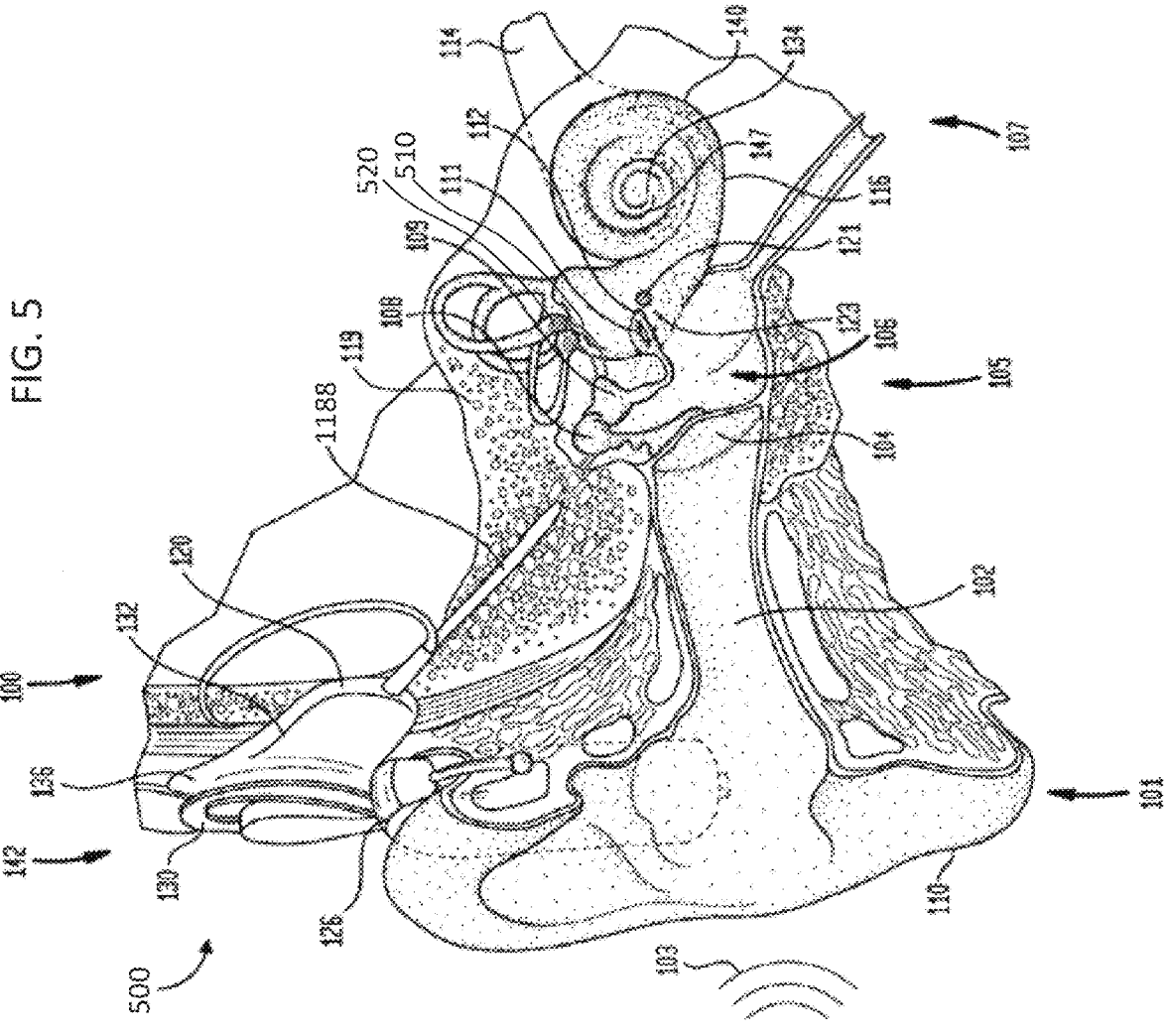
FIG. 5 presents an exemplary vestibular implant.

FIG. 5 depicts an exemplary vestibular implant 500 according to one example. Some specific features are described utilizing the above noted cochlear implant of FIG. 1 in contacts for the various elements. In this regard, some features of a cochlear implant are utilized with vestibular implants. In the interest of textual and pictorial economy, various elements of the vestibular implant that generally correspond to the elements of the cochlear implant above are referenced utilizing the same numerals. Still, it is noted that some features of the vestibular implant 500 will be different from that of the cochlear implant above. By way of example only and not by way of limitation, there may not be a microphone on the behind-the-ear device 126. Alternatively, sensors that have utilitarian value in the vestibular implant can be contained in the BTE device 126. By way of example only and not by way of limitation, motion sensors can be located in BTE device 126. There also may not be a sound processor in the BTE device. Conversely, other types of processors, such as those that process data obtained from the sensors, will be present in the BTE device 126. Power sources, such as a battery, will also be included in the BTE device 126. Consistent with the BTE device of the cochlear implant of FIG. 1, a transmitter/transceiver will be located in the BTE device or otherwise in signal communication therewith.

The implantable component includes a receiver stimulator in a manner concomitant with the above cochlear implant. Here, vestibular stimulator comprises a main implantable component 120 and an elongate electrode assembly 1188 (where the elongate electrode assembly 1188 has some different features from the elongate electrode assembly 118 of the cochlear implant, some of which will be described shortly). In some embodiments, internal energy transfer assembly 132 and main implantable component 120 are hermetically sealed within a biocompatible housing. In some embodiments, main implantable component 120 includes a processing unit (not shown) to convert data obtained by sensors, which could be on board sensors implanted in the recipient, into data signals.

Main implantable component 120 further includes a stimulator unit (also not shown) which generates electrical stimulation signals based on the data signals. The electrical stimulation signals are delivered to the recipient via elongate electrode assembly 1188.

It is briefly noted that while the embodiment shown in FIG. 5 represents a partially implantable vestibular implant, embodiments can include a totally implantable vestibular implant, such as, where, for example, the motion sensors are located in the implantable portion, in a manner analogous to a cochlear implant.

Elongate electrode assembly 1188 has a proximal end connected to main implantable component 120, and extends through a hole in the mastoid 119, in a manner analogous to the elongate electrode assembly 118 of the cochlear implant, and includes a distal end that extends to the inner ear. In some embodiments, the distal portion of the electrode assembly 1188 includes a plurality of leads 510 that branch out away from the main body of the electrode assembly 118 to electrodes 520. Electrodes 520 can be placed at the base of the semicircular ducts as shown in FIG. 5. In an exemplary embodiment, one or more of these electrodes are placed in the vicinity of the vestibular nerve branches innervating the semicircular canals. In some embodiments, the electrodes are located external to the inner ear, while in other embodiments, the electrodes are inserted into the inner ear. Note also while this embodiment does not include an electrode array located in the cochlea, in other embodiments, one or more electrodes are located in the cochlea in a manner analogous to that of a cochlear implant.

A vestibular implant can have utilitarian value with respect to a human if the human has an at least partially functioning neural system in the vestibular system. Conversely, if the neural system in the vestibular system is completely non-functional, there will be little to no utilitarian value with respect to implanting a vestibular implant in the human. Embodiments include devices, systems, and methods that can enable the determination of whether or not a human's neural system in the vestibular system has sufficient functionality that the human can at least somewhat benefit from a vestibular implant. This can have utilitarian value with respect to avoiding a scenario where a vestibular implant is implanted in the human but the implant will have little to no utilitarian value because the neural system is not sufficiently functional. Corollary to this is that a retinal implant can have utilitarian value with respect to a human if the human has and at least partially functioning neural system of the vision system.

Accordingly, the teachings herein are directed towards evaluating if a human is suitable for a vestibular implant before being implanted. At least some teachings detailed herein can enable data to be obtained that, when analyzed, can provide indicia indicative of whether or not a human's peripheral vestibular response (a response from the vestibular nerve, for example) is present and/or is sufficient enough to render the human a candidate for the utilitarian outcome with respect to a vestibular implant. The data can be data indicative of a vestibular never function, at least some function. Still further, the teachings detailed herein are directed towards, in some other embodiments, evaluating if a human is suitable for a retinal implant before being implanted. At least some teachings detailed herein can enable data to be obtained that, when analyzed, can provide indicia indicative of whether or not a human's response to electrical stimulation in the eye or otherwise the response to electrical stimulation of the nerves of the optical system is present and/or is sufficient enough to render the human a candidate for the utilitarian outcome with respect to a retinal implant.

It is also noted that at least some exemplary embodiments are directed towards evaluating whether a semicircular canal implant can have utilitarian value with respect to a given human under testing. That is, at least some exemplary embodiments include devices systems and methods of screening humans for semicircular canal implants Some embodiments utilize Galvanic Vestibular Stimulation (GVS)—monopolar and/or bipolar, placed unilaterally or bilaterally, to evoke a sensation of movement with the human's head and/or body in its entirety in a stationary position. In an exemplary embodiment the GVS is used for monolateral stimulation (but both "sides" can be stimulated, in a serial or spaced apart manner, providing that there is sufficient temporal spacing between the stimulations). Embodiments include providing a weak current (AC or DC, depending on the embodiment) across the mastoid processes. This current is utilized to excite one or more of the otoliths and semicircular canal afferents. Embodiments can include a continuous stimulation and/or a pulse stimulation and/or a sine wave. Noise stimulation can be used as well.

More specifically, in at least some exemplary embodiments, the aforementioned current is utilized to evoke a sensation of head roll around a naso-occipital axis, canals stimulation. In some exemplary embodiments, evoked torsional eye movement response to GVS is obtained, and otherwise captured, and evaluated. If sufficient movement is present, this can be indicative of a sufficiently functioning neural system of the vestibular system, thus indicating that the human can have utilitarian experience with respect to a vestibular implant.

Some exemplary embodiments utilize the GVS to excite the synapse between vestibular hair cells and the eighth nerve afferents. Embodiments herein can thus provide information regarding "neural" rather than "sensory" function. Humans with hair-cell damage (e.g., from ototoxic drug exposure) who have a preserved eighth nerve afferent function can have normal or even increased responses to galvanic vestibular stimulation despite absent responses to caloric and rotational testing.

Figure 6:
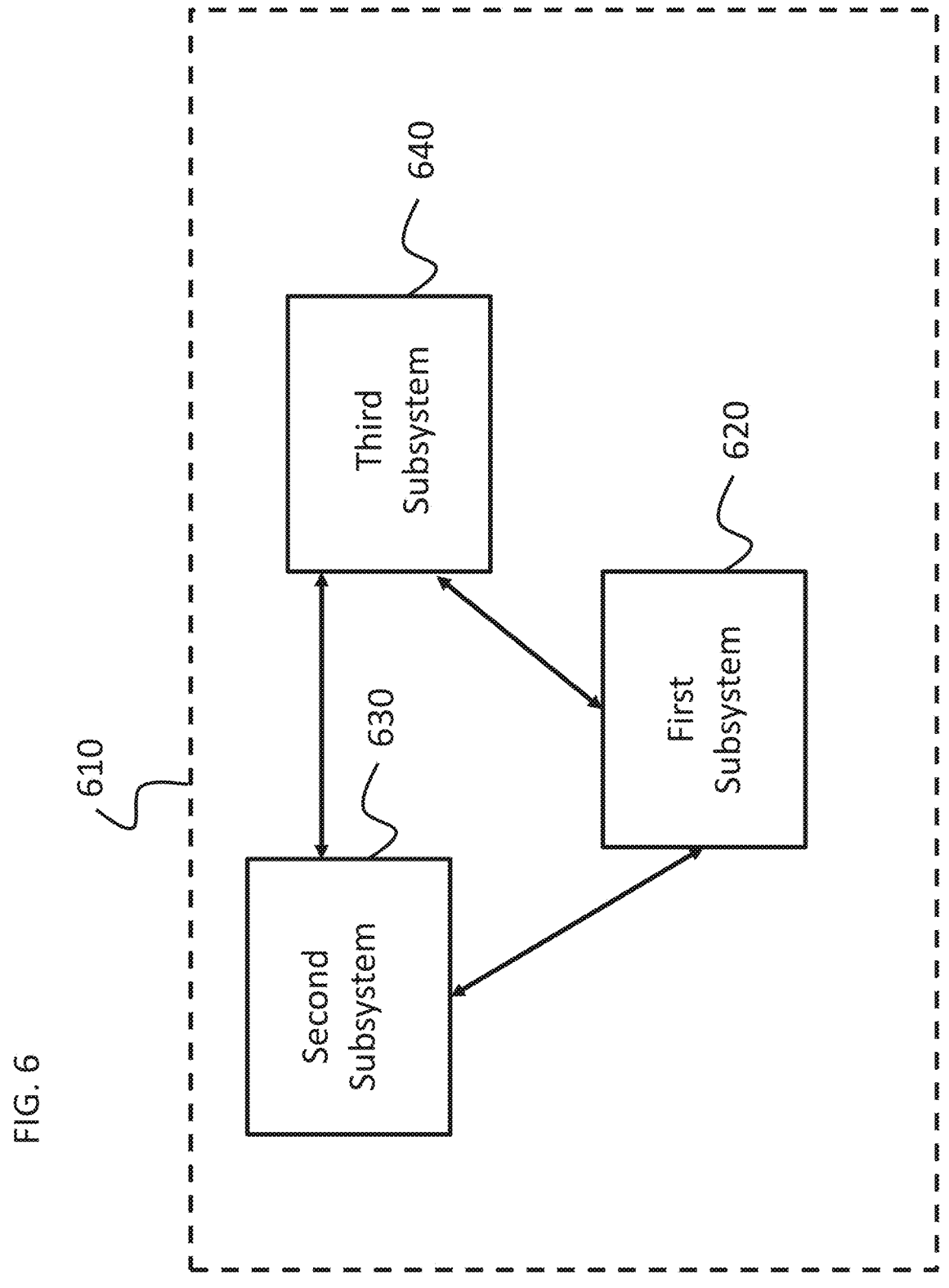

FIG. 6 presents a functional schematic of an exemplary system 610 according to an exemplary embodiment. Here, system 610 can be a clinical vestibular implant suitability evaluation system. FIG. 6 depicts the system 610 as including three subsystems. There is a control subsystem 620 (a first subsystem), a galvanic stimulator 630 (a second subsystem), and an eye tracking device 640 (a third subsystem). As shown in FIG. 6, each of these subsystems is in bidirectional communication with each other. It is noted that in some exemplary embodiments, one or more of the communications between one or more of the subsystems is unidirectional. It is also noted that while some embodiments, including many of the embodiments presented herein, present the subsystems as being in wired communication with each other, in other embodiments, one or more of the subsystems is in wireless communication with one or more of the other, such as by way of example only and not by way of limitation, communication that can be achieved through a Bluetooth communication link. Any device, system, and/or method that can enable utilitarian communication between the various subsystems can be utilized in at least some exemplary embodiments. Moreover, it is noted that in at least some exemplary embodiments, the system 610 can include subsystems that are remote from one another. By way of example only and not by way of limitation, the control subsystem 620 can be located remotely from the galvanic stimulator 630 and the eye tracking device 640. For example, the control subsystem 620 can be located at a remote healthcare center tens or hundreds or thousands of miles away from the human undergoing testing, and thus can be located at these distances from the galvanic stimulator 630 and the eye tracking device 640. Moreover, portions of the subsystems can be located over wide geographic areas. The eye tracking device 640 can be a device that has working sensors that track the eye and output signals that can be transmitted to a remote processor or other analytical device, which can be tens or hundreds or thousands of miles away from the working sensors.

In an exemplary embodiment, the galvanic stimulator provides GVS that can have a stimulus pattern that is stochastic, continuous or sinusoidal. In an exemplary embodiment, the stimulus pattern can be varied and different stimulus patterns can be utilized for the same human, such as in the event that one stimulus pattern does not evoke a response, and other stimulus pattern can be utilized that may or may not evoke a response. Accordingly, at least some exemplary stimulators are configured to provide one, two and/or all three of these patterns, in a selectable and/or in a automatic matter.

Accordingly, at least some exemplary embodiments include telemedicine regimes where the control of the method takes place at one geographic location and the stimulation and sensing takes place at another geographic location, which can be executed, by way of example only and not by way of limitation, over the Internet. Details of this will be described in greater detail below. Note also that in an exemplary embodiment, the control subsystem 620 can have varying utility. Briefly, in the embodiment contemplated in FIG. 6, the control subsystem controls the galvanic stimulator 630, but does not receive input or otherwise data from the eye tracking device 640. Instead, the data from the eye tracking device 640 is provided to another subsystem, an analytical subsystem, 650 (a fourth subsystem), as shown in the system 610A of FIG. 6A, where the data can be analyzed. Such an exemplary embodiment can have utilitarian value with respect to having a technician interface with the human undergoing the testing and otherwise set up the test system and apply the stimulation and obtain the general basic eye tracking data. The obtained general basic eye tracking data can be provided (with or without correlative data regarding the electrical stimulation applied to obtain the eye tracking data (which can be no eye movements)) to the analytical subsystem 650, where the data can be analyzed and evaluated, in a determination can be made whether or not the human is a candidate for a vestibular implant. Thus, the analytical subsystem can be located remotely from the control subsystem. This can have utilitarian value with respect to establishing a centralized location where a healthcare expert/a healthcare professional can evaluate the data without actually having to execute the test or otherwise be present for the test.

Figure 6A:
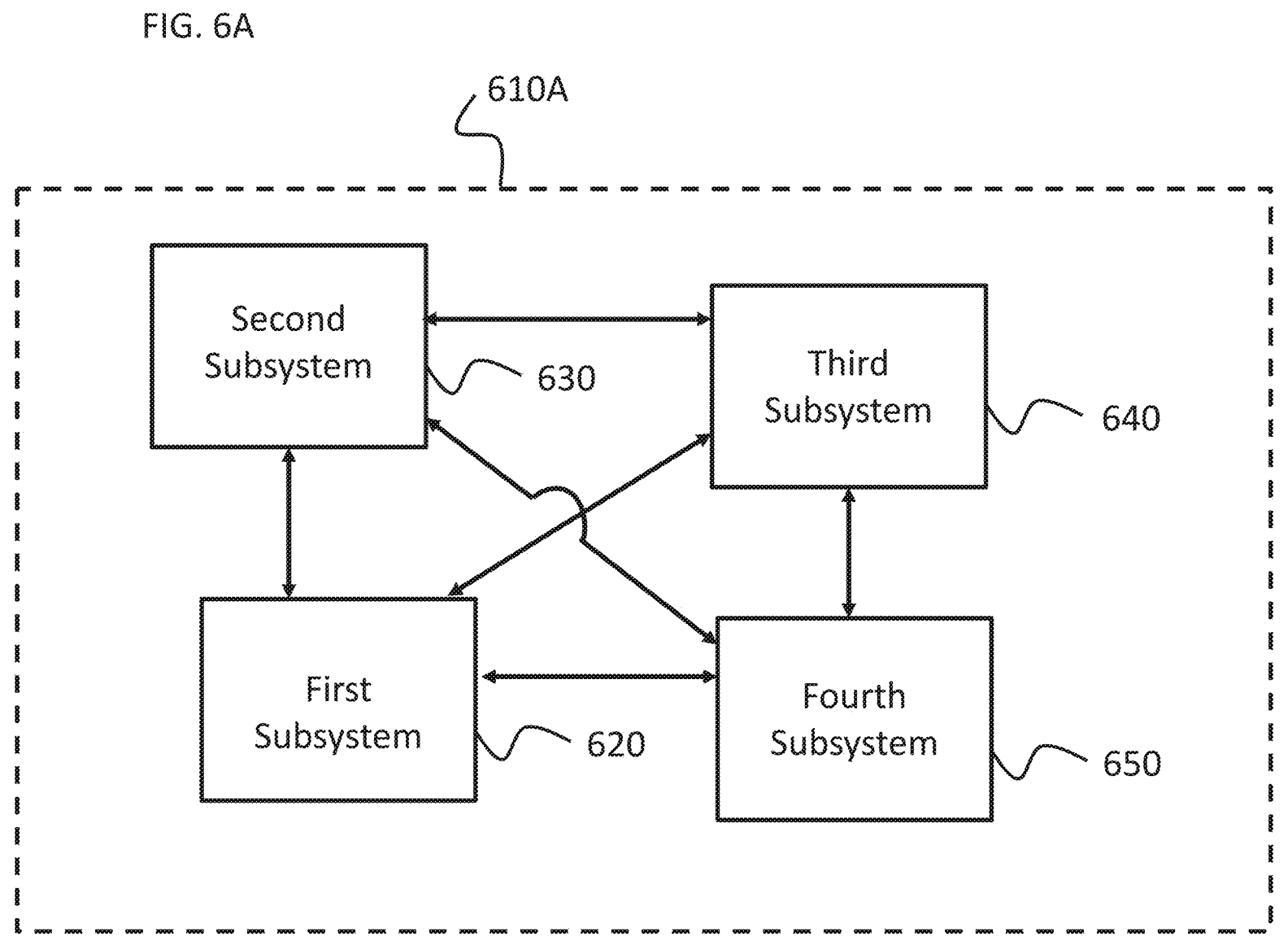

FIG. 6A shows various communication regimes that may or may not be present between the various subsystems in a manner analogous to the communication regime of system 610 above.

Converse to the concept of one or more of the subsystems being located remotely to one another, in an exemplary embodiment, system 610 can be an integrated system where all of the sub systems are part of a single apparatus, such as a head worn device as will be described in greater detail below. Moreover, subsystem 630 and subsystem 640 can be located or otherwise be a part of a single apparatus, such as a head worn apparatus, where controller 620 and/or analysis subsystem 650 is in wired or wireless signal communication therewith.

Some exemplary features of the exemplary subsystems will now be described, but briefly, it can be seen that in an exemplary embodiment, there is a system that comprises a galvanic stimulator and an eye tracking device, wherein the system is a clinical vestibular implant suitability evaluation system.

Figure 7:
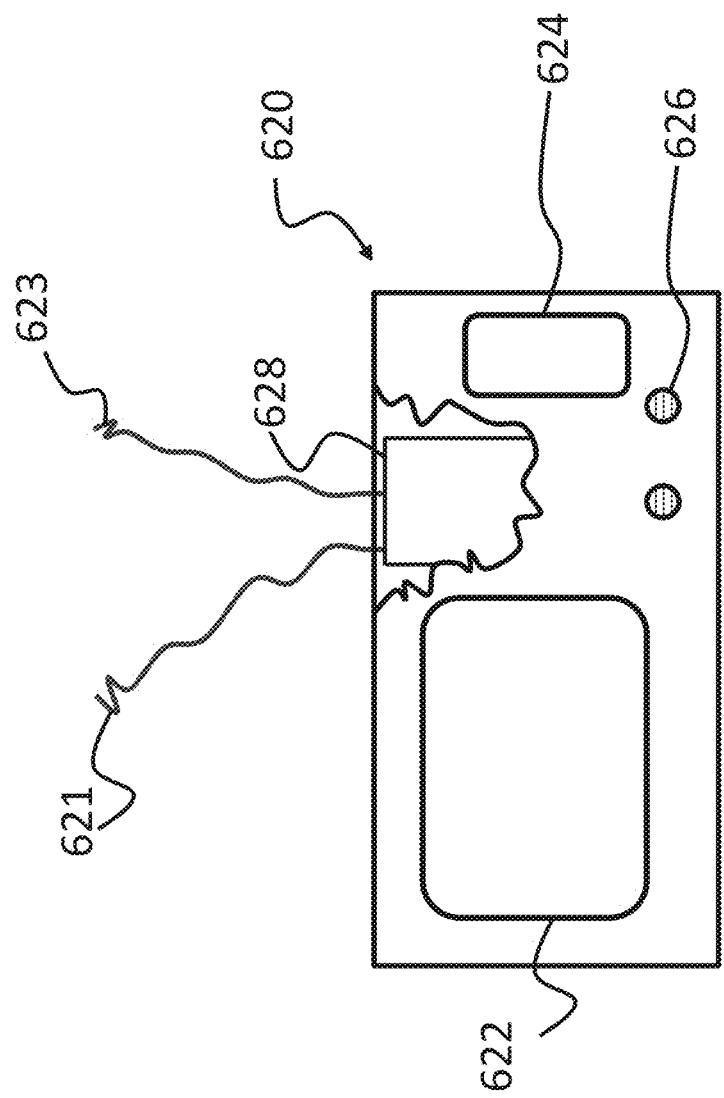
FIGS. 7 to 8A present some exemplary sub-system diagrams.

FIG. 7 presents an exemplary embodiment of an exemplary system control device 620, corresponding to the control subsystem 620 of FIG. 6 and/or 6A. In this exemplary embodiment, control device 620 is configured to control the stimulation applied to the human via leads 621, which are in wired communication to the galvanic stimulator 630, and receive input indicative of eye movement via lead 623, which is in wired communication with the eye tracking device 640. More specifically, system control device 620 can be a specially designed assembly that includes a housing that supports a display 622, such as an LCD, and a control input suite 624, which can be a touch screen and/or a keypad and/or a pushbutton arrangement. Rheostatic analogue or digital knobs 626 can also be included in the assembly for improper purposes. All of the aforementioned components are in signal communication with processor suite 628, which can be computer circuitry such as chip based circuitry and/or a motherboard that includes a microprocessor, etc. The processor suite 628 includes logic circuitry to execute one or more of the method actions detailed herein or otherwise provide one or more functionalities associated with the controller 620 detailed herein. The processor suite 628 is configured to receive input from the control input suite 624 and/or knobs 626 and automatically analyze the importer otherwise utilize the input to provide an output via leads 621 to the galvanic stimulator 630 so as to control the galvanic simulator 630 or otherwise provide instructions of the galvanic stimulator 630 so that the galvanic stimulator will provide stimulation to the human via the electrodes thereof (more on this below). In an exemplary embodiment, such as where input suite 624 is a touchscreen, a virtual set of 10 or 15 or 20 "buttons" can be presented in a manner somewhat analogous to the dial pad of a smart phone or the like, each button representing a current level that can be provided by the galvanic stimulator. By touching the button, a signal will be provided from the touchscreen to the processor suite 628 which includes logic circuits to interpret the signal, and then using the logic circuits or other circuitry, will output a signal via electrical leads 621 to instruct the galvanic stimulator to provide the stimulation at that level. Alternatively and/or in addition to this, the rheostatic knobs 626 can be turned so as to adjust a signal outputted there from which will be received by the processor suite 628, and where the logic circuitry thereof will analyze that signal and operate in a manner just detailed with respect to the touchscreen 624. The knobs 626 can be analog or can be digital (a mechanical leaf spring can be used to force discrete rotation amounts).

While the embodiment just detailed relies upon the processor suite 628 to receive the signals from the input suite, and thus interpret those signals to develop an output, in an alternative embodiment, the processor suite can be eliminated or otherwise component 628 represents a circuit board that supports various input components and provides an electrical conduit to leads 621. By way of example only and not by way of limitation, the knobs 626 can be rheostats in signal communication with leads 621. Adjustments of the knobs 626 adjust the voltage that is provided to leads 621, and thus to the galvanic stimulator. The galvanic stimulator can read the voltage and determine the stimulation level. It is briefly noted that the control device 620 can be powered by grid utility power (120 v/240 v, 50-60 Hz) and/or can be powered by one or more batteries (rechargeable or otherwise). In an exemplary embodiment, control device 620 can be powered by eight (8) D cell batteries wired in series so as to establish a 12 volt power supply, and the rheostats can be configured to provide an output in one (1) volt increments to the galvanic stimulator, whereby the galvanic stimulator will "read" the output voltage and determine the stimulation level to be applied to the human.

It is also noted that in an exemplary embodiment, the input suite 624 or another device, such as a dedicated button, can be utilized to control the timing and/or the initiation of the stimulation provided by the galvanic stimulator. By way of example only and not by way of limitation, even though the rheostatic knobs have been set to output a signal that is at 9 V, the signal will not be outputted until the "activation" button is depressed. In an exemplary embodiment, the signal is outputted for long as the activation button is depressed, and the galvanic stimulator stimulates for as long as the signal is being received, and then stops upon receipt of the signal. In an exemplary embodiment, the galvanic stimulator has pre-programmed or otherwise predetermined stimulation times, and all that need be provided is the signal to initiate the stimulation.

Still with reference to FIG. 7, it can be seen that the control device 620 is configured to receive input via electrical leads 623 from the eye tracking device. In an exemplary embodiment, electrical leads 623 provide a signal output from the eye tracking device. This can be a raw signal indicative of eye movements (analogous to the output of a microphone, for example), or can be a process signal that provides already process data indicative of eye movements. Additional details of this will be described below after the details of the eye tracking device and the use thereof are presented.

It is briefly noted that alternatively and/or in addition to the electrical leads 621 and 623, wireless communication, such as by way of example only and not by way of limitation, a Bluetooth communication, can be utilized to communicate with the galvanic stimulator and/or the eye tracker. Accordingly, in an exemplary embodiment, the processor suite can include, for example, a Bluetooth chip.

At least some exemplary embodiments of the control device 620 include one or more features that can be found in a general purpose computer, such as a laptop computer. Accordingly, in an exemplary embodiment, any one or more of the functionalities of the control device 620 detailed above can be implemented utilizing any appropriate portion of a laptop computer providing that the art enable such.

Figure 7A:
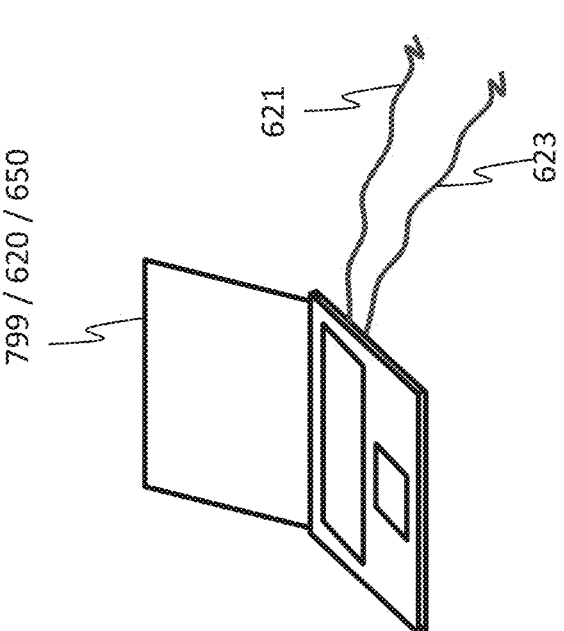

Indeed, FIG. 7A presents a schematic of a laptop 799. Laptop 799 can correspond to the control device 620 otherwise have any one or more of the functionalities of the control device detailed herein. In an exemplary embodiment, the laptop can be in signal communication with the galvanic stimulator and/or the eye trackers via electrical leads that interface with the laptop via USB port or the like. Alternatively, and/or in addition to this, wireless communication, such as via a Bluetooth signal, can establish the communication. It is briefly noted that this can also represent, in an alternate embodiment, the analytical device 650. Some details of the processing or otherwise the handling of data received from the eye trackers 640 will be described below after the operation of the eye tracker is described.

In an exemplary embodiment, the keyboard of the laptop 799 can be utilized to input the control data for control of the galvanic stimulator. Alternatively, or in addition to this, the display can be a touchscreen display. Further, such as in embodiments that utilize voice recognition, speech commands can be utilized to input the control data. The software on board the laptop can evaluate the data and provide an output signal to the galvanic stimulator 630, which output signal is developed based on the input. That said, the software on board the laptop need not be evaluative per se. Instead, the laptop can be programmed or otherwise configured to be more of a multimedia device if you will, that enables the transfer of the instructions/settings to the galvanic stimulator. Indeed, this can be the case with respect to scenarios of use where the control subsystem is located remotely from the galvanic stimulator. The laptop computer can be utilized to access the Internet for example and/or to enable cloud computing, whereby the galvanic stimulator can be instructed over the cloud. And note also that the bifurcated/trifurcated, etc., arrangements permit control to be in one room for example, and the stimulator to be located in an adjacent room or another room down the hall.

Any device, system, and/or method that can enable the galvanic stimulator to be controlled can be utilized in at least some exemplary embodiments.

Figure 8:
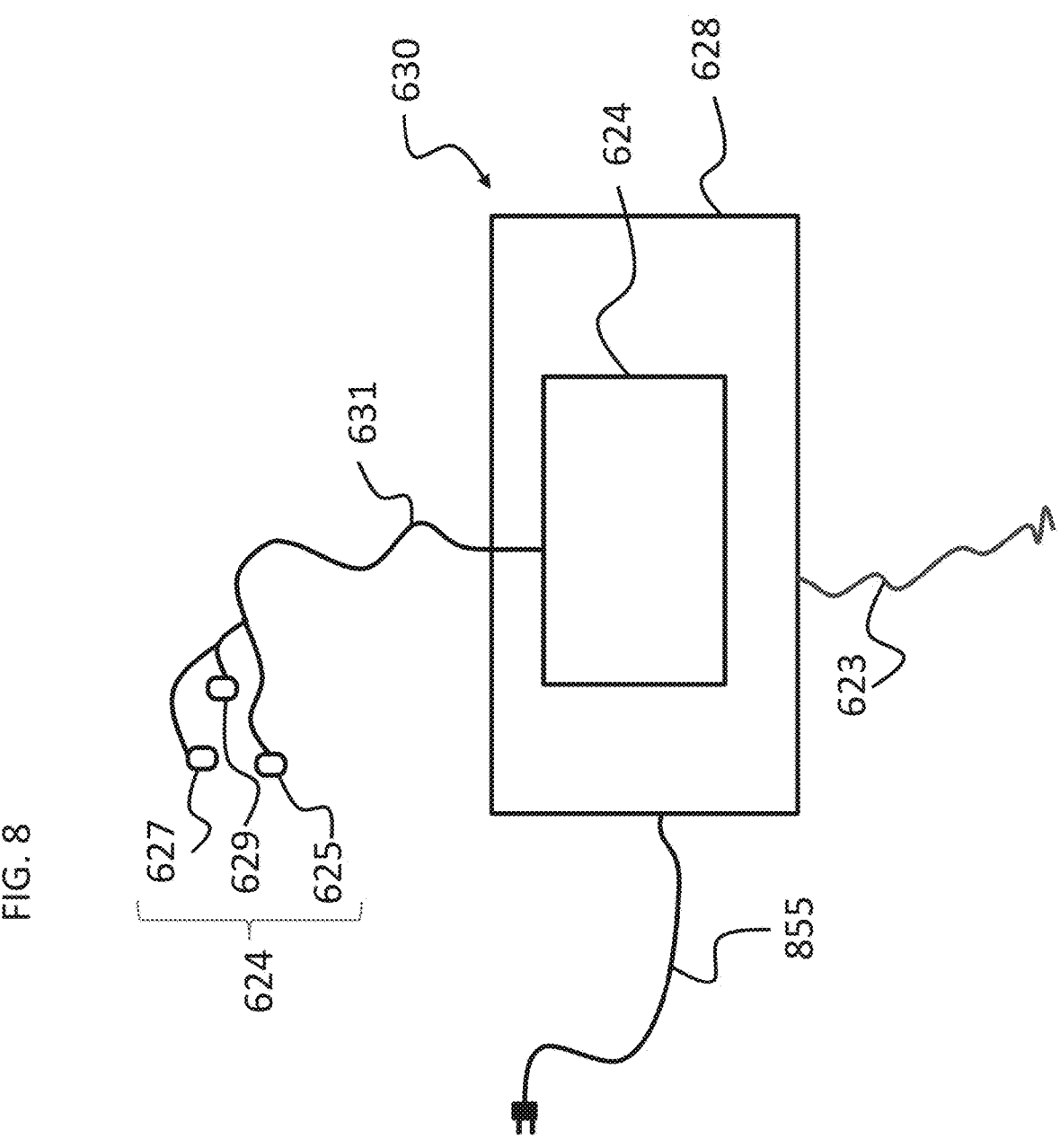

And with respect to the galvanic stimulator, FIG. 8 presents an exemplary embodiment of such. Here, galvanic stimulator 630 is configured to be powered by electricity from the standard utility electrical grid via conventional plug and electrical cord apparatus 855 (this can be a 120V or a 240 V power source). The power from the electrical grid can be manipulated into a utilitarian power source for the galvanic stimulation. By way of example only and not by way of limitation, insight housing 628 of the galvanic stimulator is an electrical stimulation generator device 624. Device 624 receives power from cord 855 and converts the power into a safe and utilitarian electrical supply to be provided to electrodes 624. By way of example only and not by way of limitation, device 624 can include one or more capacitors, including a capacitor bank and/or one or more transformers and/or one or more rectifiers, and device 624 can also include one or more batteries. Device 624 utilizes one or more of these components to convert the high-voltage power obtained via cord 855 into a usable electrical current to be applied by electrodes 624. Electrical lead 623 is in signal communication with the electrical stimulation generator device 624. Depending on the signals received via electrical leads 623 (or by a wireless communications link), the output current and/or voltage is adjusted (the current and/or voltage applied by the electrodes 624). Moreover, the output, more specifically, the timing of the output (beginning, length, ending) is also controlled based on the signals received from control device 620. In an exemplary embodiment, the signal received by electrical lead 623 is an electrical signal that controls a relay in the generator 624, where upon closing of the relay and/or opening of the relay, electrical current is permitted to flow or prevented to flow to the electrodes 624.

It is briefly noted that the cord 855 and the electrical leads 623 are not depicted as being connected, directly or indirectly, to the generator 624. This is for simplicity. In some exemplary embodiments, there is a direct connection between the cord 855 and the generation device 624. In some exemplary embodiments, this results in the exact voltage at the exact frequencies being delivered to generation device 624 that are conveyed by cord 855. In an alternate embodiment, there is a rectifier and/or a step down device between cord 855 and generator 624 (somewhat analogous to what is at the immediate location of a desktop computer—the electricity "inside the housing" is at a lower voltage almost immediately after entering the housing, if only for safety reasons). In an exemplary embodiment, cord 855 instead includes an AC to DC converter and/or a step down device, in a manner analogous to the power cord of a laptop computer by way of example. That is, the power that enters the housing is at a step down voltage and/or is at a DC current in a manner analogous to that which is the case for a laptop computer. Still, as will be described below, the rectifier and/or step down devices can be part of the generator 624.

In some embodiments, electrical leads 623 can extend directly to generator 624, and can control the operation of the generator at a high level. Conversely, electrical leads 623 can extend to relays that are located in between the generator and the leads 631 extending to electrodes 624, whereby the electrical leads 623 can control the opening in the closing of the relay, and thus control electrical output from the generator to the electrodes. Moreover, leads 623 can extend to a voltage and/or current limiter (e.g., voltage regulator, an adjustable voltage and/or current power supply can be controlled by leads 623) that is in between generator 624 and lead 631, and thus can receive commands or otherwise control signals from the control device 620, which enable the adjustments of the voltage and/or current based on the signals from the control device. Still, in some exemplary embodiments, these relays and/or limiters are part of the generator 624, and thus the control device 620 controls the operation of the generator at least partially, if not entirely.

It is briefly noted that in at least some exemplary embodiments, an alternating current is provided via electrical leads 631 to the electrodes 624. In some exemplary embodiments, a direct current is provided via electrical leads 631 to the electrodes 624. In some embodiments, the control device 620 is configured with a selector to select the type of electrical current to be applied by generator 624. In this regard, at least some exemplary embodiments are configured to output different types of electrical currents depending on the signals received from control device 620. By way of example only and not by way of limitation, with respect to some humans, they can be utilitarian value with respect to utilizing DC current, while in other embodiments, there can be utilitarian value with respect to utilizing AC current. Indeed, in an exemplary embodiment, for example, testing could begin with AC current, and if insufficient data is obtained utilizing the eye tracker, DC current could instead be used, or vice versa.

Irrespective of the types of currents that are outputted, at least some exemplary embodiments contemplate rectifying the AC current obtained via cord 655 to DC current. Thus, in some exemplary embodiments, generator 624 includes one or more rectifiers. Still further, in at least some exemplary embodiments, this is done even if alternating current will be utilized as the output of electrodes 624. Here, by way of example, generator 624 can include inverters that can invert the now DC current to AC current. That said, in some alternate embodiments, simple step down circuits are utilized to adjust the voltage of the power source received by cord 855. In some embodiments, frequency converters are utilized to change the frequency of the electrode from that received by cord 855 (e.g., to change the frequency from 50-60 Hz). Still, this can be where, for example, some embodiments have utilitarian value with respect to converting the receive power to DC current utilizing rectifiers, and then converting the DC power to AC current having a specific voltage and a specific frequency utilizing inverters, all of which can be included with generator 624. And this can be where there is utilitarian value with respect to having capacitors and/or batteries to store the converted DC power. In this regard, by way of example, power from the capacitors and/or batteries is utilized to provide electrical signals to electrodes 624, even though the ultimate power supply of the galvanic stimulator 630 is from the utility electrical grid.

Any device, system, and/or method of applying galvanic stimulation in a manner that is utilitarian to implement the teachings detailed herein, providing that the art enable such, can be utilized in at least some exemplary embodiments.

Figure 8A:
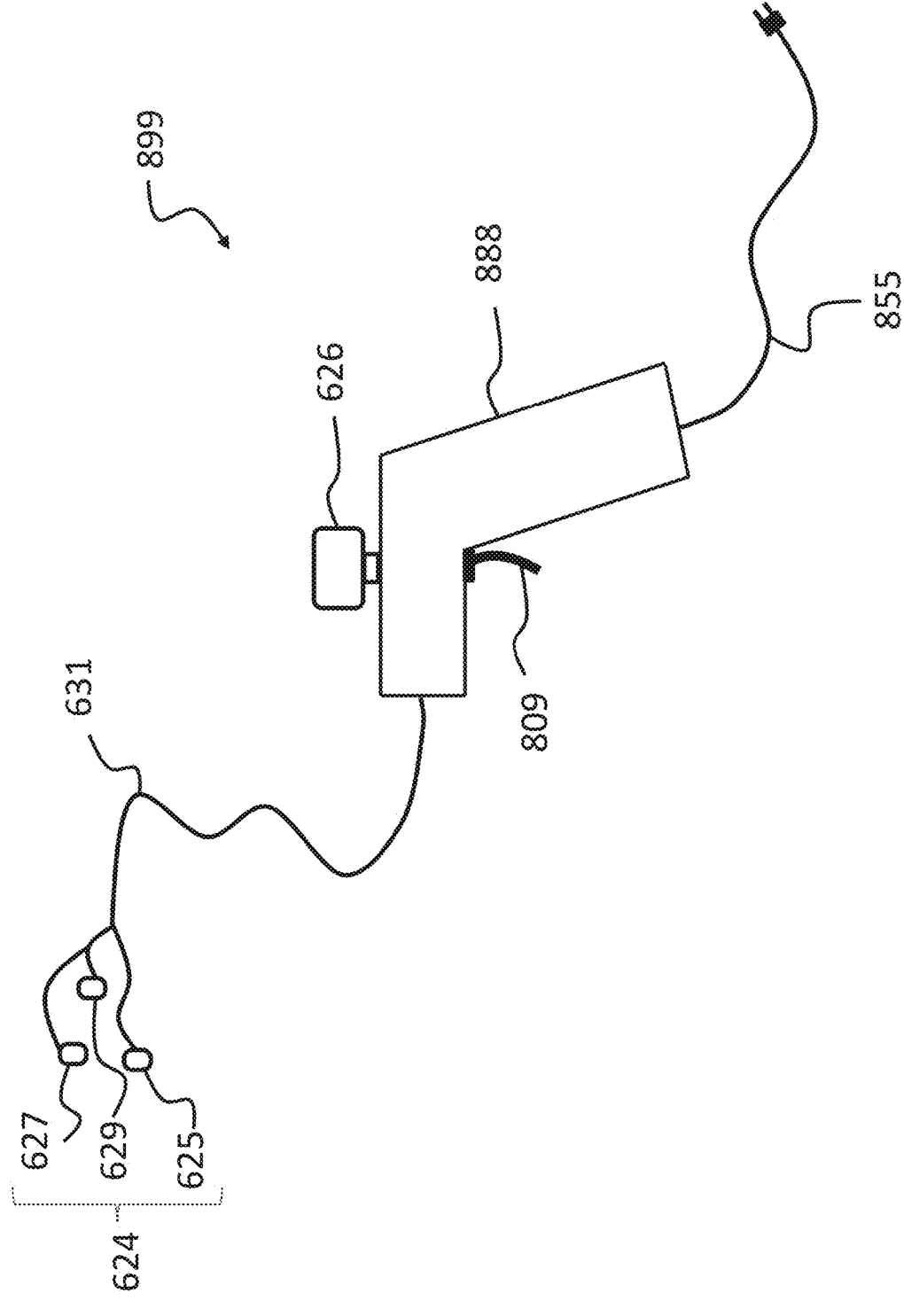

Embodiments of the control subsystem and the galvanic stimulator have been presented in terms of two discrete components. It is noted that in an alternative embodiment, the two components are combined into a single assembly. FIG. 8A presents an exemplary combined device 899 that is configured to provide the control and the galvanic stimulator in a single assembly. Here, the main component is a hand-held pistol grip like device 888 that includes a housing that contains one or more of the components detailed above. In this exemplary embodiment, utility power is obtained via cord 855 and provided to an internal generator device (not shown) inside the housing of the pistol grip like device 888, and operates in a manner and/or otherwise includes one or more of the above noted components of the generator device of the embodiment of the galvanic stimulator 630 detailed above. A rheostatic knob 626 is located at the top of the pistol grip like device 888, and is configured to enable digital adjustment of the amount of current or voltage via discrete adjustments of the knob 626, which discrete adjustments are mechanically controlled via a leaf spring detente system or the like. The adjustment of the knob change is a rheostat and thus changes the voltage that will be output by the device, where output is the output to the electrical leads 631 and then to the electrodes 624. Trigger 809 is configured to provide binary control of the combined device 899 by enabling a user to compress the trigger 809 with his or her index finger to initiate the delivery of electrical stimulation via the electrode 64 to the human. Trigger 809 can be connected to a relay or otherwise can open and/or close a mechanical switch between the internal generator and the electrical lead 631.

In at least some respects, the device 899 is a galvanic stimulator. Here, the control device is an integral part of the stimulator. Accordingly, in at least some exemplary embodiments, a galvanic stimulator can include the control apparatus, while in other embodiments, the control apparatus is separate from the galvanic stimulator.

Figure 8B:
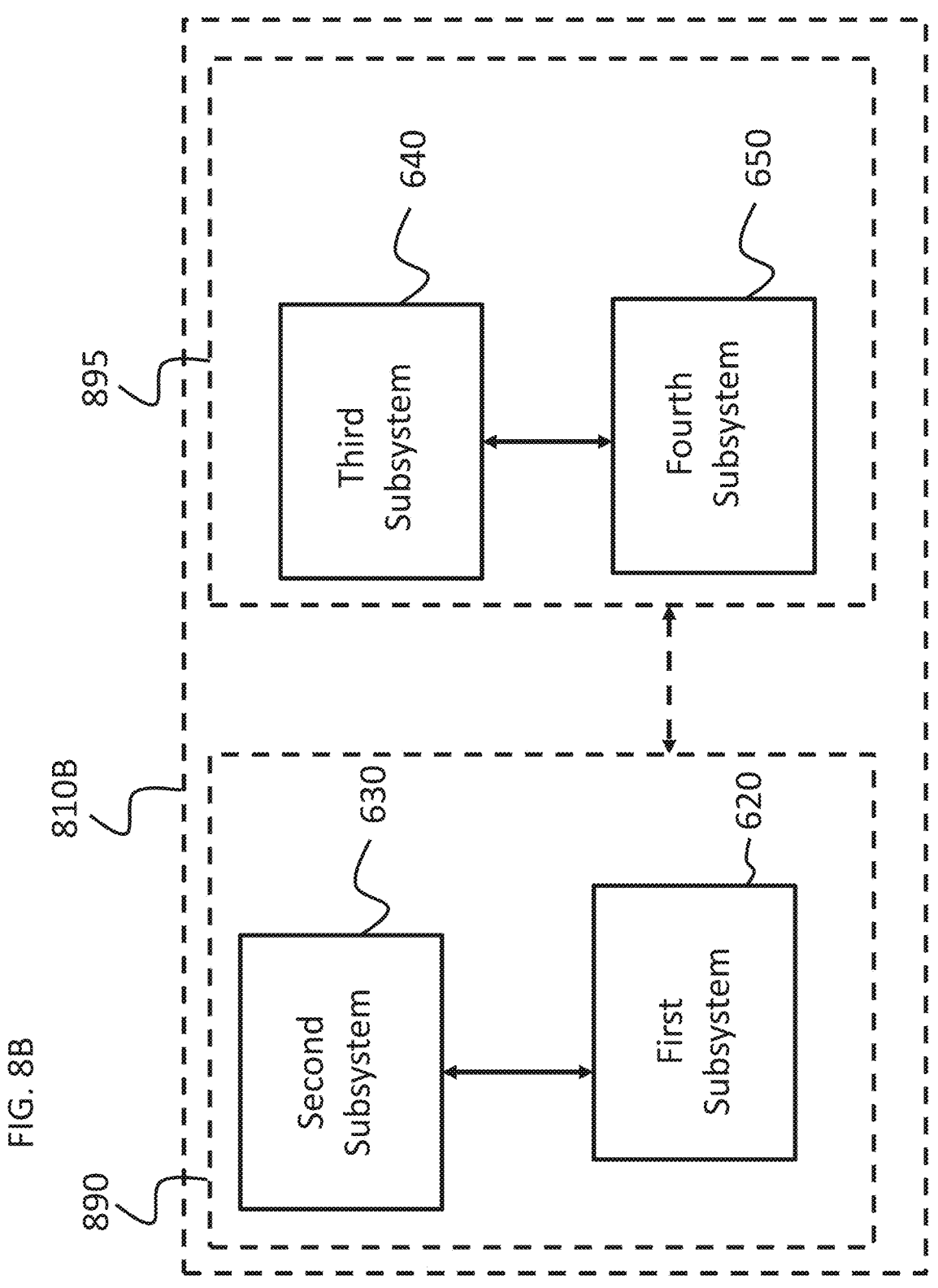
FIGS. 8B to 8C present some exemplary system diagrams.

And this leads to the concept presented in FIG. 8B, which depicts system 810B as including two subsystems: the stimulation subsystem 890, and the data collection subsystem 895. And while the control 620 and the galvanic stimulation device 630 are seen as bifurcated, it is to be understood that in some embodiments, such as those depicted in FIG. 8A, the stimulator and the control can be an integrated device.

FIG. 8B depicts the data collection subsystem 895 in potential signal communication with the data collection subsystem 895. In some embodiments, this may not be the case, and the system isolates the two subsystems. Thus, there may or may not be communication between the two subsystems, consistent with the embodiment detailed above.

Figure 9:
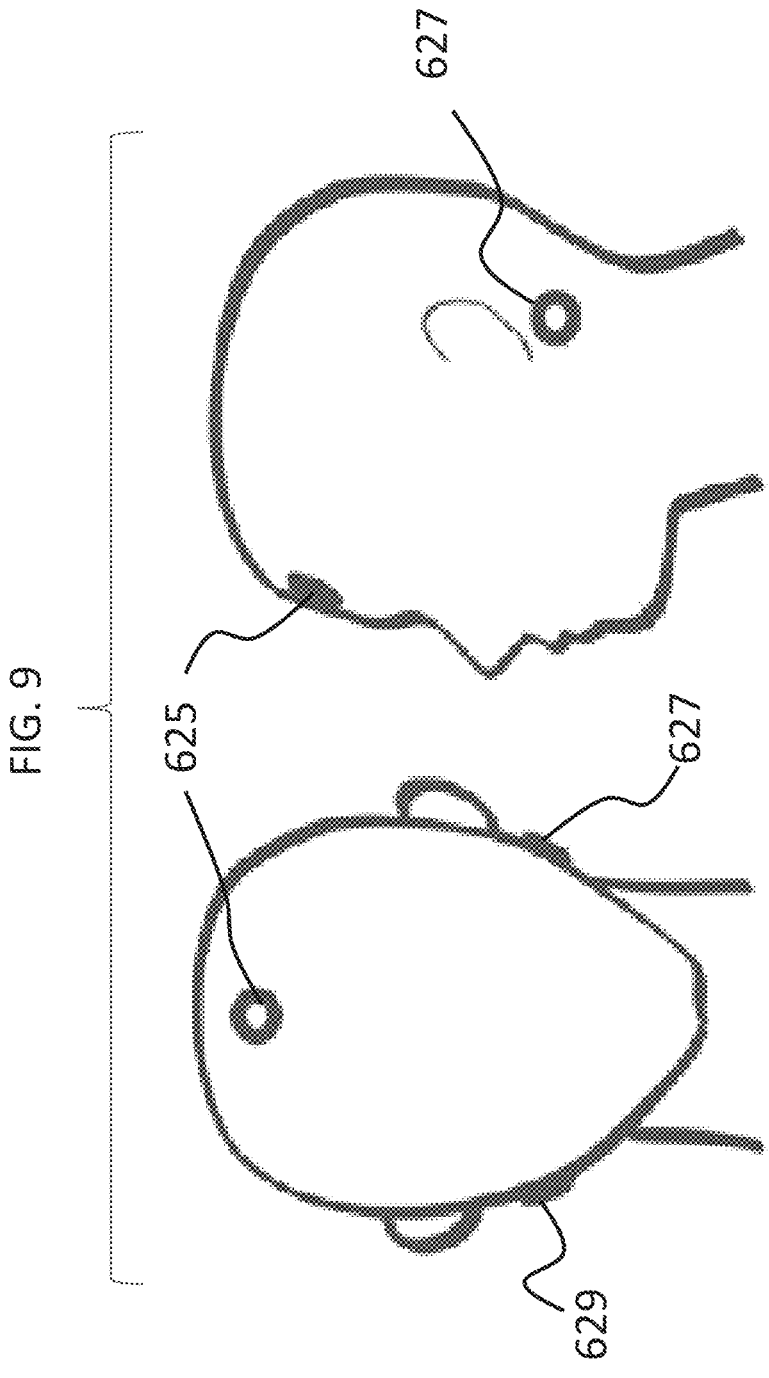
FIGS. 9 and 10 and 10A present some exemplary electrode placements.

In an exemplary embodiment, the galvanic stimulator includes three electrodes: electrodes 625, 627, and 629. These electrodes can be the EEG or EKG electrodes, except utilized to provide electrical stimulation to the recipient (which includes having at least one of the electrodes operate as a sink while one or more of the electrodes operate as a source). FIG. 9 presents an exemplary final electrode locational setup for galvanic stimulation according to an exemplary embodiment presented on a head meeting a 50 percentile human factors engineering male or female having a date of birth Mar. 15, 1971, in the United States of America and/or the nation now making up a part of the European Union as constituted on Mar. 15, 2021, and having lived in those geographic locations for at least 80% of that person's life, including 100% of the time between birth and 18 years of age. It is noted that the exemplary embodiment shown in FIG. 9 can also be for a tenth percentile to $90^{th}$ percentile human factors engineering males and/or females in one or more percentile increments therebetween in any range in one or more percentile increments (e.g., $34^{th}$ percentile, $89^{th}$ percentile, $44^{th}$ to $77^{th}$, etc.) being born 45 years before and/or 45 years after that date or any value or range of values therebetween in one year increments. It is also noted that the placement can be indicative of placement for human beings that are less than 20, 19, 18, 17, 16, 15, 14, 13, 12, 11, 10, 9, 8, 7, 6, 5, 4, 3, 2, or 1 years of age, meeting the physical characterizations of any one or more of the human factors engineering types of humans detailed above. In this regard, at least some exemplary embodiments specifically include the utilizations of the teachings detailed herein on adolescence and/or prepubescent children and/or infants, and methods include implanting the methods herein with such.

And it is noted that the embodiment presented in FIG. 9 is an arrangement where both sides of the hearing system are tested in one sitting without adjusting the electrodes. Here, with respect to a view looking at human, electrodes 625 and 629 are utilized to provide galvanic stimulation to the vestibular system on the left side (which would be the human's right side vestibular system), and the electrodes 625 and 627 are utilized to provide galvanic stimulation to the vestibular system on the right side (which would be the human's left side vestibular system). The galvanic stimulator would be controlled so that electrical current flows between electrode 625 and electrode 629 during one period of time, where, the eye tracker can be utilized to detect eye movements or otherwise track eye movements, and then the galvanic stimulator is utilized or otherwise controlled so that electrical current flows between electrode 625 and electrode 627 during another period of time separate from the aforementioned period of time, where the eye tracker can be utilized to detect eye movements or otherwise track eye movements for that particular stimulation as opposed to the other stimulation. There is thus utilitarian value with respect to a method of attaching electrodes at the beginning of the testing and not adjusting or otherwise attaching electrodes at other locations during the testing. Utilizing the three electrodes for example can achieve this utilitarian aspect of the teachings. Of course, in some embodiments, only two electrodes are included in the galvanic stimulator, and the two electrodes are utilized to provide galvanic stimulation to the vestibular system on one side of the human, and then at least one of the electrodes is removed and then attached to the human on the other side of the head and those electrodes are again used to provide galvanic stimulation, except to the vestibular system on the other side of the head.

And embodiments can use monopolar and/or bipolar stimulation. In the embodiment shown in FIG. 9 for example, if an electrode is attached to only one side (or one electrode is not used/deactivated) this is monopolar stimulation and mono oral stimulation (where only one side is tested at a time). That said, in some embodiments, the electrodes can be placed and/or used for bipolar and/or binaural stimulation, and thus the arrangement seen in FIG.

9 can be utilized for bipolar and/or binaural stimulation. Still, there is utilitarian value in at least some exemplary embodiments to discreetly testing the vestibular system that is a candidate for the implantation relative to the opposite vestibular system, and if both are candidates, to discreetly testing each vestibular system.

Figures 10, 10A:
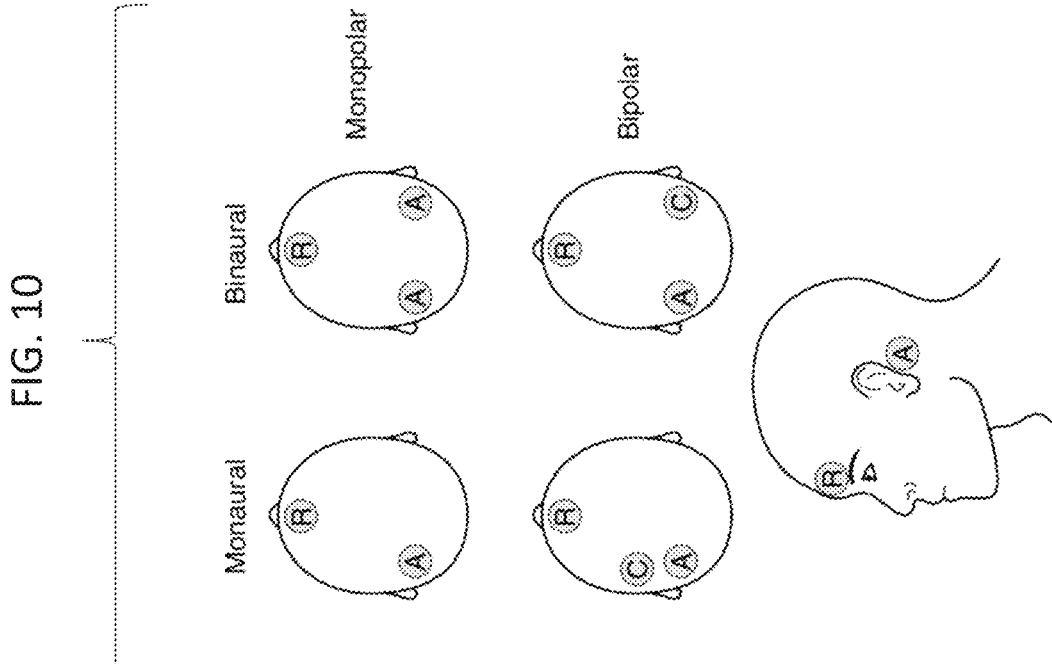

In any event, FIG. 10 presents an exemplary schematic presenting some exemplary concepts associated with electro-placement. The left column depicts a monoaural stimulation regime, and the right column depicts a binaural stimulation regime. And it is noted that even if electrodes are placed on both sides of the human, monoaural stimulation can still be provided by simply not energizing or otherwise utilizing the electrode on one side of the head.

FIG. 10 also depicts concepts for bipolar stimulation, and as can be seen, the arrangement of FIG. 9 can be utilized to achieve such. Still, in an exemplary embodiment, by placing two electrodes on one side, such as seen with respect to electrodes "C" and "A" in FIG. 10, which can correspond respectively to electrodes 627 and 629, bipolar stimulation can be achieved in a monoaural arrangement. If using bipolar stimulation, electrode C would be located proximate electrode A.

It is noted that tripolar stimulation, and beyond, and otherwise multipolar stimulation can be utilized in some embodiments. Accordingly, embodiments of the galvanic stimulator can include two, three, four, five, six, seven, eight, nine and/or 10 or more electrodes.

Electrode configurations that are usable for galvanic vestibular stimulation according to at least some exemplary embodiments are divided in to monopolar or bipolar electrodes and the electrode placement can produce an ipsilateral or bilaterally stimulation. Embodiments thus include any one or more of the utilization of the electrodes to achieve such, and also include any device and/or system to enable such.

As noted above, in some embodiments, the electrodes are electrodes for EEG and/or EKG monitors. Thus, in an exemplary embodiment, the electrodes of the galvanic stimulator are completely supercutaneous. Still, in an alternate embodiment, the electrodes could be transcutaneous. In an exemplary embodiment, the electrodes could have micropins made out of conductive material that will pierce the surface of the skin and a minor manner, but will thus increase the electrical conductivity. This would be a limited invasive arrangement as opposed to the completely supercutaneous arrangement. In an exemplary embodiment, the electrodes do not extend more than 1, 0.9, 0.8, 0.7, 0.6, 0.5, 0.4, 0.3, 0.2, or 0.1 mm, or any value or range of values therebetween in 0.01 mm increments into the skin.

Any number of electrodes and/or types of electrodes that can be utilized to implement the teachings detailed herein can be utilized in at least some exemplary embodiments, providing that the art enable such.

Figure 11:
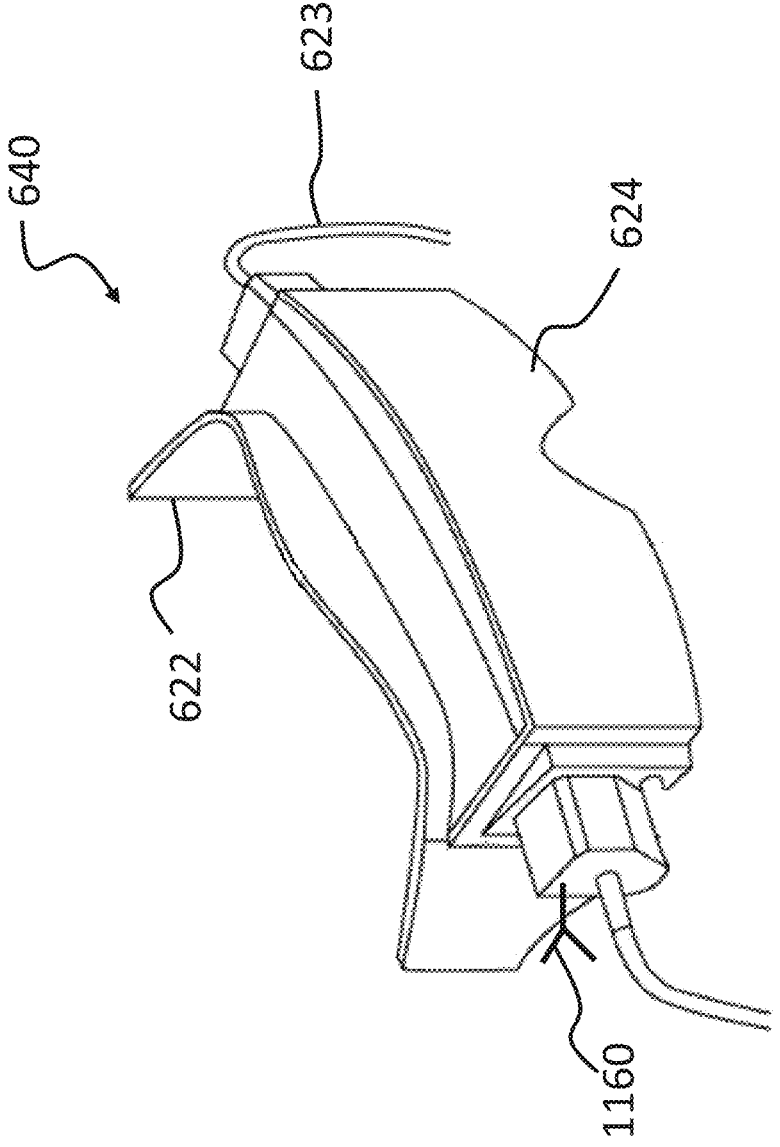
FIGS. 11, 12 and 13 present schematics of some exemplary embodiments.

FIG. 11 presents an exemplary eye tracking device 640, which can correspond to the eye tracking subsystem 640 of system 610. Here, the eye tracking device includes a forehead interface 622 that is ergonomically configured to interface with the forehead of a human, including the aforementioned human factors engineering humans detailed above. In an exemplary embodiment, the forehead interface is made out of a memory material that provides a slight compression on to the sides of the human's head, thus holding the eye tracking subsystem in place. That said, in an alternate embodiment, an adjustable nylon strap or some other equivalent strap is attached to the respective and portions of the interface 622, which adjustable strap is configured to extend around the back of the head and, upon tightening of the strap, secure the eye tracking subsystem 640 at the appropriate place on the head of the human so that the movement of the eyes can be tracked or otherwise electronically recorded/electronically captured.

In an exemplary embodiment, subassembly 640 is in the form of a helmet, where the portion that goes over the eyes can be raised or lowered, analogous to a night vision goggles system attached to a military helmet. Alternatively, the portion that goes over the eyes can be positionally fixed relative to the helmet. Further, in an exemplary embodiment, instead of a helmet, a semirigid frame, such as the interior portion of a riding helmet or a bicycle helmet that is adjustable is utilized to support the portion that goes over the eyes, which can be adjustable to fit the head, and where the portion that goes of the eyes can be positionally fixed or movable relative to the remainder of the frame.

It is also noted that in some embodiments, head steadying devices/frames can be used, where the eye tracking device may or may not be hard-mounted thereto.

Any device, system, and/or method that can enable the portion that extends in front of the eyes or otherwise over the eyes to be supported on the head of a human in a utilitarian manner can be utilized in at least some exemplary embodiments. As seen, the eye tracking device 640 includes a portion 624 which goes in front of/over the eyes. This portion includes at least partially sensors that are configured to track the movement of the eyes. In an exemplary embodiment, tracking sensor 624 is a standard eye tracking device. In an exemplary embodiment, the sensors are nonintrusive sensors. In an exemplary embodiment, the tracking sensor 624 includes a source of invisible near infrared and/or infrared light configured to eliminate the pupil and configured to establish a reflection that is generated on the cornea of a normal eye, or otherwise the eye of any one or more of the aforementioned human factors engineering humans. The tracking sensor 624 further includes a camera, which can be an infrared camera that captures this reflection that is generated. In at least some exemplary embodiments, the output of this camera is outputted via electrical leads 623 which extend back to the control device 620. Accordingly, in at least some exemplary embodiments, the output of the camera system (one or more cameras), or other light capture devices, is the output of the eye tracking subsystem 640. Alternatively, and/or in addition to this, the eye tracking subsystem 640 can include some amounts of processing capabilities, such as an onboard processor, that can evaluate the light captured by the camera, more accurately, can evaluate the signal outputted by the camera, and evaluate that to evaluate whether or not the eye is moving and/or the amounts that the eye is moving and/or how the eye is moving, etc. Conversely, in some embodiments, alternatively and/or in addition to this, this can be done by the control device 620 and/or the analytical subsystem 650 detailed above, which again can be a personal computer.

With respect to the control device, 620, the signals from the eye tracker 640 are provided to the processor suite 628, where logic circuitry, such as a microprocessor thereof, or computer chips, etc., analyze the signal utilizing software and/or firmware. In this exemplary embodiment, control device 620 provides output to the user via the display 622. In an exemplary embodiment, the output can be a relatively sophisticated display of the recipient's eyes upon which is superimposed data indicative of eye movements. In an exemplary embodiment, the output can be any data associated with eye tracking technology that has utilitarian value with respect to implementing the teachings detailed herein. More on this in a moment.

In an exemplary embodiment, one part of the system 610, whether that be the eye tracking subsystem 640 and/or the control subsystem 620 and/or the analytical subsystem 650, can be configured to delimit the center of the pupil from the output of the camera or other light capture device, deduce eye rotation by way of example, and determine gaze direction by way of example. In some embodiments, the fact that there is eye rotation is determined and that is the output of whatever subsystem is utilized. In some embodiments, the amount of eye rotation is determined and that is the output. In an exemplary embodiment, the output is "pass/fail," where whatever subsystem at issue includes predetermined logic or otherwise in includes software or some form of logic tree that can analyze the output from the camera or other light capture device and determine a magnitude or otherwise extrapolated magnitude of movement and determine a otherwise provided output that "sufficient" eye movement has occurred.

In an exemplary embodiment, whatever subsystem is utilized to implement the eye tracking, such subsystem can include mathematical algorithms in software and/or firmware and/or hardware, such as logic circuits or otherwise computer chips that are programmed with to execute such mathematical algorithms, to calculate the eye position and/or the point of gaze and/or eye movements. The results of these calculations can be data that is provided to an eye tracking software package that processes this data. Again, all of this can be embodied in the eye tracking subsystem, while in other embodiments, this is embodied in the control subsystem and/or the analytical subsystem.

In an exemplary embodiment, at least one of the subsystems detailed herein is configured to provide calibration to address the potential lack of alignment between the optical and visual axes. This can be done automatically or manually. The point is that the system 610 is configured to do so or otherwise enable such to be done. In an exemplary embodiment, the system is configured to provide correction to the overall system during the calibration process to enable the positions of the pupil and the gaze to align with each other in a utilitarian manner.

In an exemplary embodiment, at least one of the subsystems detailed herein is configured to calculate the gaze point, although in other embodiments, this can be done manually and entered into the system. In an exemplary embodiment, the gaze point is calculated or otherwise determined by one or more of the subsystems and the system includes software and/or hardware and/or firmware to execute such. In an exemplary embodiment, a commercial off-the-shelf eye tracking system can be utilized, which can correspond to the eye tracker 640 in some embodiments.

In at least some embodiments, videonystagmography is utilized to evaluate eye torsion (e.g., otoliths) and/or translation (e.g., the phenomenon presented by the semicircular canals) and/or VEMPs, where the ocular VEMPs (utricle) and/or cervical VEMPs (saccule) is evaluated. And of course, it is to be understood that the evaluation can vary depending on the physiological recording/data set. Some eye movements will be evaluated instead of others if the eye tracking device provides input indicative of that type of eye movement.

In an exemplary embodiment, the eye tracking subsystem or other pertinent subsystem is configured to calculate the gaze point, and presents data associated therewith in the form of an XY coordinate. This coordinate can indicate where the human is looking within the eye tracking system (or at a general screen—it is noted that while the embodiments detailed herein are directed towards an arrangement that prevents the user from seeing beyond a few inches from his or her eyes, in an alternative embodiment, the portion 624 that extends in front of the eyes or over the eyes permits the user to see beyond such. Moreover, in some embodiments, the eye tracking devices are located to the side, and there is nothing per se directly in front of the eyes). In some embodiments, coordinates are outputted according to a frame rate of speed/tracking speed. This can be the output that is provided via electrical leads 623 (or via a wireless link), or can be developed by the control device and/or the analytical device.

Embodiments include a system that is configured to identify fixations and/or saccades automatically (including when prompted by a user/healthcare professional). In an exemplary embodiment, software can be included in the eye tracking subsystem 640 and/or in the analytical subsystem 650 and/or in the control subsystem 620 that process data output from the cameras or other light capture devices, and can identify the fixations and/or the saccades utilizing the software (or other comparable devices, such as firmware or logic circuits). And a graphical representation of the fixations can be presented on the output screen of the pertinent device, such as, for example, the presentation of dots with sizes corresponding to the duration of the movement. Lines can be presented on a display screen that connect the fixation dots so as to represent saccades, if desired. This display screen can be the display screen 622 on the control subassembly 620 and/or can be the display screen of the laptop computer or otherwise the analytical subsystem, and, in some embodiments, can be a display screen that is actually a part of the eye tracking device.

In some exemplary embodiments, the system detailed herein is configured to provide static and/or animated representations that provide an indicia of eye tracking and gaze tracking. Various metrics can be outputted to a user and/or various visualizations can be outputted to a user to enable the user to inspect the collected data. That said, in an exemplary embodiment, the analysis of the data can be automated or semiautomated. Predetermined values and/or ranges can be inputted into the system before hand, which values and/or rages can be based on empirical data and/or statistically significant data, such as that obtained for any one or more of the aforementioned human factors engineering humans, and the system can compare the obtained results utilizing the eye tracker to the predetermined values and/or ranges, to determine whether or not eye movement has taken place and/or the amount of eye movement that has taken place. And in this regard, the predetermined values and/or ranges can be correlated to values and/or ranges that are indicative of a sufficient vestibular response that are indicative of a vestibular implant having utilitarian value to that particular human.

More specifically, the eye tracker 640 is utilized to detect or otherwise capture eye movements. In an exemplary embodiment, this is done in conjunction with the vestibular stimulation utilizing the galvanic stimulator detailed above. That is, the teachings detailed herein are directed towards correlating eye-movement with galvanic stimulation to a human, which galvanic stimulation will result in eye movements in an at least partially functioning vestibular system, or otherwise a vestibular system that includes at least a partially functioning neural system. If eye-movement, or otherwise sufficient eye-movement, is detected in correlation to the galvanic stimulation, a determination can be made that the vestibular system of the human will support the utilitarian value of a vestibular implant. Conversely, if eye-movement or otherwise sufficient eye-movement is not detected in correlation to the galvanic stimulation, a determination can be made that the vestibular system of the human will not support utilitarian value of a vestibular implant. Accordingly, the predetermined values and/or ranges can be those that have been predetermined to correspond to a sufficient vestibular response. Conversely, the predetermined values and/or ranges can be simply threshold that are statistically indicative of reactions that are not random occurrences or otherwise "noise." Put another way, the algorithms utilized by the system can be such that the output of the system is simply a determination that the eyes have moved in a statistically meaningful manner relative to a stimulation applied to the human. Whether that is sufficient to determine that the human can be a candidate for a vestibular implant could be made independently of such.

But to be clear, embodiments are directed to, based on utilitarian properties of the GVS, providing utilitarian pre-operative information to a user, whether in raw form, or in processed, determinative form, for and/or of an evaluation of a human is a statistically viable candidate (or not) for a vestibular implant.

Figure 12:
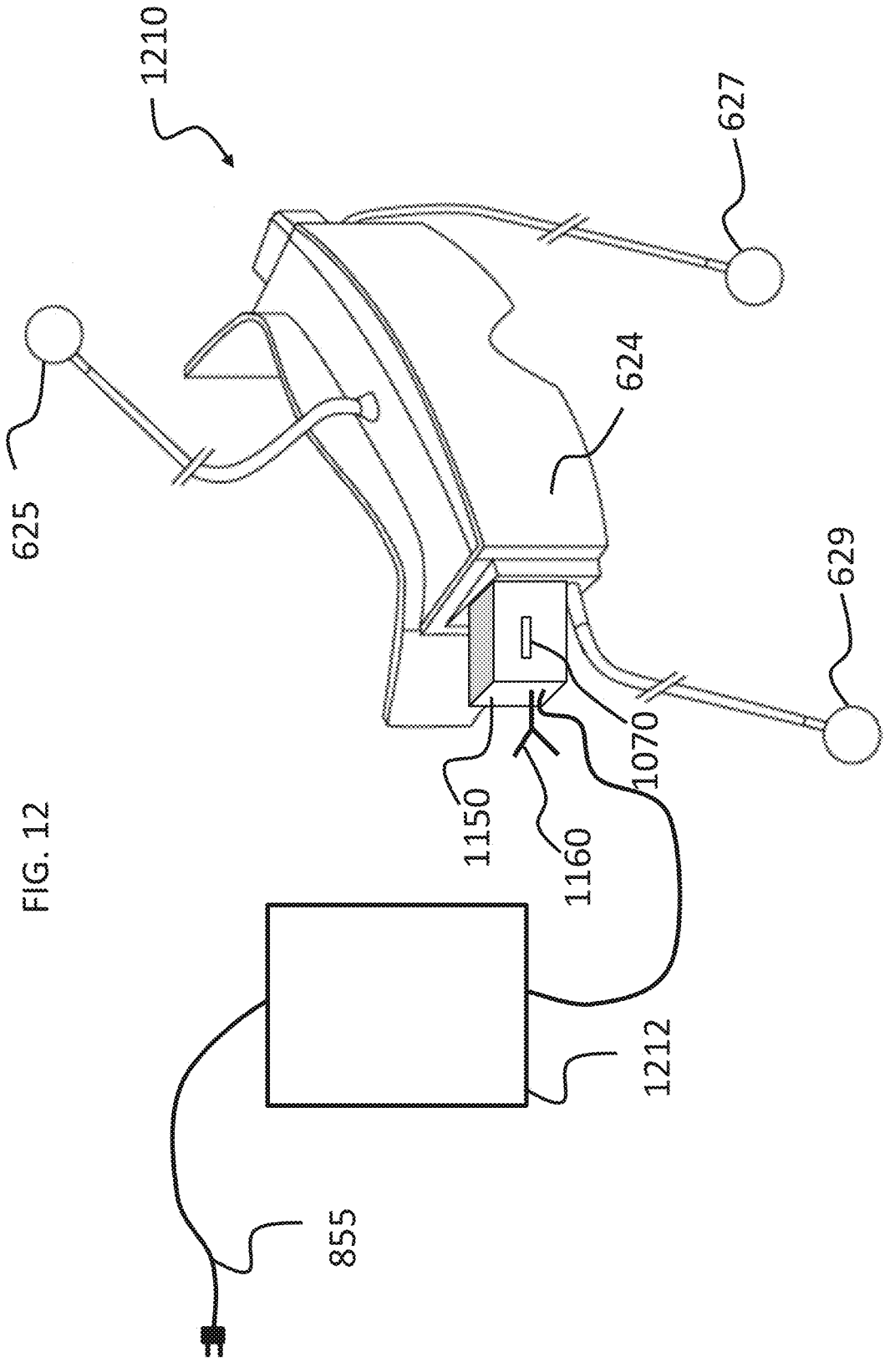

It is briefly noted that some exemplary embodiments can include a unified assembly where all of the various sub systems detailed herein are part of a single assembly. FIG. 12 presents an exemplary embodiment of such, where an integrated clinical vestibular implant suitability evaluation system 1210 is presented. Here, it can be seen that the electrodes are integrated with the eye tracking device in general, and/or otherwise supported by the overall arrangement that includes the portion 624 that goes in front of the eyes and includes the sensors or cameras or otherwise light capture devices that enable the underlying data to be obtained for eye tracking. The assembly 1210 includes a housing 1150 that includes any one or more or all of the aforementioned components that enable the system 610 detailed above, potentially a miniaturized form. Still, consistent with the teachings detailed above, the assembly 1210 can include an AC to DC converter and/or a step down circuit in housing 1212, one end of which is configured with a power cord 855 configured to interface with standard grid power, the other end of which is configured to output a current, such as DC current, in a manner analogous to a power supply to a laptop computer. And in this regard, the "jack" supported by housing 1150 that receives the power cord from housing 1212 can be that corresponding to the "jack" of a laptop computer for example. Moreover, one or more of the stimulation current generators of the galvanic stimulator can be located in the housing 1212. This can have utilitarian value with respect to decreasing the weight of the head worn component, and otherwise ensuring that the high-voltage alternating current is kept away from the humans head (housing 1212 could be connected to housing 1150 by a 3 foot or 4 foot or 5 foot power cord, enabling housing 1212 to be placed on the floor or on a table, etc. Indeed, in an exemplary embodiment, the component that attaches to housing 1150 can be a standard power supply for a laptop computer. And corollary to this, in an exemplary embodiment, the assembly 1210 can be completely isolated from the high-voltage alternating current, such as, for example, utilizing a battery supply, such as a battery supply for a laptop computer.

Thus, FIG. 12 can represent a full-system galvanic stimulator and video-nystagmography device combined in the same assembly.

Figure 8C:
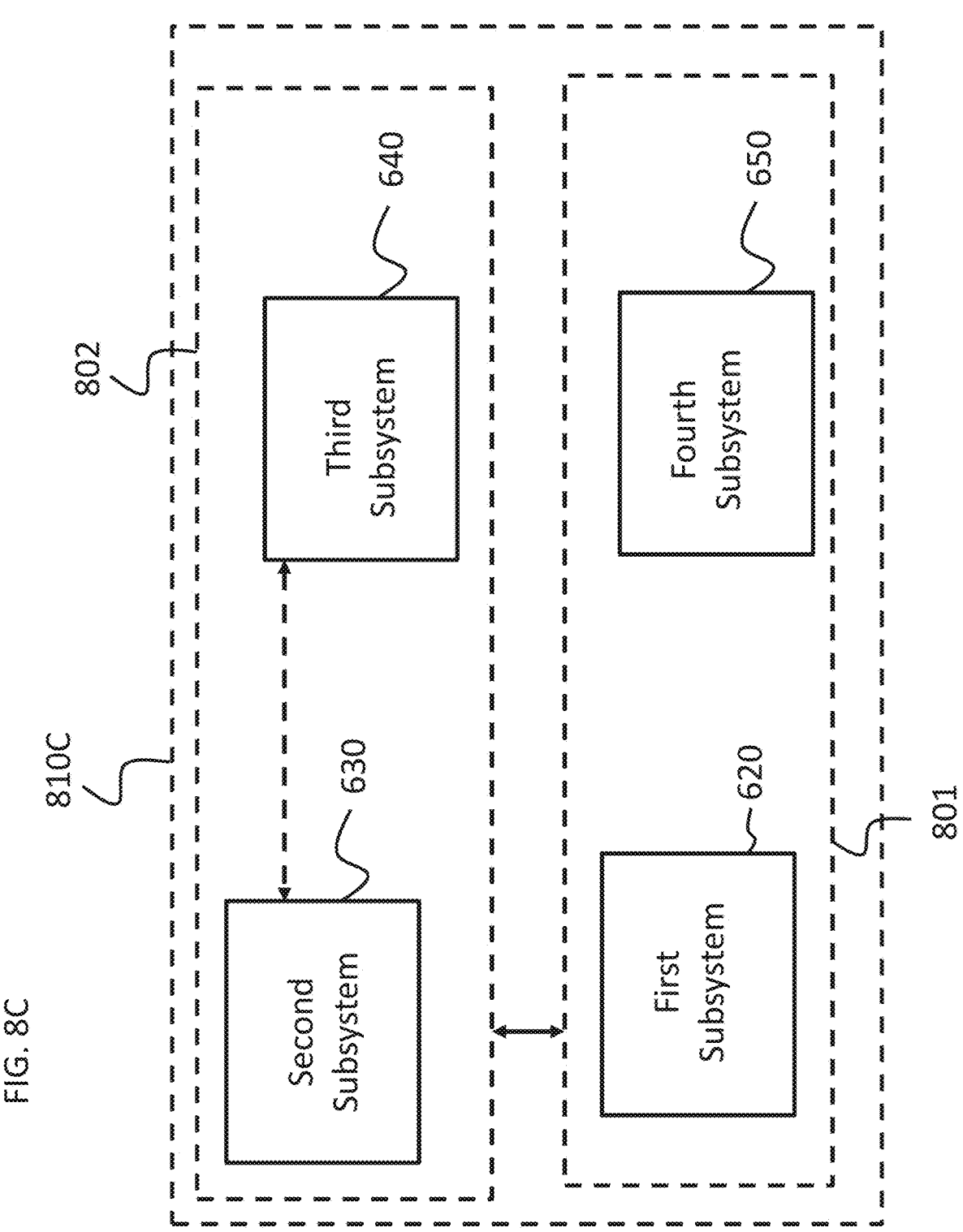
Figure 13:
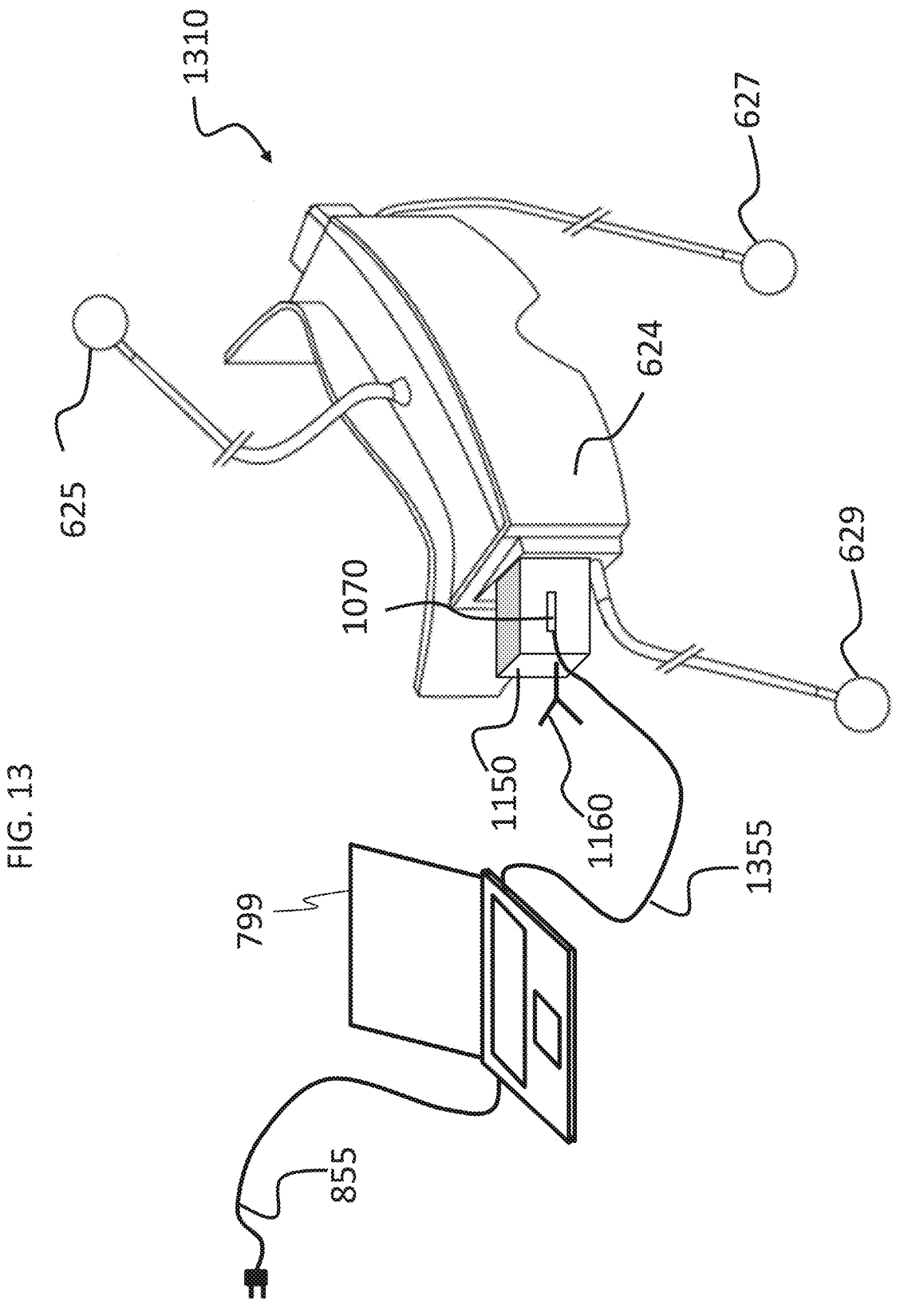

And this leads to the embodiment presented in FIG. 13, where there is an exemplary system 1310 where power supplied to the headset is supplied via a USB port of the laptop computer 799 and a USB port 1070 of the headset. Here, inside housing 1150, is a stimulation generator that is configured to operate utilizing the currents and voltages output by a USB port of the laptop. Corollary to this is that cable 1355 can also provide data to and/or from the headset. This can enable laptop 799 to be the control subsystem and/or the analytical subsystem, whereas the galvanic stimulator and the eye tracker are part of the headset. This can thus correspond to the system 810C presented in FIG. 8C, where subsystem 801 corresponds to the laptop computer 799, and subsystem 802 corresponds to the galvanic stimulator and eye tracking device (or at least portions thereof). In it can thus be seen that portions of the various subsystems can be moved to other subsystem is that in at least some exemplary embodiments.

But referring back to FIG. 12, it is noted that in an exemplary embodiment, housing 1212 can be replaced by the pistol grip 888 detailed above, and the associated hardware and components supported thereby. Accordingly, in an exemplary embodiment, some or all of the components of assembly 899, save for the electrodes 624, and possibly replacing electrical leads 631 with the aforementioned power cable to attach to housing 1150, can correspond to the housing 1212 and the power cable 855, and the power cable extending to housing 1150. That is, in an exemplary embodiment, the output of the pistol grip 888 can be provided to housing 1150 (and a separate output to provide current to power the eye tracking device—in an alternate embodiment, a separate power supply can be utilized to provide power to housing 1150—in this regard, the components of assembly 899 under discussion could instead be an add on to the apparatus shown in FIG. 12, where lead 631 is removably electrically connected to housing 1150), and thus to the electrodes of the headset.

Still with respect to both FIGS. 12 and 13, as noted above, the housing 1150 of the headset includes a USB port 1070. In an exemplary embodiment, such as the embodiment of FIG. 12, a USB memory stick is attached to the USB port 1070, and the output of the eye tracking system is provided to the memory stick via the USB port 1070. Alternatively, the USB port 1070 can be directly connected to a laptop computer, such as shown in FIG. 13, where that arrangement can also be utilized in the embodiment of FIG. 12, where, for example, the laptop 799 is utilized to receive the data from the eye tracking device, and in some embodiments, can be the control of the system. Still, in some exemplary embodiments, the data, whatever it is, can be stored in the USB memory stick and/or in the memory of the laptop computer, for analysis in the case of a memory stick, the memory stick can be provided to a laptop or a desktop computer, and the information transferred to the memory thereof, where it can be analyzed, by the computer and/or by a user of the computer.

It is further noted that the embodiments of FIGS. 11, 12 and 13 can be shown to include an antenna 1160 of a wireless link, which wireless link enables wireless communication from the headset to a location away from the headset, such as, for example, a laptop computer by a Bluetooth link and/or via a smart phone or any other device. In at least some exemplary embodiments, the data from the eye tracker is transmitted by the wireless system thereof so that the data can be analyzed. Moreover, in at least some exemplary embodiments, the wireless link can be utilized to control the eye tracker and/or the galvanic stimulator, depending on the embodiment.

In view of the above, it can be seen that in an exemplary embodiment, there is a system comprising a galvanic stimulator and an eye tracking device configured to capture data indicative of eye movement, wherein the system is a clinical vestibular implant's suitability evaluation system. In an exemplary embodiment, this can correspond any one or more of the embodiments detailed above and/or variations thereof or other arrangements, providing that there is a galvanic stimulator and an eye tracking device where, collectively, the system is a clinical vestibular implant suitability evaluation system. The eye tracking device could simply be a device that is configured with a camera that can capture eye movements and output a signal indicative of the eye movements. The eye tracking device can be a full-blown eye tracking system in some other embodiments. In an exemplary embodiment, the system is established by a head-worn system (as distinct from the mere fact that the eye tracking device is worn on the head—here, this requires that at least substantial portions of the system are part of a head worn apparatus). In an exemplary embodiment, the system is configured to evoke a vestibular reflex, such as that which results from utilization of the galvanic stimulator, in a human with at least a partially functioning neural system of the human's vestibular system. This can be accomplished with the galvanic stimulator detailed above, which, when the pertinent electrodes are attached to the surface of the human skin at locations that have utilitarian value, and a current is applied in a utilitarian manner via those electrodes, can evoke a vestibular reflex.

In an exemplary embodiment, the eye tracking device includes a videonystagmography recording system. The output of this recording system can be provided to a user of the system and/or can be evaluated utilizing a processing program and/or logic circuitry of any one or more of the devices detailed herein to determine the suitability of the human under testing for a clinical vestibular implant.

In an exemplary embodiment, the system includes a computing apparatus configured analyze eye tracking data generated by the eye tracking device and provide output indicative of the analysis. This output is not the raw output from the eye cameras, but instead is processed data or otherwise data that is the result of an evaluation of the output from the eye cameras (either direct output or processed output) and/or data that is the result of an evaluation of the output from the eye tracking device. This computing system can be part of an eye tracking system of which the eye tracking device is apart, or can be a separate part of the system, such as another subsystem. Conversely, embodiments of the system under discussion can be a system where the output of the system is simply the raw data from the eye tracking device.

Still, at least some exemplary embodiments of the systems detailed herein include a computing apparatus. In an exemplary embodiment, the included computing apparatus is configured to analyze eye tracking data generated by the eye tracking device and, based on the analysis, automatically provide an indication of whether a vestibular implant would be utilitarian for a human stimulated by the galvanic stimulator and who's eyes are tracked by the eye tracking device. This is contrasted to a system where the output is simply data indicative of eye movement, or a healthcare professional or the like evaluates the eye movement to determine the utilitarian nature of a vestibular implant for the human under testing.

In an exemplary embodiment, the system includes a vestibular evoked myogenic potentials (VEMPs) sub-system configured to record vestibulo-ocular and/or vestibulo-spinal reflex(es). This subsystem can include the eye tracking device detailed above.

In this regard, in an exemplary embodiment, the systems detailed herein look for a vestibular evoked myogenic response to evaluate vestibulo-ocular and/or vestibulo-spinal reflexe(s) or otherwise to identify the occurrence of such reflexes, where the evaluation and or the occurrence is indicative of a vestibular system having sufficient functionality to render a this tubular implant utilitarian.

And as seen above, the system can include a set of electrodes for galvanic stimulation, which can be part of the galvanic stimulator as a whole or can be readily releasably attached to the galvanic stimulator.

Embodiments detailed above have been presented in terms of in some instances, a unitary controller that controls the galvanic stimulator and the eye tracking device. In an exemplary embodiment, such as where, for example, the control device is a laptop computer with software thereon that is written to execute one or more of the method actions detailed herein, upon initiation of testing, the galvanic stimulator can be controlled by the software on the laptop so that a stimulation command is sent to the galvanic stimulator by the laptop, which stimulation command control the galvanic stimulator to apply electrical stimulation to the human that, in a statistically significant manner, is likely to evoke a vestibulo-occular response that can be detected when the stimulation is applied to a vestibular system that has an at least partially functioning nervous system.

Figure 13A:
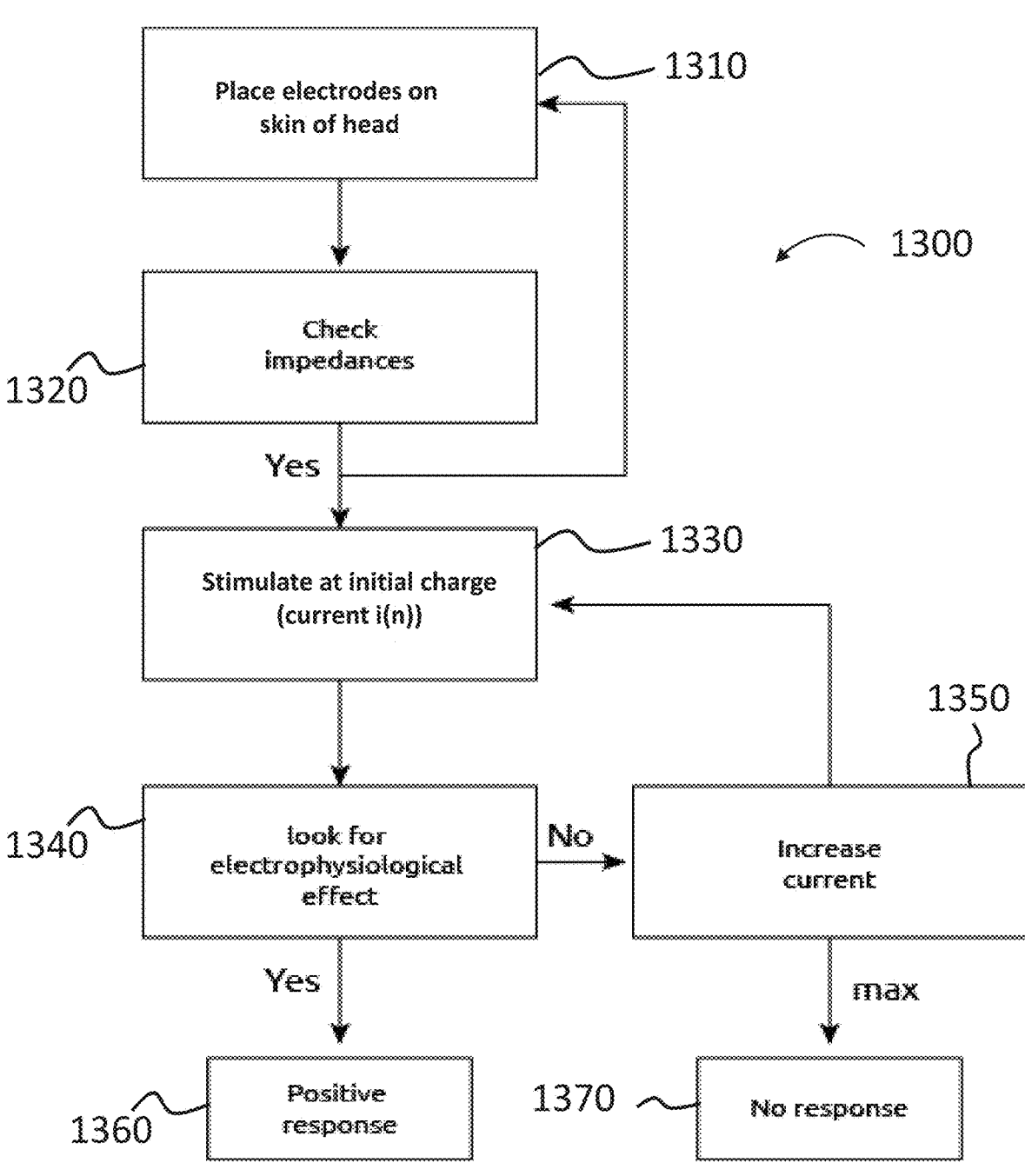

FIG. 13A presents an exemplary algorithm for an exemplary method, method 1300, of using one or more of the devices disclosed herein. In an exemplary embodiment, this can correspond to the utilization of the system 1310 of FIG. 13A, or any the other systems detailed herein, including utilizing the discrete devices for the individual actions disclosed in FIG. 13A. Also, any one or more of the actions can be executed by human being providing that such is possible. In this regard, method 1300 includes method action 1310, which includes placing electrodes of the galvanic stimulation subsystem at the desired locations on the head of the human. The placement of these electrodes is such that the electrodes are retained against the skin. This can be achieved via the use of an adhesive or the use of straps, etc. Any device, system, and/or method that will enable utilitarian placement and positioning of the electrodes and/or the maintenance of the positioning of the electrodes to enable the teachings detailed herein can be utilized in at least some exemplary embodiments. Method 1300 further includes method action 1320, where an impedance check is executed to verify the electrical conductive of the between the electrodes and the skin as well as to ensure electrical conductive in the between one electrode and the other, where one electrode acts as a source and the other a sink (or both can alternately act as such in the case of an alternating current). In some embodiments, the impedance check can be skipped. In some embodiments, the impedance check is automatically executed prior to testing. In this regard, the control device 620 and/or the galvanic stimulator 630, can be configured to automatically execute an impedance check. Conversely, a "hand" impedance check can be executed after the electrodes are secured to the head of the human or otherwise placed as desired. In some embodiments, skin preparation can be executed if the impedance check fails, such as, for example, shaving the area or otherwise applying a conductive gel that might be somewhat unpleasant but has utilitarian value with respect to establishing the proper impedance between the electrodes. Alternatively, and/or in addition to this, different electrodes and/or different types of electrodes can be utilized as some human physiologies may be applicable to some types of electrodes and not others. Moreover, the more invasive electrodes that have the needles that penetrate the skin, however slightly, might be instead utilized to establish utilitarian electrical conductivity between the electrodes.

In an exemplary embodiment utilizing any one or more of the systems detailed herein, at least a portion of the system can be controlled by software that follows at least a portion of the flowchart shown in FIG. 13A. The software or other control regime can automatically initially perform a check of the electrodes' impedances. In an exemplary embodiment, upon the automatic check (or more accurately, upon passing the automatic impedance check), the system is then controlled to automatically start the evaluation of the vestibular nerve(s). In an exemplary embodiment, the system can provide an indication to the user of the device that the evaluation of the vestibular nerve(s) can commence.

If the impedance check determines that there is not sufficient conductivity with respect to the electrodes placed on the head, one or more of the electrodes can be removed and repositioned on the skin, and/or one or more new electrodes can be obtained and placed on the skin. Upon a determination that the impedance check indicates utilitarian placement and conductivity of the electrodes, method 1300 proceeds to method action 1330, where stimulation is executed utilizing an initial current charge. Here, in view of the potential iterative nature of the method, the initial charge (i(n)) will be labelled as i(1).

In an exemplary embodiment, the devices and/or systems disclosed herein provide continuous stimulation, with an adjustable current of up to 8,000 microamps. The devices and/or systems can provide a pulse stimulation mode. The devices and/or systems can provide a cyclic turning on/off of stimulation, duration of complete pulse cycle/interstimulus interval of 300-2,000 ms, with an increment 100 ms, number of pulse cycles can be between 1-50. A "Sinus" stimulation mode can be provided by the devices and/or systems disclosed herein. Bipolar sinus waves, adjustable current of 0 up to 3,000 µA in 25 µA increments with an offset 0–±1,000 µA can be provided by the devices and/or systems disclosed herein. The devices and/or systems can be configured to provide increments of 1 to 100 pA (any value therebetween in 1 microamp increment), ss frequencies of 0-250 Hz, increment 0.01 Hz, adjustable phase 0-360° in 5° steps, duration 0-480 min. the devices and/or systems can provide a "noise" stimulation mode: normally distributed broadband low and high frequency noise, adjustable current of 0 up to 1,500 µA, with an offset 0–±1,000 µA, ss duration 0-1,800 s in 5 s increments, fade-in/fade out period of 0-120 s. Any one or more the above are provided in an automated manner by the devices and/or systems. Corollary to this is that methods include utilizing any one or more the aforementioned variables/values to implement any one or more the teachings detailed herein.

While the current is being applied utilizing the galvanic stimulator at the current i(1), the eye movement tracker will be capturing data indicative of movement of the eyes. Accordingly, at method action 1340, the system (in the case of an automatic system) and/or healthcare professional looks for an electro physical effect, such as an indication that the eyes have moved, which indication can be obtained from data output of the eye tracking device. If no indication is present, this may not mean that the vestibular system, and more particularly, that the nerves thereof, are not sufficiently functional for there to be utility with respect to a vestibular implant. Accordingly, in at least some exemplary embodiments, the method proceeds to method action 1350, where the current to be applied by the galvanic stimulator is increased from that of i(1), and method action 1330 is reexecuted utilizing that of the now increased current at i(2). Method action 1340 is again repeated, and again, if there is no electro physical effect noted, method 1350 is executed and method 1330 is again reexecuted, now for i(3), and this process is repeated until an electro physical effect has been detected, in which case the method action proceeds to method action 1360, which includes determining that there is a positive response, or the current cannot be increased at method action 1350 beyond that which was immediately preceded, in which case method action proceeds to method action 1370, where there is the action of determining that there is no response.

In an exemplary embodiment, the system and/or pertinent subsystem can be configured to automatically increase the current at discrete, predetermined values. In an exemplary embodiment, the increase in current can be analog, where, the current steadily increases until a reflex is identified or the current maxes out. Such an arrangement can also be digital with respect to the current increase. In an exemplary embodiment, an initial set of testing can be executed to determine a utilitarian current. In at least some exemplary embodiments, the current regime that is applied is such that it maximizes the probability of producing a vestibular to reflex.

In an exemplary embodiment, if there is no response at any current level, including the maximum current, it can be determined in at least some exemplary embodiments that the human is not a viable candidate for a vestibular stimulator. That said, in an alternate embodiment, the electrodes might be moved or otherwise adjusted and the process repeated as a safeguard. In an exemplary embodiment, method 1300 can be executed to or three or four or five times or more in a single sitting, in the course of less than an hour and/or less than two hours and/or less than three hours. Still, if there is no response that is identified, or the response is sufficiently de minimis, a determination can be made that the human is not a viable candidate for the vestibular implant.

And again, with respect to method action 1340, if a GVS is produced at method action 1330, in at least some embodiments, videonystagmography is utilized to evaluate eye torsion (e.g., otoliths) and/or translation (e.g., the phenomenon produced by the semicircular canals) and/or VEMPs, where the ocular VEMPs (utricle) and/or cervical VEMPs (saccule) is evaluated to execute method action 1340. And of course, it is to be understood that the evaluation can vary depending on the physiological recording/data set. Some eye movements will be evaluated instead of others if the eye tracking device provides input indicative of that type of eye movement. Any device, system, and/or method that can enable obtaining data indicative of one or more of the physical phenomena associated with the eye detailed herein and/or variations thereof that can enable the utilitarian teachings detailed herein can be utilized in at least some exemplary embodiments, providing that the art enable such.

In an exemplary embodiment, the eye tracking system is a video-nystagmographic system/device for eye tracking, and can be a commercially available system/device.

It is also noted that any other reflex that can be utilized to evaluate a human's candidacy for a vestibular implant can be utilized in at least some exemplary embodiments, such as, for example, a spinal reflex.

It is also noted that while the embodiment of FIG. 13 presents a feedback loop where method action 1340 is executed after each stimulation that is applied to method action 1330, in an alternate exemplary embodiment, the data from the eye tracking device can be recorded and correlated for each stimulation executed in method action 1330, but not evaluated. That is, instead of method action 1340 looking for an effect or otherwise in response, method action 1340 could be eliminated and instead, the flow would immediately go to method action 1350, where the current is increased, and so on. That is, the break in the loop would be when the maximum current is reached, and not based on a yes finding with respect to action 1340. Such an embodiment can have utilitarian value with respect to an embodiment where the data set is collected and later evaluated potentially days or weeks after the data is obtained.

Thus, it can be seen that in at least some exemplary embodiments, the system can be configured to look for an electrophysiological recording/occurrence produced by the GVS. Upon such detection or otherwise the occurrence, in at least some exemplary embodiments, it can be concluded that the vestibular nerve is working, or otherwise has sufficient functionality that a vestibular implant can be utilitarian. Conversely, if the maximum GVS current is reached, it can be assumed/deduced, or otherwise concluded that the vestibular nerve is nor working properly, or otherwise does not have sufficient functionality for a vestibular implants have utilitarian value.

Figure 14:
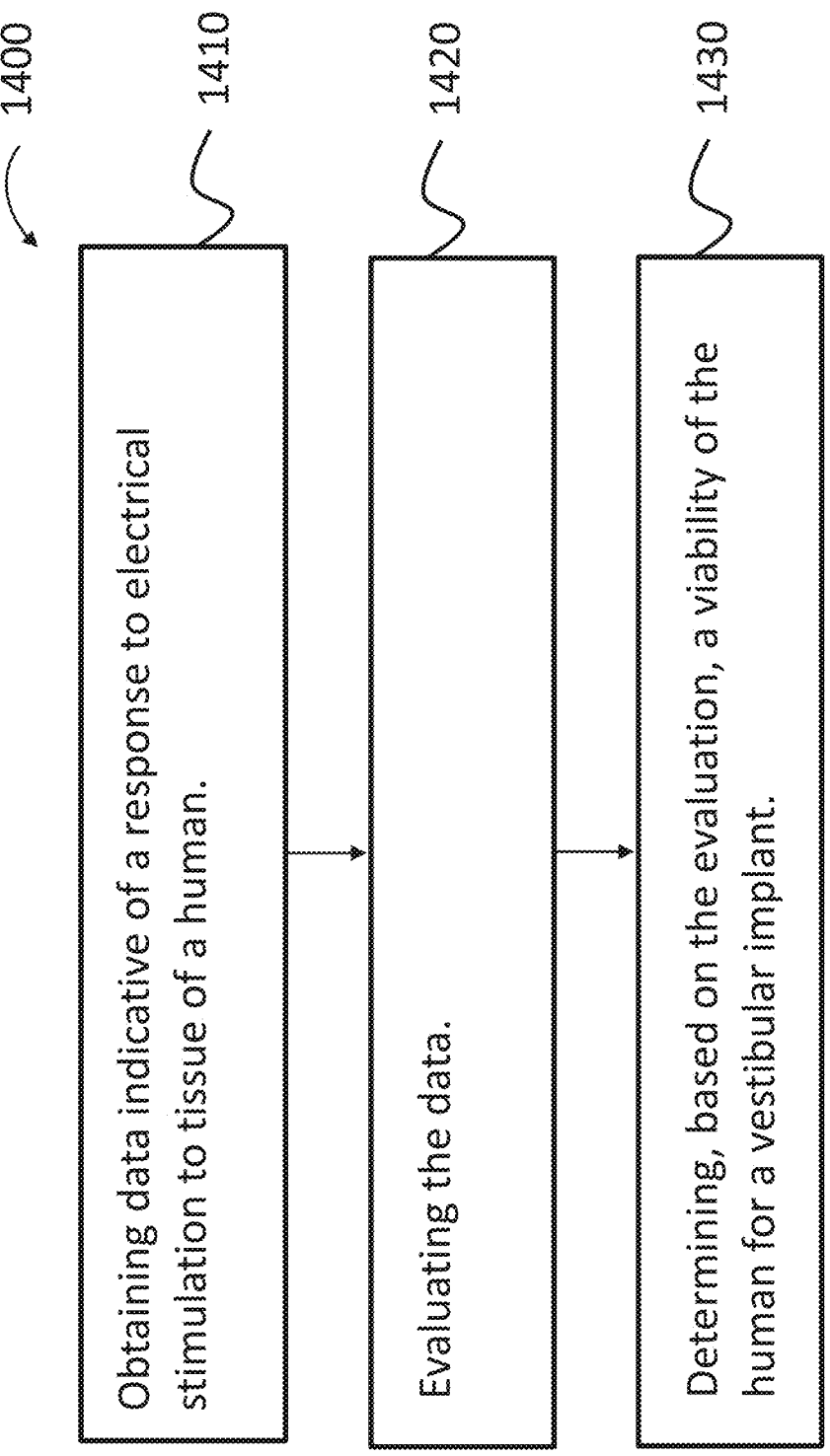

And thus, it can be seen that the teachings detailed herein can provide the use of galvanic stimulation in combination with objective measures to screen potential vestibular implant recipients. In at least some exemplary embodiments, the galvanic stimulation used herein is specifically not utilized for clinical rehabilitation of the human. That is, in at least some exemplary embodiments, any one or more or all of the actions detailed herein are explicitly excluded from use with rehabilitative galvanic stimulation/the galvanic stimulation is not utilized to rehabilitate. The galvanic stimulation is utilized to evoke a reflex, nothing more, in at least some embodiments. In an exemplary embodiment, the systems detailed herein are specifically not rehabilitative medical devices. Instead, at least some exemplary embodiments are completely limited to diagnostic medical devices/screening devices. The teachings detailed herein can provide devices systems and methods FIG. 14 presents another exemplary algorithm for another exemplary method, method 1400, according to an exemplary embodiment. Here, method 1400 includes method action 1410, which includes the action of obtaining data indicative of a response to electrical stimulation to tissue of a human. This data can be obtained directly from the eye tracking device, while in other embodiments, this can be executed by obtaining data that was previously obtained from an eye tracking device, such as, for example, data located at a remote location remote from where the eye tracking device was used. This could be, in an exemplary embodiment, a data file presenting data relating to the position of the pertinent portions of the eye(s) during the pertinent temporal periods where electrical stimulation was applied to the vestibular system. This could be a data file that has eye movement data that is correlated to temporal data and/or correlated to voltage or current readings obtained from the galvanic stimulator at times that correspond to the times that the eye tracking data was obtained. Still, in an exemplary embodiment, this can be real time data obtained from the eye tracking device 640 that is provided to, for example, the control device 620 and/or the analytical subsystem 650 or the laptop computer that is in wired communication and/or wireless communication with the eye tracking device and/or the testing device. And to be clear, in at least some exemplary embodiments, the obtained data obtained in method action 1410 is data that corresponds to eye movement that is temporarily correlated with stimulation applied to the vestibular system of a human. This is contrasted to, for example, eye movement that occurs in a manner that is not temporarily correlated with the stimulation applied to the vestibular system, where such movement that is not correlated would be discounted or otherwise ignored/disregarded in at least some exemplary methods, because the eye-movement would not be indicative of a reaction by a functioning neural system of a vestibular system / could be coincidental or otherwise might be indicative of a false positive. In this regard, in an exemplary embodiment, eye movements that take place more than 5, 4, 3, 2, 1.5, 1, 0.75, 0.5, 0.25, 0.2, or 0.1 seconds, or any value or range therebetween in 0.05 second increments after the beginning and/or the end and/or the temporal mean or median of the stimulation applied to the vestibular system are to be discounted and otherwise ignored in at least some exemplary embodiments. In an exemplary embodiment, the only eye movements that are utilized are those that take place while the stimulation is applied.

In an exemplary embodiment, the quantity and/or quality of the eye movements are recorded or otherwise collected. Such data is utilized to determine the viability of the vestibular system vis-à-vis a vestibular implant. In an exemplary embodiment, the measurements are averaged. In an exemplary embodiment, the number of times that movement appears when the GS is active is utilized to evaluate the status of the vestibular system. In this regard, in an exemplary embodiment, multiple applications of stimulation (at the current/magnitude where a response is seen) can be applied, and the results averaged (mean, median and/or mode) to determine the viability of the vestibular system. In an exemplary embodiment, 1, 2, 3, 4, 5, 6, 7, 8, 9, 10, 11, 12, 13, 14, 15 or more or any value or range of is therebetween in one increment applications of stimulation are provided to a given vestibular system where some form of response is seen. Again, consistent with some embodiments, some responses may be sufficiently de minimus that even though there is a response, such is indicative of a low likelihood including no likelihood of the vestibular system being insufficient functionality that a vestibular implant would have utilitarian value.

Method 1400 further includes method action 1420, which includes the action of evaluating the data. Again, this can be done remotely, far away from where the eye tracking data was developed/away from the eye tracking device, and/or can be done by any one or more of the above noted system, in an automated and/or utilizing an algorithm that is programmed into one or more of those machines or otherwise utilizing a machine that is configured to execute the evaluation of the data. Accordingly, in an exemplary embodiment, the action of evaluating can be executed automatically.

This can also be done by a human. By way of example only and not by way of limitation, a general eye tracking device/a commercially available eye tracking device can be utilized to execute method action 1420, and the output thereof can be evaluated in a manner consistent with how one of ordinary skill in the art would evaluate eye movements, at least with respect to the above noted physiological features associated with the eye movements that can have utilitarian value with respect to evaluating whether there is a vestibular response to the galvanic stimulation. Also as will be described below, a trained neural network or otherwise an artificial intelligence system can be utilized to execute method action 1420.

Method 1400 further includes method action 1430, which includes the action of determining, based on the evaluation, a viability of the human for a vestibular implant. This can be a determination that there is movement and/or sufficient movement of the eyes in general, and/or movement associated with one or more of the eye-movement detailed above in particular, that indicate that there is at least some functionality remaining with respect to the nervous system of the vestibular system under testing.

FIG. 15 presents another exemplary algorithm for an exemplary method, method 1500, according to an exemplary embodiment. Here, method action 1510 and 1520 or executed precedent to the action of obtaining data indicative of a response to electrical stimulation of method 1400. But method 1500 will be described in isolation for the moment. Method 1500 includes method action 1510, which include obtaining data indicative of a lack of a response to electrical stimulation to tissue of a human, wherein the lack of a response is a lack of a vestibular reflex. This can be data from the eye tracker that is indicative of a lack of movement of the eyes in general and/or a de minimis movement of the eyes in general, and, in particular, in at least some exemplary embodiments, a lack of movement with respect to the pertinent physiological features of the eye detailed above and/or a de minimis movement of the pertinent physiological features of the eye detailed above (or any other utilitarian response that can enable the teachings detailed herein). It can be seen that in at least some exemplary embodiments, method action 1510 is a method action that is executed prior to the action of obtaining data indicative of a response to electrical stimulation in method action 1400. And, in this regard, method action 1500 includes method action 1520, which includes identifying an adjustment to an electrical stimulation regime that is being used to provide the electrical stimulation to the tissue, which adjustment increases a likelihood of a vestibular reflex response. Again, in an exemplary embodiment, this can be executed prior to the action of obtaining data indicative of a response to electrical stimulation in method 1400. In an exemplary embodiment, this can include increasing the current applied to the human by the galvanic stimulator, which can be done in a manner consistent with the teachings detailed above. By way of example only and not by way of limitation, a rheostatic knob of the galvanic stimulator and/or of the control device that controls the galvanic stimulator can be adjusted such that the output current for the next stimulation is increased.

Method 1500 further includes method action 1530, which includes executing method 1400, where, in this exemplary embodiment, the data indicative of a response to electrical stimulation of method action 1410 is based on stimulation corresponding to the adjustment. And in at least some exemplary embodiments, method actions 1510 and 1520 can be repeatedly executed prior to getting to method action 1530.

Returning to the theme of the teachings detailed herein, in an exemplary embodiment, the methods detailed above, such as method 1400 and/or method 1500, further include the action of, based on the evaluation, determining that a vestibular implant is viable for the human. The method can further include the action of prescribing a vestibular implant surgery for the human. In this way, the teachings detailed herein can evaluate the applicability or otherwise the utilitarian value of a vestibular implant prior to surgery or otherwise accessing the vestibular system utilizing invasive surgery and/or prior to implanting a vestibular implant and finding that the vestibular implant is not provide utilitarian value with respect to its purpose for implantation.

In an exemplary embodiment, the methods detailed herein are such that at least 70, 75, 80, 85, 90, or 95% or more, or any value or range of values therebetween in 1% increments of the humans to which the teachings detailed herein are applied experience utilitarian value with respect to a vestibular implant that is ultimately implanted in the human. This as compared to prior art noninvasive/non-surgical techniques of evaluating the viability of a vestibular implant for a human, where the rate where the implant does not have utilitarian value after implantation is higher. And to be clear, embodiments according to the teachings detailed herein provide noninvasive and/or minimally invasive methods of evaluating the viability of a human for a vestibular implant. In an exemplary embodiment, with respect to the minimally invasive methods, a depth of penetration of a device that is utilized to execute any one or more of the method actions detailed herein extends no more than 2, 1.5, 1, 0.9, 0.8, 0.7, 0.6, 0.5, 0.4, 0.3, 0.2, or 0.1 millimeters, or any value or range of values therebetween in 0.05 mm increments. This does not include, for example, any hypodermically delivered substances that might be utilized as part of the testing.

And to recap, if the evaluation of data obtained from the eye tracking device indicates that there is no movement of the eye(s), or otherwise that the movement is de minimis, for all currents that are deemed safe and/or utilitarian to apply to the person, or at least an effective number of such, a determination can be made that the person is not a viable candidate for a vestibular implant. In corollary to this is that there could be some "false positives," as noted above. Embodiments include identifying such and discounting or otherwise eliminating the data.

In an exemplary embodiment, the identification of false positives can be based on a determination that movement was present, but the movement was below a certain threshold. An exemplary embodiment, the threshold to be correlated to current applied to the head of the recipient, where the more current applied, the greater the threshold for movement that is indicative of a vestibular response where such indicates there can be utilitarian value with respect to implantation of a vestibular implant. Further, in an exemplary embodiment, the methods are executed such that if there is an indication of eye-movement, the test will be redone at the currents and/or frequencies that are correlated to the indication of eye-movement, where if there is again eye-movement, confidence can be relatively high that the nervous system of the vestibular system is sufficiently intact or otherwise functional that there can be utilitarian value with respect to the utilization of a vestibular implant for that human.

Also, it is possible that the magnitude and/or direction and/or other physiological feature the eye-movement can be correlated between tests. If there is a recurring pattern for a given current application and/or frequency application, this can be a further indication that there can be a high confidence that the recipient can experience utilitarian value from a vestibular implant.

And in some exemplary embodiments, the action of evaluating the data of method action 1420 includes evaluating the data based on degrees of a peripheral vestibular response to the electrical stimulation. If, for example, a degree of a peripheral vestibular response is relatively high, it can be determined that there is a greater likelihood that the vestibular implant will have utilitarian value relative to that which is the case if a degree of the peripheral vestibular response is not relatively high. Corollary to this is, for example, if a degree of a peripheral vestibular response is relatively low, it can be determined that there is a much less likelihood that the vestibular implant will have utilitarian value relative to that which is the case if the degree of the peripheral vestibular response was not relatively low. While such a scenario may be the case with respect to a person that actually might benefit from a vestibular implant, this can provide a way to gauge the likelihood of success from the operation. For example, if it is deemed that the vestibular implant would be relatively traumatic to a given individual relative to the overall population of people who might be given vestibular implant, and there is a low degree of a peripheral vestibular response, a decision might be made to not give the recipient a vestibular implant, even though there is a chance that there could be utilitarian value for such.

And while the above focused on the degree of the peripheral vestibular response, other embodiments focus on the degree of other responses where there is a statistically meaningful correlation between a functioning vestibular system, or more accurately, a functioning nervous system of a particular vestibular system, and the utilitarian value of a vestibular implant.

And in some embodiments, a binary evaluation is used. In this regard, in an exemplary embodiment, the evaluator systems detailed herein are configured to look for movement in a binary manner. If the movement is present, in a manner that is outside of random occurrence and/or "noise," there can be a determination that the vestibular nerve function due to the GS exists. In an exemplary embodiment, this will correspond to a determination that the vestibular system is insufficient condition for a vestibular implant.

In at least some exemplary embodiments, the electrical stimulation to tissue of a human is applied using electrodes that are maintained at same positions during the stimulation, and the stimulation stimulates both inner ears of a human at different times. This corresponds to the example detailed above where during a setting, the electrodes are placed in the human so that both sides of the ear system /both vestibular systems can be tested without having to reattach or otherwise placed new electrodes on to the human, or otherwise interrupt the testing to place/move electrodes. Accordingly, in an exemplary embodiment, there are methods that include placing the electrodes on the human prior to commencing any testing stimulation (as opposed to impedance checks, for example), and then testing (providing stimulation and recording any movements if present) both vestibular systems without rearranging or otherwise moving the electrodes.

It can be seen from the above, that in some exemplary embodiments, there is an assembly, comprising electrodes, such as the electrodes that are configured to be placed supercutaneously on the skin of a human in general, and on the head in particular, such as at the locations detailed above. The assembly further includes an electrode stimulator in signal communication with the electrodes. This can be any of the above noted devices that are configured to provide an electrical signal to the electrodes to evoke the galvanic stimulation. And thus, it is to be understood that the electrode stimulator is configured to generate an electrical current, which is provided to the electrodes sufficient to effectively stimulate a vestibular system of a human from a location on a surface of the skin of the human. It is noted that the term generation/generate as used herein covers the concept of taking electricity that is at 120 V, 50 to 60 Hz, and using that to generate the signal that is to be applied to the electrodes. This can be done utilizing step down converters and rectifiers, etc., and can include charging capacitors or batteries, where the charge of those devices is then utilized to supply, directly or indirectly, the electrical signal to the electrodes.

But it is briefly noted that other embodiments include placement of electrodes at other locations than those detailed above. As will be momentarily described, some embodiments are utilized to test the optical nerve or otherwise to test the functionality of the nervous system of the optical system, or otherwise ocular motor system. Accordingly, in an exemplary embodiment, the electrodes could be placed on either side of the eye socket or at locations immediately above the eye and immediately below the eye, or at the center of the forehead and below and in back of the particular eye under testing. FIG. 10A depicts an exemplary placement of electrodes for such an application, by way of example.

In an exemplary embodiment, the electrode stimulator is configured to provide the electrodes sufficient electrical current to effectively stimulate a nervous system of a human from a location on a surface of the skin of the human that evokes a response related to an ocular motor system of the human. With respect to the above, this can correspond to, for example, the eye movements. But it is noted that here, in an alternate exemplary embodiment, this can be the sensation of light. In this regard, embodiments include not just devices that test and/or methods that test the nervous system of the vestibular system, but also devices and methods that test the optical nerve or otherwise nerves of the optical system, or the ocular motor system. And in this regard, in an exemplary embodiment, the assembly further includes a reflex sensor subassembly. This can be the aforementioned eye tracker, which could respond to the electrical stimulation to the vestibular system, in which also respond to, for example, electrical stimulation to the optical nerve(s) (e.g., the ocular motor nerve(s))or otherwise to the eye under testing. The eye trackers detailed above can be utilized, in some embodiments, to test this reflex. In other embodiments, brain waves can be detected utilizing sensory electrodes (which can be different from the electrodes utilized to apply stimulation). In this regard, in an exemplary embodiment, neural telemetry response can be utilized to detect whether or not nerves of the optical system in general, and the ocular motor system in particular, are at least partially functional. This can have utilitarian value with respect to evaluating whether a human is a viable candidate for a retinal prosthesis/vision prosthesis, such as that detailed above.

In an exemplary embodiment, the assembly is configured to develop reflex data utilizing the subassembly that is correlated with data indicative of stimulation provided by the electrodes. Thus, in an exemplary embodiment, the electrode stimulator is configured to generate the electrical current, which is provided to the electrodes sufficient to effectively stimulate a vestibular system of the human from the location on the surface of skin of the human, and the reflex sensor subassembly is an eye tracking subassembly, wherein the assembly is configured to develop eye tracking data using the eye tracking subassembly that is correlated with the data indicative of stimulation provided by the electrodes.

With respect to correlating data from the eye tracking device with the data indicative of stimulation provided by the electrodes, such correlation can be a temporal correlation. In an exemplary embodiment, the eye tracking device and the galvanic stimulator can be in signal communication with one another and/or controlled such that the only output that is generated by the eye tracking device during certain temporal periods is output related to eye tracking when the vestibular system is stimulated utilizing the electrodes or in close proximity thereto, such as any of the aforementioned time periods. Thus, the correlation can be achieved by the fact that there is no data from the eye tracking device that is not correlated to the stimulation applied to the vestibular system. In an exemplary embodiment, this can be achieved by controlling the galvanic stimulator and/or detecting when the galvanic stimulator is operating and then generating or otherwise accepting output from eye tracking device when the galvanic stimulator is operating, and not doing so when the galvanic stimulator is not operating. In an exemplary embodiment, this can be achieved by controlling the galvanic stimulator and/or detecting on the galvanic stimulator is operating and then "labeling" the output from the eye tracking device when the galvanic stimulator is operating or on the galvanic stimulator is not operating, so that the system or otherwise a person using the system can determine what output from the eye tracking device is correlated to the stimulation. Any device, system, and/or method of correlation can be used in at least some exemplary embodiments.

Referring to the embodiment of FIG. 12, the aforementioned assembly can be a goggle apparatus. Further, the assembly can include a dedicated software/firmware/hardware suite configured to receive data indicative of eye movement(s) detected by the eye-tracking sub-assembly and output data based on the received data. Consistent with the teachings above, the output can be the raw data of eye tracking data or can be processed data that indicates eye movement. The software/hardware/firmware suite can include software and/or hardware and/or firmware and need not include all three. Any one or more of these "wares" if present meets the phrase software/hardware/firmware suite.

In an exemplary embodiment, the dedicated software/hardware/firmware suite is configured to evaluate the received data and determine a suitability of a vestibular implant of a human whose eye movements the data received is based. In an exemplary embodiment, the suite can have access to statistical data and/or lookup tables that reference empirical and/or analytical develop data. The data from the eye tracking device in correlation with the stimulation can be compared to this database, alone or in conjunction with other human factors engineering data and/or data shown to have a statistically significant meaningful correlation to the viability of a vestibular implant in a given human (blood sugar/salt level—any data that can have utilitarian value), in an automated or semiautomated manner, and the determination as to a suitability of a vestibular implant of the human can be provided to a user.

Further, the aforementioned database can be a database that can include ranges of movements, etc. The database could be used to eliminate the so-called false positives, or otherwise be such that de minimus and/or minimal movements are accounted for in the database and, in some instances, the software is configured to indicate a lack of viability of a vestibular implant even though there is movement, based on the empirical and/or analytical data.

While the above as been directed towards a database, in some exemplary embodiments, a model can be utilized. Further, as will be detailed below, in some exemplary embodiments, a trained neural network can be utilized, where, for example, there is no true definitive algorithm for the determination that can be pointed to—the system is "trained" utilizing a statistically significant amount of data or otherwise a sufficient amount of data, as is known in the art to utilize such systems.

In an exemplary embodiment, the assembly is configured to excite a synapse between vestibular hair cells of a human and an eighth nerve afferents to evoke an eye movement, the eye-tracking subassembly being configured to detect the movement of the eye.

And it is briefly noted that any disclosure herein with respect to a vestibular system in general, and the nerves thereof in particular, as well as a vestibular implant, corresponds to a disclosure of an alternate embodiment with respect to an eye system in general, and the nerves thereof in particular, including the optic nerves, as well as a retinal implant/vision implant such disclosure being made in the interest of textual economy. To be clear, while the teachings detailed herein focus on determining the viability of a vestibular implant, based on the aforementioned statement, the teachings detailed herein are also applicable to determining the viability of a retinal implant vision implant.

Inconsistent with the teachings above, in an exemplary embodiment, with respect to the assembly under discussion, the electrodes and the subassembly are attached to a human who is conscious and who has full cognitive capabilities. This as opposed to, for example, a human who is sedated and/or has suffered traumatic brain injury or some form of brain injury. In this regard, the teachings detailed herein are not utilized to determine the state of a human's brain. In at least some embodiments, the teachings detailed herein are specifically limited to determining whether or not there is at least limited functionality remaining with respect to the nervous system of the vestibular system and/or whether or not there is at least limited functionality remaining with respect to the nervous system of the vision system, and nothing more. In an exemplary embodiment, the teachings detailed herein are executed on a human being that has the cognitive capability of a $5^{th}$ percentile to $95^{th}$ percentile human factors engineering male or female or any value or range of values therebetween in one percentile increments having one of the age groups detailed above and having one of the demographic groups detailed above. In at least some exemplary embodiments, the human is not legally blind, as that standard is applied in the United States of America and/or any of the states thereof on Mar. 20, 2021, and the person is legally responsible for his or her actions and can legally enter into contracts at the time that the testing is executed in any one or more of the states of the United States of America on that date. In an exemplary embodiment, the human undergoing testing is able to raise at least one arm to a level above his or her shoulders when asked to do so immediately before testing.

And consistent with the teachings detailed above, in an exemplary embodiment, any one or more of the method actions detailed herein are executed by a healthcare professional or by a technician for the sole purpose to determine whether or not the human is a viable candidate for a vestibular implant and/or a retinal implant. In an exemplary embodiment, the methods further include instructing, in a medically approved manner, such as by a licensed doctor or other healthcare professional licensed in the United States of America, the human to have a vestibular implant and/or a retinal implant.

And it is briefly noted that while the embodiments detailed above have been somewhat silent with respect to other sensors, in at least some exemplary embodiments, the subsystems and systems detailed above can include heart rate sensors and/or body temperature sensors and/or EKG sensors and/or EEG sensors and/or blood pressure sensors, and/or blood oxygen sensors, etc. Frustration sensors can be utilized as well. In at least some exemplary embodiments, the sensors can be utilized to obtain the pertinent information associated with the sensors from the recipient, and can be used in the overall method to determine the viability of the aforementioned prostheses for that particular human, at least where the art enable such utilitarian value with respect to utilizing such data to determine such viability.

Figure 16:
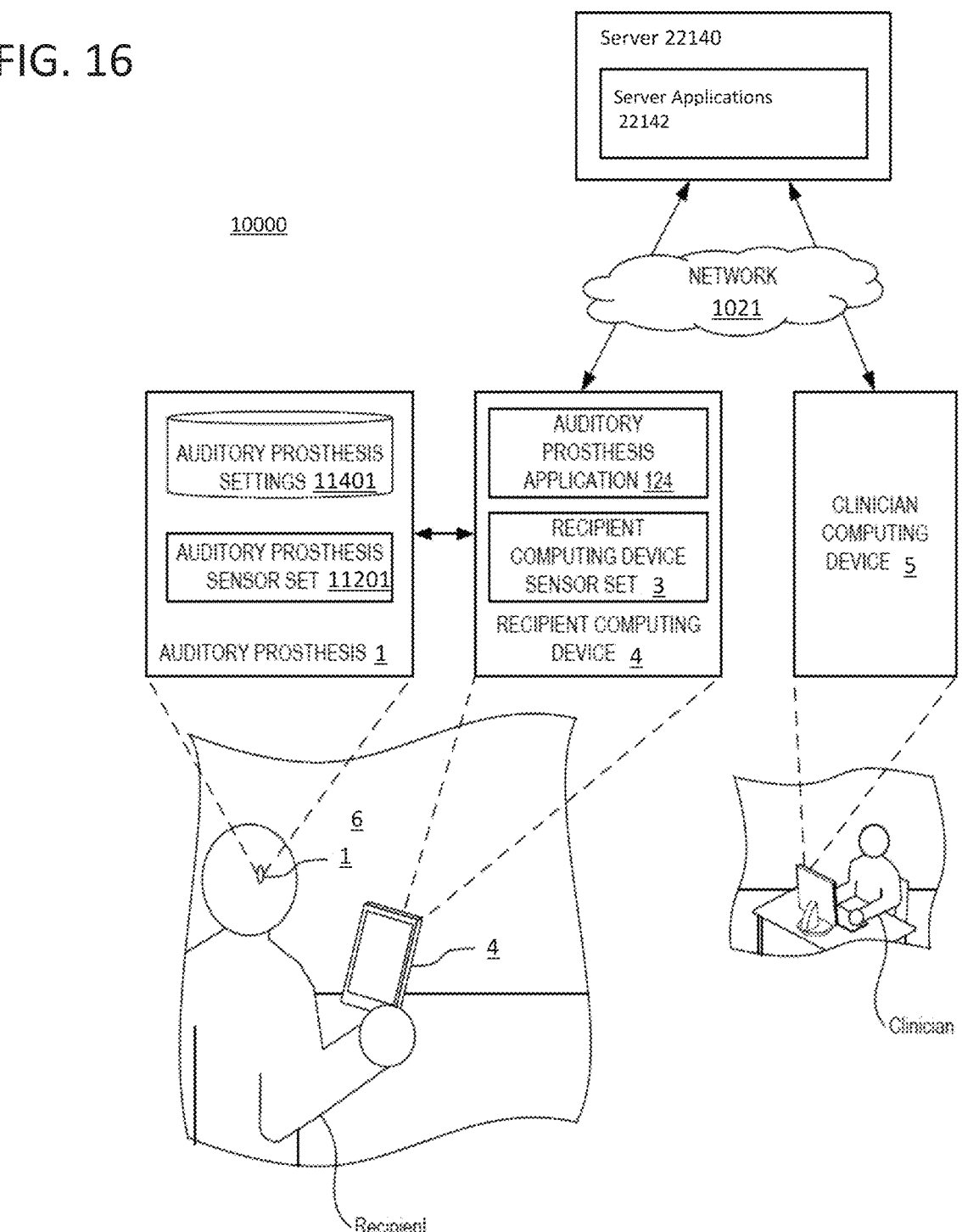
FIGS. 16 and 17 provide exemplary figures for computational systems.

FIG. 16 illustrates an exemplary subsystem 10000 that includes a subsubsystem 1 attached to the recipient/human (that is a proxy for any of the subsystems detailed herein—any system above and/or variations thereof can be a subsubsystem 1 of the subsystem 10000 in some modified embodiments of the system of FIG. 16, and any of the teachings above can be a subsystem of the subsystem 10000) that can be used with the technologies described herein, where the "recipient" is the human that is the subject of the systems herein (e.g., the human to which the electrodes are attached). The subsystem 10000 further includes a subsystem computing device 4, a clinician computing device 5, and a server 22140, which are connected over a network 1021.

The network 1021 is a computer network, such as the Internet, that facilitates the communication of data among computing devices connected to the computer network.

As illustrated, the subsystem 1 and the subsystem computing device 4 are operated by the recipient in an environment 6. The environment 6 defines the conditions in which the subsystem 1 and the subsystem computing device 4 operate. The environment 6 can affect the operation of the subsystem 1, and the subsystem 1 can be customized to operate differently in different environments 6.

The subsystem 1 is a medical apparatus relating to the test systems detailed above. The subsystem 1 can take any of a variety of forms. In the example shown, the system includes an system sensor set 11201 (e.g., the eye tracker) and operates according to system settings 11401.

The system sensor set 11201 is a collection of one or more hardware and/or software and/or firmware components of the subsystem 1 that obtain data, such as data regarding eyes, or the physiological data herein in the case of a body monitoring device, etc., the subsystem 1 , or the recipient/user. In many examples, the system sensor set 11201 include a camera, which is a proxy for any monitoring device of a sensory medical device. The system sensor set 11201 can include one or more other sensors, such as one or more accelerometers, gyroscopic sensors, location sensors, telecoils, biosensors (e.g., heart rate or blood pressure sensors), and light sensors, among others. The system sensor set 11201 can include components disposed within a housing of the subsystem 1 (or whatever medical device at issue is applicable) as well as devices electrically coupled to the subsystem 1 (e.g., via wired or wireless connections). In examples, the system sensor set 11201 includes a remote device connected to the subsystem 1 via an FM (Frequency Modulation) connection, such as a remote microphone (e.g., a COCHLEAR TRUE WIRELESS MINI MICROPHONE2+), a television audio streaming device, or a phone clip device, among other devices having FM transmission capabilities. The system sensor set 11201 can further include sensors that obtain data regarding usage of the subsystem 1 (or other data identified herein), such as software sensors operating on the subsystem 1 that track: when the subsystem 1 is used, when one or more of the system settings 11401 are modified, and how long the subsystem 1 is operated using particular settings of the system settings 11401, and/or the physiological data herein, among other data.

The system settings 11401 are one or more parameters having values that affect how the subsystem 1 operates. For instance, the system settings 11401 can include a map having minimum and maximum stimulation levels for frequency bands of stimulation channels for the electrodes. The map is then used by the subsystem 1 to control an amount of stimulation to be provided. In some examples, the system settings 11401 include two or more predefined groupings of settings selectable by the recipient. One of the two or more predefined groupings of settings may be a default setting.

The system settings 11401 can also include sound processing settings that modify sound input before it is converted into a stimulation signal. Such settings can include, for example, particular equalizer settings can boost or cut the intensity of stimulation at various frequencies. In examples, the system settings 11401 can include a minimum threshold for which the system provides stimulation, a maximum threshold for preventing stimulation above a level which would cause discomfort, gain parameters, output parameters, and/or compression parameters. The system settings 11401 can include settings that affect a dynamic range of stimulation produced by the subsystem 1. As described above, many of the system settings 11401 affect the physical operation of the subsystem 1, such as how the subsystem 1 provides stimulation to the recipient in response to sound input received from the environment 6.

The subsystem computing device 4 is a computing device associated with the recipient of the subsystem 1. In many examples, the subsystem computing device 4 is a cell phone, smart watch, or a laptop and/or desktop computer, but can take other forms, such as the control devices and/or analytical devices presented above. Although described primarily in the context of the recipient, the subsystem computing device 4 can be a computing device owned or primarily used by a parent or caregiver for the recipient. As illustrated, the subsystem computing device 4 includes a subsystem computing device sensor set 3.

The subsystem computing device sensor set 3 is group of one or more components of the subsystem computing device 4 that obtains data. The subsystem computing device sensor set 3 can include one or more sensors, such as microphones, accelerometers, gyroscopic sensors, location sensors, biosensors (e.g., heart rate or blood pressure sensors), and light sensors (e.g., cameras), among others. The subsystem computing device sensor set 3 can include components disposed within a housing of the subsystem computing device 4 as well as devices electrically coupled to the subsystem computing device 4 (e.g., via wired or wireless connections). In some examples, the subsystem computing device sensor set 3 includes software sensors, such as software that obtains data from one or more data streams (e.g., audio streamed from the subsystem computing device 4 to the subsystem 1). The subsystem computing device sensor set 3 can further include sensors that obtain data regarding how the subsystem computing device 4 itself is being used.

In examples, the subsystem computing device 4 includes an system application 124 that operates on the subsystem computing device 4 and cooperates with the subsystem 1. The system application 124 (or other medical device application 124) is a computer program stored as computer-executable instructions in memory on the subsystem computing device 4 that, when executed, performs one or more tasks relating to the subsystem 1 or otherwise whatever medical device at issue is applicable. For instance, the system application 124 can control the subsystem 1 (e.g., based on input received from the recipient), monitor usage of the subsystem 1, and obtain data from the subsystem 1. The subsystem computing device 4 can connect to the subsystem 1 using, for example, a wireless radiofrequency communication protocol (e.g., BLUETOOTH). The system application 124 transmits or receives data from the subsystem 1 over such a connection. The system application 124 can also stream audio to the subsystem 1, such as from a camera or light capture device of the subsystem computing device sensor set 3 or an application running on the subsystem computing device 4 (e.g., a video or audio application). In examples, the system application 124 functions as part of the subsystem computing device sensor set 3 by obtaining data regarding the subsystem 1. The subsystem computing device 4 can be in communication with one or both of the clinician computing device 5 and the server 22140, such as via the system application 124 communicating over the network 1021.

The clinician computing device 5 is a computing device used by a clinician. A clinician is a medical professional, such as an audiologist, or a vestibular prosthesis device technician but any disclosure herein of an audiologist, or other medical professional corresponds to an alternative disclosure of another embodiment where the person is engaged in the outfitting or otherwise provisioning of a prosthesis and/or the use of the systems above. In an example, the clinician is a medical professional that provides care or supervision for the recipient. In an example, the clinician is a proxy for another embodiment of a person that provides or otherwise works with hearing prostheses. The clinician computing device 5 includes one or more software programs usable to monitor or control the subsystem 1, such as customization of the system settings 11401.

The server 22140 is a server remote from the subsystem 1, subsystem computing device 4, and the clinician computing device 5. The server 22140 is communicatively coupled to the subsystem computing device 4 and the clinician computing device 5 via the network 1021. In many examples, the server 22140 is indirectly communicatively coupled to the subsystem 1 through the subsystem computing device 4 (e.g., via the system application 124). In some examples, the server 22140 is directly communicatively coupled to the subsystem 1. The server 22140 includes one or more server applications 22142.

The one or more server applications 22142 are computer programs stored as computer-executable instructions in memory on the server 22140 that, when executed, perform one or more tasks relating to the subsystem 10000. The one or more server applications 22142 are operable to perform one or more operations described herein, such as operations that customize the subsystem 1. As illustrated, the one or more server applications 22142 operate on the server 22140.

The components of the subsystem 10000 can cooperate to perform a method that improves the performance of the subsystem 1.

Figure 17:
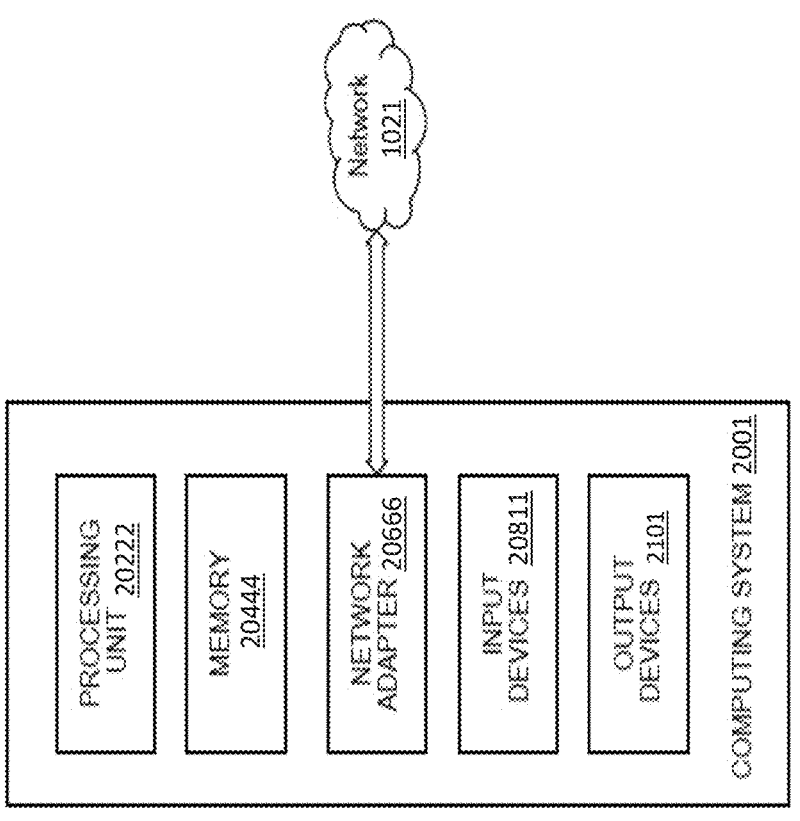

FIG. 17 illustrates an example of a suitable computing system 2001 with which one or more of the disclosed embodiment can be implemented, where one or more or all of the disclosed method actions herein that are automated or otherwise computer-based can be implemented utilizing the arrangement of FIG. 17. Computing systems, environments, or configurations that can be suitable for use with examples described herein include, but are not limited to, personal computers, server computers, hand-held devices, laptop devices, multiprocessor systems, microprocessor-based systems, programmable consumer electronics (e.g., smart phones), network PCs, minicomputers, mainframe computers, tablets, distributed computing environments that include any of the above systems or devices, and the like. The computing system 2001 can be a single virtual or physical device operating in a networked environment over communication links to one or more remote devices. The remote device can be a system (e.g., the subsystem 1), a personal computer, a server, a router, a network personal computer, a peer device or other common network node. In examples, the subsystem computing device 4, the clinician computing device 5, and the server 22140 includes one or more components or variations of components of the computing system 2001. Further, in some examples, the subsystem 1 includes one or more components of the computing system 2001.

In its most basic configuration, computing system 2001 includes at least one processing unit 20222 and memory 20444.

The processing unit 20222 includes one or more hardware or software processors (e.g., Central Processing Units) that can obtain and execute instructions. The processing unit 20222 can communicate with and control the performance of other components of the computing system 2001. The memory 20444 is one or more software- or hardware-based computer-readable storage media operable to store information accessible by the processing unit 20222. The memory 20444 can store, among other things, instructions executable by the processing unit 20222 to implement applications or cause performance of operations described herein, as well as other data. The memory 20444 can be volatile memory (e.g., RAM), non-volatile memory (e.g., ROM), or combinations thereof. The memory 20444 can include transitory memory or non-transitory memory. The memory 20444 can also include one or more removable or non-removable storage devices. In examples, the memory 20444 can include RAM, ROM, EEPROM (Electronically-Erasable Programmable Read-Only Memory), flash memory, optical disc storage, magnetic storage, solid state storage, or any other memory media usable to store information for later access. In examples, the memory 20444 encompasses a modulated data signal (e.g., a signal that has one or more of its characteristics set or changed in such a manner as to encode information in the signal), such as a carrier wave or other transport mechanism and includes any information delivery media. By way of example, and not limitation, the memory 20444 can include wired media such as a wired network or direct-wired connection, and wireless media such as acoustic, RF, infrared and other wireless media or combinations thereof In the illustrated example, the system 2001 further includes a network adapter 20666, one or more input devices 2081, and one or more output devices 2101. The system 2001 can include other components, such as a system bus, component interfaces, a graphics system, a power source (e.g., a battery), among other components.

The network adapter 20666 is a component of the computing system 2001 that provides network access. The network adapter 20666 can provide wired or wireless network access and can support one or more of a variety of communication technologies and protocols, such as ETHERNET, cellular, BLUETOOTH, near-field communication, and RF (Radiofrequency), among others. The network adapter 20666 can include one or more antennas and associated components configured for wireless communication according to one or more wireless communication technologies and protocols.

The one or more input devices 20811 are devices over which the computing system 2001 receives input from a user. The one or more input devices 20811 can include physically-actuatable user-interface elements (e.g., buttons, switches, or dials), touch screens, keyboards, mice, pens, and voice input devices, among others input devices.

The one or more output devices 2101 are devices by which the computing system 2001 is able to provide output to a user. The output devices 2101 can include, displays, speakers, and printers, among other output devices.

And in this regard, any one or more of the functionalities and method actions and/or devices detailed above can be implemented utilizing, at least in part, any one or more of the facets associated with FIG. 16 and/or FIG. 17. By way of example only and not by way limitation, the analytical subsystem detailed above can correspond to the computing system 2001. Further by way of example, the arrangement of system 1000 can be utilized to "integrate" the various subsystem detailed above, where the various subsystems correspond to one or more of the various elements of the system 1000.

It is noted that any method action disclosed herein corresponds to a disclosure of a non-transitory computer readable medium that has program there on a code for executing such method action providing that the art enables such. Still further, any method action disclosed herein where the art enables such corresponds to a disclosure of a code from a machine learning algorithm and/or a code of a machine learning algorithm for execution of such. Still as noted above, in an exemplary embodiment, the code need not necessarily be from a machine learning algorithm, and in some embodiments, the code is not from a machine learning algorithm or the like. That is, in some embodiments, the code results from traditional programming. Still, in this regard, the code can correspond to a trained neural network. That is, as will be detailed below, a neural network can be "fed" significant amounts (e.g., statistically significant amounts) of data corresponding to the input of a system and the output of the system (linked to the input), and trained, such that the system can be used with only input, to develop output (after the system is trained). This neural network used to accomplish this later task is a "trained neural network." That said, in an alternate embodiment, the trained neural network can be utilized to provide (or extract therefrom) an algorithm that can be utilized separately from the trainable neural network. In one embodiment, there is a path of training that constitutes a machine learning algorithm starting off untrained, and then the machine learning algorithm is trained and "graduates," or matures into a usable code— code of trained machine learning algorithm. With respect to another path, the code from a trained machine learning algorithm is the "offspring" of the trained machine learning algorithm (or some variant thereof, or predecessor thereof), which could be considered a mutant offspring or a clone thereof. That is, with respect to this second path, in at least some exemplary embodiments, the features of the machine learning algorithm that enabled the machine learning algorithm to learn may not be utilized in the practice some of the method actions, and thus are not present the ultimate system. Instead, only the resulting product of the learning is used.

And to be clear, in an exemplary embodiment, there are products of machine learning algorithms (e.g., the code from the trained machine learning algorithm) that are included in any one or more of the systems/subsystems detailed herein, that can be utilized to analyze any of the data obtained or otherwise available disclosed above that can be utilized or otherwise is utilized to evaluate the utilitarian value of any one or more of the implants detailed herein. This can be embodied in software code and/or in computer chip(s) that are included in the system(s).

An exemplary system includes an exemplary device/ devices that can enable the teachings detailed herein, which in at least some embodiments can utilize automation. That is, an exemplary embodiment includes executing one or more or all of the methods detailed herein and variations thereof, at least in part, in an automated or semiautomated manner using any of the teachings herein. Conversely, embodiments include devices and/or systems and/or methods where automation is specifically prohibited, either by lack of enablement of an automated feature or the complete absence of such capability in the first instance.

It is further noted that any disclosure of a device and/or system detailed herein also corresponds to a disclosure of otherwise providing that device and/or system and/or utilizing that device and/or system.

It is also noted that any disclosure herein of any process of manufacturing other providing a device corresponds to a disclosure of a device and/or system that results there from. Is also noted that any disclosure herein of any device and/or system corresponds to a disclosure of a method of producing or otherwise providing or otherwise making such.

An exemplary system includes an exemplary device/ devices that can enable the teachings detailed herein, which in at least some embodiments can utilize automation, as will now be described in the context of an automated system. That is, an exemplary embodiment includes executing one or more or all of the methods detailed herein and variations thereof, at least in part, in an automated or semiautomated manner using any of the teachings herein.

It is further noted that any disclosure of a device and/or system detailed herein also corresponds to a disclosure of otherwise providing that device and/or system and/or utilizing that device and/or system.

It is also noted that any disclosure herein of any process of manufacturing other providing a device corresponds to a disclosure of a device and/or system that results there from. Is also noted that any disclosure herein of any device and/or system corresponds to a disclosure of a method of producing or otherwise providing or otherwise making such.

Any embodiment or any feature disclosed herein can be combined with any one or more or other embodiments and/or other features disclosed herein, unless explicitly indicated and/or unless the art does not enable such. Any embodiment or any feature disclosed herein can be explicitly excluded from use with any one or more other embodiments and/or other features disclosed herein, unless explicitly indicated that such is combined and/or unless the art does not enable such exclusion.

Any function or method action detailed herein corresponds to a disclosure of doing so an automated or semiautomated manner.

While various embodiments of the present invention have been described above, it should be understood that they have been presented by way of example only, and not limitation. It will be apparent to persons skilled in the relevant art that various changes in form and detail can be made therein without departing from the spirit and scope of the invention.

What is claimed is:

1. A system, comprising:
   a galvanic stimulator; and
   an eye tracking device, wherein
   the system is a clinical vestibular implant suitability evaluation system,
   the eye tracking device includes a videonystagmography recording sub-system, and
   the system further comprises a vestibular evoked myogenic potentials (VEMPs) sub-system configured to record vestibulo-ocular and/or vestibulo-spinal reflex(es).

2. The system of claim 1, further comprising:

a computing apparatus configured to analyze eye tracking data generated by the eye tracking device and provide output indicative of the analysis.

3. The system of claim 1, further comprising:

a computing apparatus configured to analyze eye tracking data generated by the eye tracking device and, based on the analysis, automatically provide an indication of whether a vestibular implant would be utilitarian for a human stimulated by the galvanic stimulator and who's eyes are tracked by the eye tracking device.

4. The system of claim 1, wherein:

the system is established by a head-worn apparatus.

5. The system of claim 1, wherein:

the system is configured to electrically evoke a vestibular reflex in a human with at least a partially functioning neural system of the human's vestibular system.

6. The system of claim 1, wherein:

the system is established in part by a head-worn apparatus and is established in part by a computing apparatus separate from the head-worn apparatus.

7. The system of claim 1, wherein:

the system is configured to automatically obtain data indicative of a response to stimulation by the galvanic stimulator applied to a person.

8. The system of claim 7, wherein:

the system is configured to automatically evaluate the obtained data; and the obtained data includes vision related data, wherein the evaluation of the obtained data includes determining a degree of peripheral vestibular response that occurs based on the stimulation by the galvanic stimulator applied to the person.

9. The system of claim 7, wherein:

the obtained data is eye movement data that is temporally correlated with the stimulation applied by the galvanic stimulator.

10. The system of claim 7, wherein:

the system is configured to automatically evaluate the obtained data; and the system is configured to automatically determine a viability of the person for the vestibular implant based on the evaluation of the obtained data.

11. The system of claim 7, wherein:

the system is configured to automatically determine that there is a lack of response to stimulation by the galvanic stimulator applied to the person.

12. The system of claim 11, wherein:

the system is configured to automatically identify an adjustment to an electrical stimulation regime implemented by the system using the galvanic stimulator based at least on the determination that there is a lack of response to the stimulation applied by the galvanic stimulator applied to the person.

13. The system of claim 1, wherein:

the system is configured to apply stimulation to both inner ears of a person at different times.

14. An assembly, comprising: electrodes; an electrode stimulator in signal communication with the electrodes, the electrode stimulator configured to generate an electrical current, which is provided to the electrodes sufficient to effectively stimulate a nervous system of a human from a location on a surface of skin of the human that evokes a response related to an ocular motor system of the human; and an eye tracking subassembly and/or an electrical potential sensor subassembly, wherein the assembly is configured to develop reflex data using the subassembly that is correlated with data indicative of stimulation provided by the electrodes, and system is established in part by a head-worn apparatus and is established in part by a computing apparatus separate from the head-worn apparatus.

15. The assembly of claim 14, wherein the assembly includes the eye tracking subassembly, and wherein the eye tracking subassembly includes a videonystagmography recording device.

16. The assembly of claim 14, wherein the assembly includes the electrical potential sensor subassembly, and wherein the electrical potential sensor subassembly is a vestibular evoked myogenic potentials (VEMPs) sub-system configured to record vestibulo-ocular and/or vestibulo-spinal reflex(es).

17. The assembly of claim 14, wherein:

the electrode stimulator is configured to generate the electrical current, which is provided to the electrodes sufficient to effectively stimulate a vestibular system of the human from the location on the surface of skin of the human; and the assembly is configured to develop eye tracking data using the eye tracking subassembly that is correlated with the data indicative of stimulation provided by the electrodes.

18. The assembly of claim 17, wherein:

the assembly is configured to excite a synapse between vestibular hair cells of a human and an eighth nerve afferents to evoke an eye movement, the eye-tracking subassembly being configured to detect the movement of the eye.

19. The assembly of claim 14, further comprising:

a dedicated software/hardware/firmware suite configured to receive data indicative of eye movement(s) detected by the eye-tracking sub-assembly and output data based on the received data; and the dedicated software/hardware/firmware is configured to evaluate the received data and determine a suitability of a vestibular implant of a human whose eye movements the data received is based.

* * * * *